(12) United States Patent
Skalka et al.

(10) Patent No.: US 9,533,040 B2
(45) Date of Patent: Jan. 3, 2017

(54) INHIBITION OF HUMAN IMMUNODEFICIENCY VIRUS INTEGRASE REACHING DIMER FORMATION UTILIZING SINGLE-CHAIN VARIABLE ANTIBODIES

(71) Applicant: Institute for Cancer Research, Philadelphia, PA (US)

(72) Inventors: Anna Marie Skalka, Princeton, NJ (US); Mark Andrake, Huntingdon Valley, PA (US); Ravi Shankar Bojja, Philadelphia, PA (US)

(73) Assignee: Institute for Cancer Research, Philadelphia, PA (US)

( * ) Notice: Subject to any disclaimer, the term of this patent is extended or adjusted under 35 U.S.C. 154(b) by 114 days.

(21) Appl. No.: 13/923,494

(22) Filed: Jun. 21, 2013

(65) Prior Publication Data
US 2013/0280271 A1    Oct. 24, 2013

Related U.S. Application Data

(63) Continuation-in-part of application No. PCT/US2011/067200, filed on Dec. 23, 2011.

(60) Provisional application No. 61/426,615, filed on Dec. 23, 2010, provisional application No. 61/430,593, filed on Jan. 7, 2011.

(51) Int. Cl.
| C12Q 1/34 | (2006.01) |
| C07K 16/10 | (2006.01) |
| A61K 39/395 | (2006.01) |
| C12Q 1/18 | (2006.01) |
| C12N 9/22 | (2006.01) |

(52) U.S. Cl.
CPC ............. *A61K 39/3955* (2013.01); *C12N 9/22* (2013.01); *C12Q 1/18* (2013.01); *C12Q 1/34* (2013.01); *C07K 16/1054* (2013.01); *C12N 2740/11022* (2013.01); *C12N 2740/16211* (2013.01); *C12N 2740/16222* (2013.01); *G01N 2333/161* (2013.01); *G01N 2333/922* (2013.01)

(58) Field of Classification Search
CPC ............. C12Q 1/34; C12N 2740/16211; C07K 16/1054; G01N 2333/161
See application file for complete search history.

(56) References Cited

U.S. PATENT DOCUMENTS 7,071,227 B2    7/2006 Huang et al.

FOREIGN PATENT DOCUMENTS

WO    2008042806    4/2008

OTHER PUBLICATIONS

Maroun, R. G., et al., 2001, Peptide inhibitors of HIV-1 integrase dissociate the enzyme oligomers, Biochem. 40:13840-13848.*
Levy-Mintz, P., et al., Dec. 1996, Intracellular expression of single-chain variable fragments to inhibit early stages of the viral life cycle by targeting human immunodeficiency virus type 1 integrase, J. Virol. 70(12):8821-8832.*
Yi, J., et al., Dec. 2000, An inhibitory monoclonal antibody binds at the turn of the helix-turn-helix motif in the N-terminal domain of HIV-1 integrase, J. Biol. Chem. 275(49):38739-38748.*
Yi, J., et al., Apr. 2002, Mapping the epitope of an inhibitory monoclonal antibody to the C-terminal DNA-binding domain of HIV-1 integrase, J. Biol. Chem. 277(14):12164-12174.*
Bojja, R. S., et al., May 2011, Architecture of a full-length retroviral integrase monomer and dimer, revealed by small angle x-ray scattering and chemical cross-linking, J. Biol. Chem. 286(19):17047-17059.*
Maroun, et al., "Peptide inhibitors of HIB-1 integrase dissociate the enzyme oligomers", Bochemistry, Nov. 20, 2001, vol. 40, No. 46, pp. 13840-13848.
Ramcharan, et al., "Mode of inhibition of HIV-1 integrase by C-terminal domain-specific monoclonal antibody", Retrovirology, Jun. 21, 2006, vol. 3, p. 34.
Moreau, et al., "Mutations in c-terminal domain of ALSV (Avian Leukemia and Sarcoma Viruses) integrase alter the concerted DNA integration process in vitro", Eur. J. Biochem., Nov. 2003, vol. 270, No. 22, pp. 4426-4438.
Yi, et al., "An inhibitory monoclonal antibody binds at the turn of the helix-turn-helix motif in the N-terminal domain of the HIV-1 integrase", J. Biol. Chem., Dec. 8, 2000, vol. 275, No. 49, pp. 38739-38748.
Al-Mawsawi, et al., "Four-tiered pi interaction in the dimeric interface of HIV-1 integrase critical for DNA integration and viral infectivity", Viroloty, Aug. 1, 2008, vol. 377, No. 2, pp. 355-363.
Nilsen, et al., "Monoclonal Antibodies against Human Immunodeficiency Virus Type 1 Integrase: Epitope Mapping and Differential Effects on Integrase Activities in Vitro", J. Virol., Mar. 1996, vol. 70, No. 3, pp. 1580-1587.
Barsov, et al., "Inhibition of human immunodeficiency virus type 1 integrase by the Fab fragment of a specific monoclonal antibody suggests that different multimerization states are required for different enzymatic functions", J. Virol., Jul. 1996, vol. 70, No. 7, pp. 4484-4494.
Lou, et al., "Prospective strategies for targeting HIV-1 integrase function", Future Med. Chem, Jul. 1, 2010, vol. 2, No. 7, pp. 1055-1060.
Ceccherini-Silberstein, et al., "Characterization and structural analysis of HIV-1 integrase conservation", AIDS Rev., Jan.-Mar. 2009; 11(1):17-29.
Bizub-Bender, et al., "Monoclonal antibodies against HIV type 1 integrase: clues to molecular structure", AIDS Res. Hum. Retroviruses, Sep. 1994;10(9):1105-15.

(Continued)

*Primary Examiner* — Jeffrey Parkin
(74) *Attorney, Agent, or Firm* — Stradley Ronon Stevens & Young, LLP

(57) ABSTRACT

Methods to inhibit the formation of retrovirus integrase reaching dimers, to dissociate retrovirus integrase reaching dimers, and to stabilize retrovirus integrase reaching dimers in a conformation in which retrovirus DNA-to host cell DNA integration activity of the integrase is inhibited are provided. Methods for treating a retrovirus infection, which target retrovirus integrase reaching dimer formation and/or stability are also provided.

12 Claims, 35 Drawing Sheets

(56) References Cited

OTHER PUBLICATIONS deVries, et al., "The HADDOCK web server for data-driven biomolecular docking", Nat. Protoc., May 2010;5(5):883-97.
Bao, et al., "Functional Oligomeric State of Avian Sarcoma Virus Integrase", J. Biol. Chem., vol. 278, No. 2, Jan. 10, 2003, pp. 1323-1327.
Faure, et al., "HIV-1 integrase crosslinked oligomers are active in vitro", Nucleic Acids Research, 2005, vol. 33, No. 3, pp. 977-986.
Li, et al., "Retroviral DNA integration: reaction pathway and critical intermediates", The EMBO Journal, 2006, 25, pp. 1295-1304.
Hare, et al., "Retroviral intasome assembly and inhibition of DNA strand transfer", Nature, Mar. 11, 2010, 464 (7286):232-236.
Levy-Mintz, et al., "Intracellular Expression of Single-Chain Variable Fragments to Inhibit Early Stages of the Viral Life Cycle by Tarteting Human Immunodeficiency Virus Type 1 Integrase", J. of Virology, Dec. 1996, pp. 8821-8832.
Andrake, et al., "Comparison of metal-dependent catalysis of HIV-1 and ASV integrase proteins using a new and rapid, moderate throughput assay for joining activity in solution", AIDS Research and Therapy, 2009, 6:14.
Merkel, et al., "Oligonucleotide-based assays for integrase activity", Methods, Apr. 2009; 47(4):243-248.
International Search Report and Written Opinion from PCT/US2011/067200, dated Oct. 16, 2012.
Yi, et al., "Mapping the Epitope of an Inhbitory Monoclonal Antibody to the C-terminal DNA-binding Domain of HIV-1 Integrase", J. Biol. Chem., vol. 277, No. 14, Apr. 5, 2002, pp. 12164-12174.

* cited by examiner

Integrase Domains

Fig. 1C. "Core – stabilized" composite dimer model
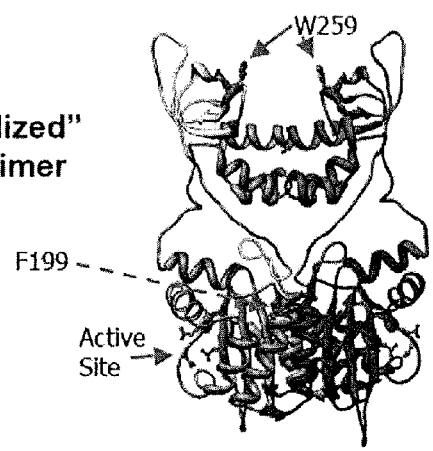

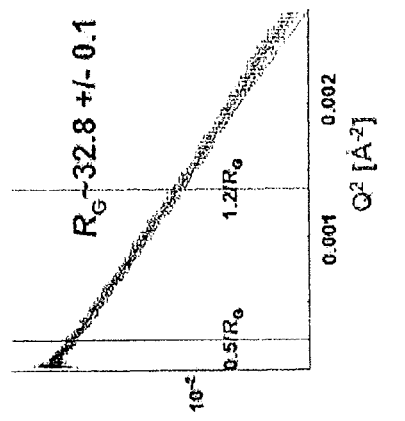
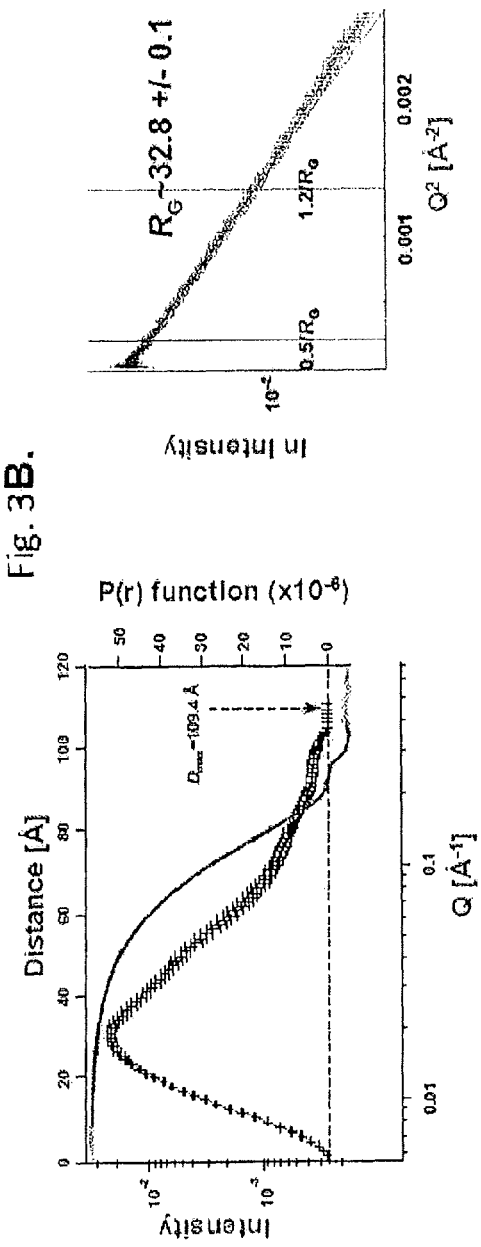
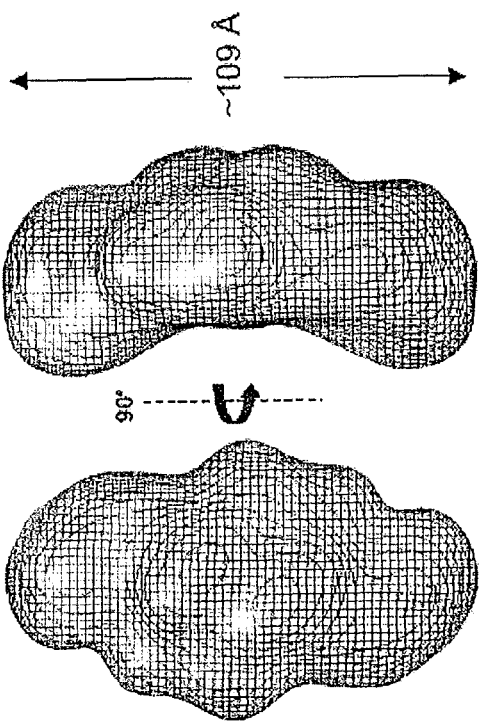
Fig. 3A.
Fig. 3B.
Fig. 3C.

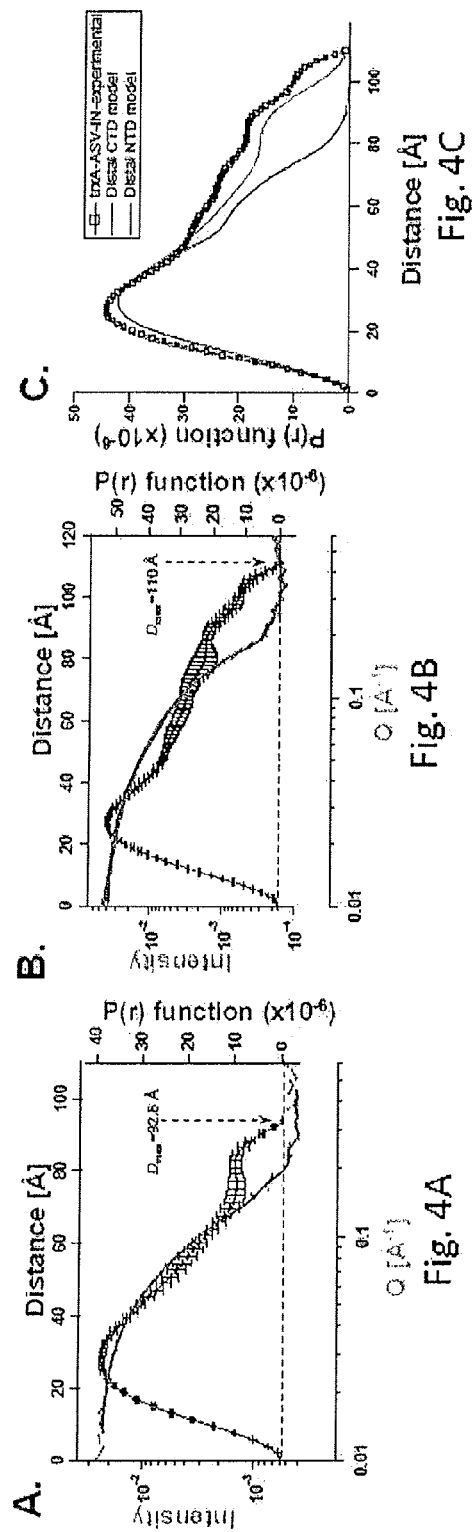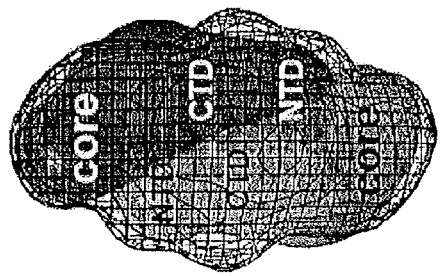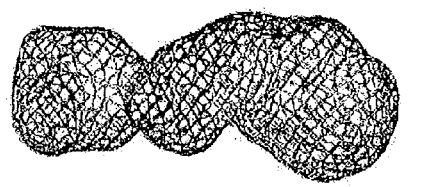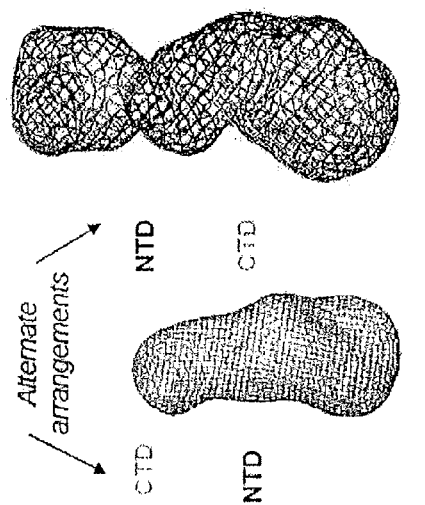
Fig. 4A
Fig. 4B
Fig. 4C
Fig. 4D
Fig. 4E

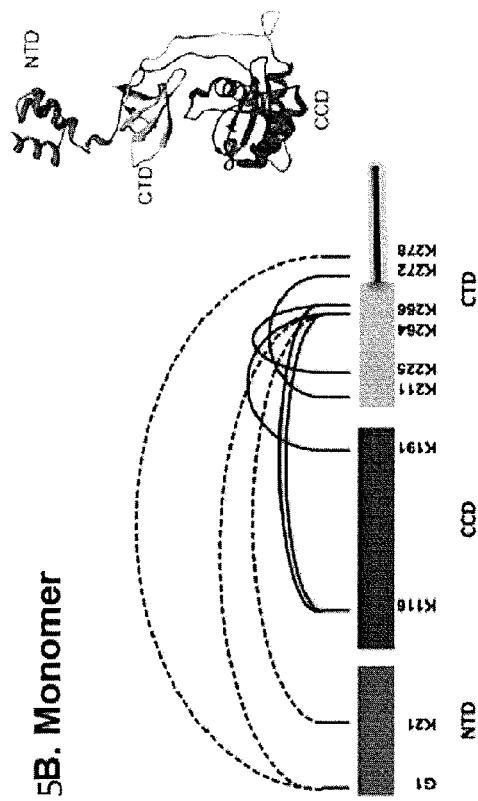
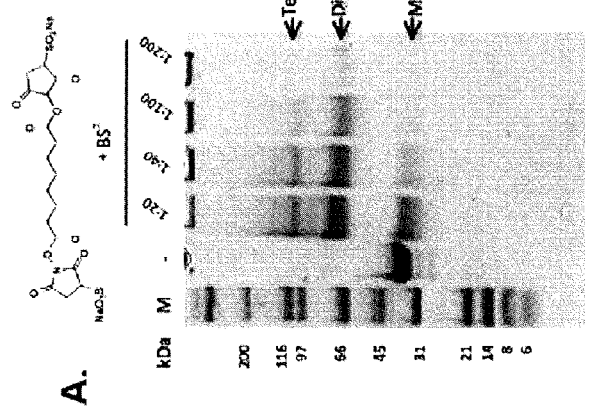
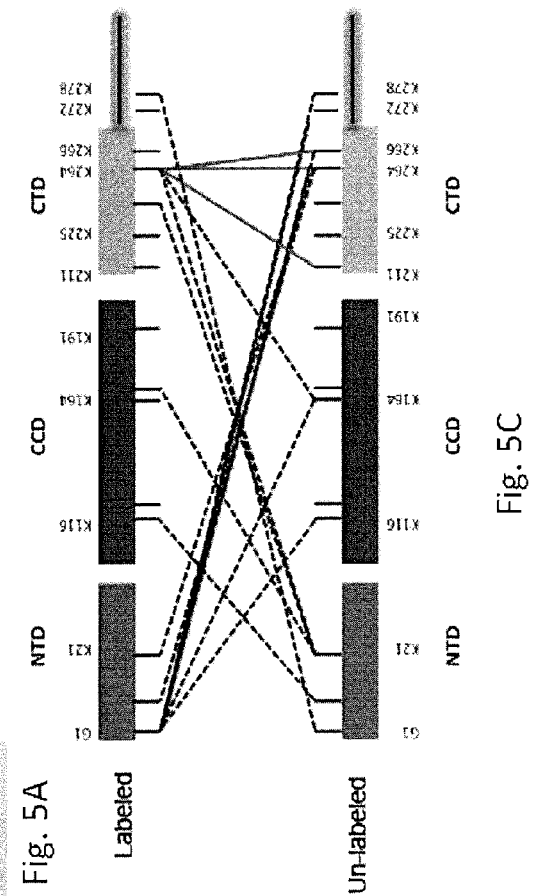

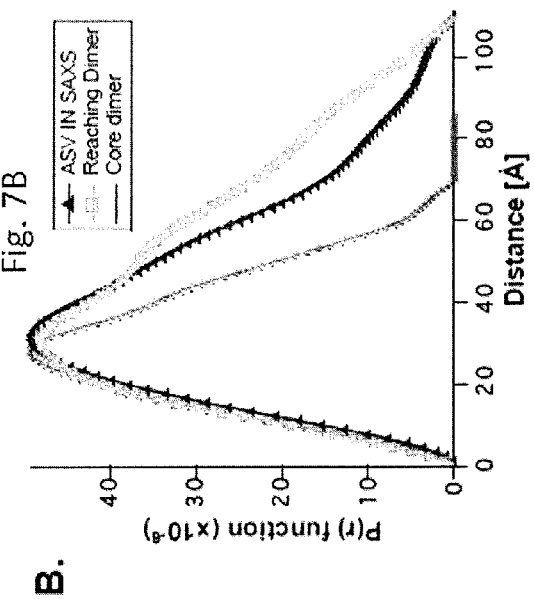
Fig. 7A
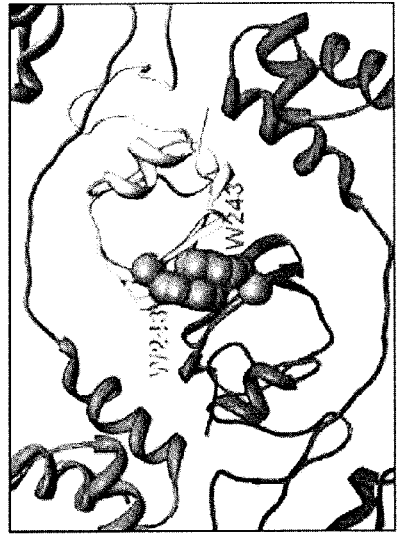
Fig. 7B
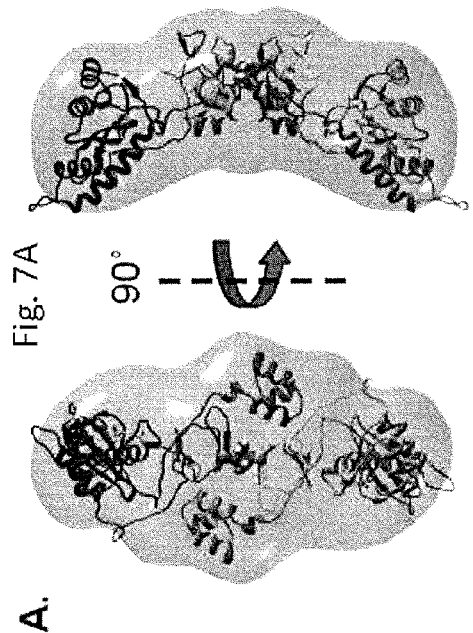
Fig. 7C ASV IN
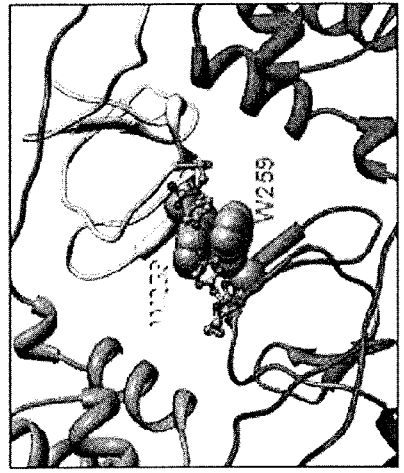
Fig. 7D HIV IN

| Docking | HADDOCK Score | Number of Structures | RMSD (Å)* | $E_{VDW}$ (kcal mol$^{-1}$) | $E_{ele}$ (kcal mol$^{-1}$) | Desolvation Energy (kcal mol$^{-1}$) | Restraints Violation energy (kcal mol$^{-1}$) | Buried Surface Area (Å$^2$) |
|---|---|---|---|---|---|---|---|---|
| Run 1 | | | | | | | | |
| Step 1 | -72.4 +/-23.7 | 4 | 3.2 +/-0.9 | -30.2 +/-11.5 | -179.4 +/-89.4 | -8.8 +/-16.6 | 25.0 +/-14.28 | 1175.7 +/-287.7 |
| Run 2 | | | | | | | | |
| Step 2 | -104.9 +/-11.2 | 7 | 5.8+/-1.2 | -54.0 +/-16.0 | -230.3 +/-59.4 | -8.5 +/-13.6 | 36.4 +/-21.21 | 1949.6 +/-330.7 |
| Run 3[b] | | | | | | | | |
| Step 3 | -52.1+/-1.6 | 200 | 0.5+/-0.3 | -70.7 +/-6.6 | -243.4 +/-8.0 | 2.0 +/-7.0 | 640.5 +/-3.57 | 2250.1 +/-141.8 |

* Average RMSD and standard deviation from the lowest energy of the cluster, [b] symmetry imposed docking run

Fig. 10A

ISOTOPICALLY LABELED WILD TYPE ASV INTEGRASE

|  | 10 | 20 | 30 | 40 | 50 |
|---|---|---|---|---|---|
| GHM | PLREAKDLHT | ALHIGPRALS | KACNISMQQA | REVVQTCPHC | NSAPALEAGV |
|  | 60 | 70 | 80 | 90 | 100 |
|  | NPRGLGPLQI | WQTDFTLEPR | MAPRSWLAVT | VDTASSAIVV | TQHGRVTSVA |
|  | 110 | 120 | 130 | 140 | 150 |
|  | AQHHWATAIA | VLGRPKAIKT | DNGSCFTSKS | TREWLARWGI | AHTTGIPGNS |
|  | 160 | 170 | 180 | 190 | 200 |
|  | QGQAMVERAN | RLLKDKIRVL | AEGDGFMKRI | PTSKQGELLA | KAMYALNHFE |
|  | 210 | 220 | 230 | 240 | 250 |
|  | RGENTKTPIQ | KHWRPTVLTE | GPPVKIRIET | GEWEKGWNVL | VWGRGYAAVK |
|  | 260 | 270 | 280 |  |  |
|  | NRDTDEVIWV | PSRKVKPDIT | QKDEVTKKDE | ASPLFA | (SEQ ID NO:5) |

Fig. 12

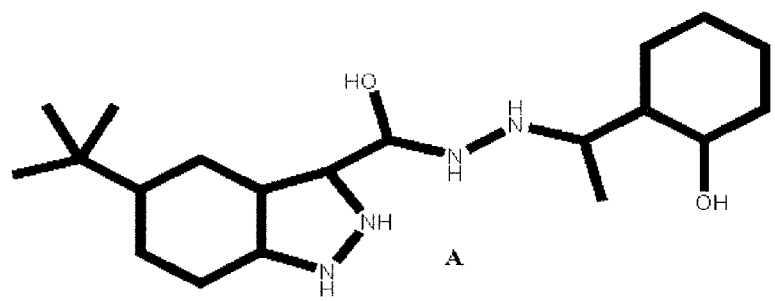
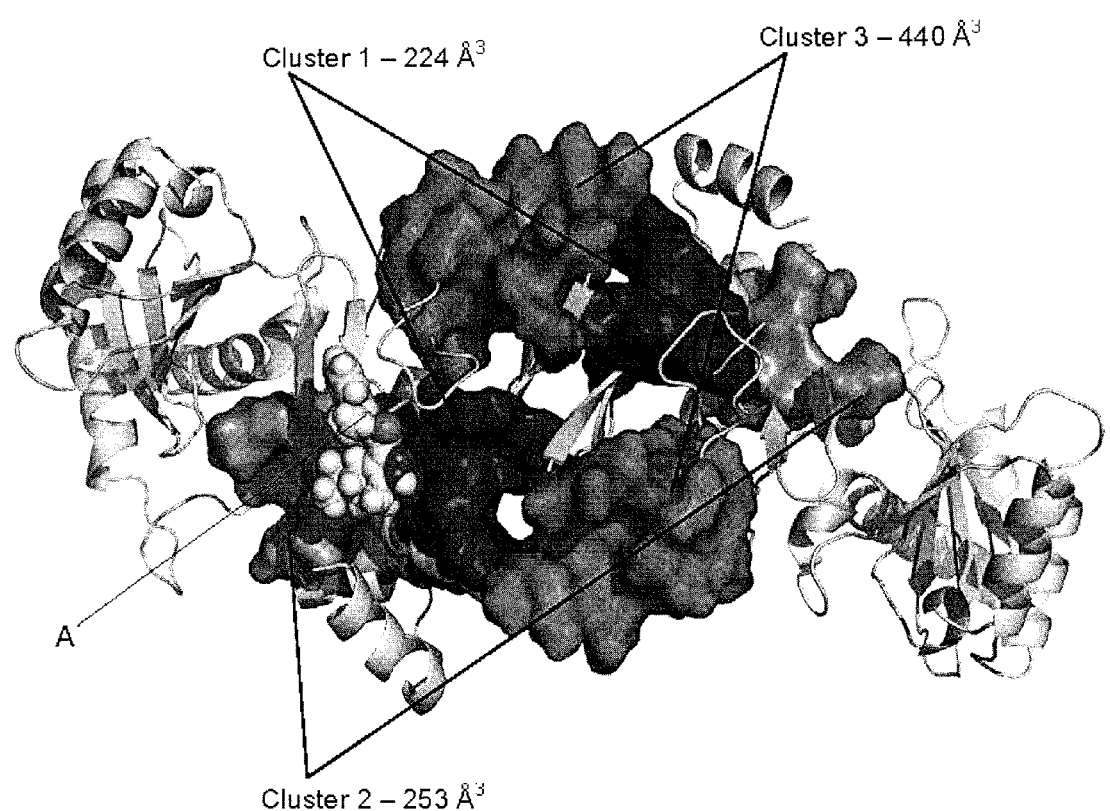
Fig. 15

| Protein | Rg (Å) | Dmax (Å) | Volume (x1000 Å$^3$) | mg/ml | Apparent Multimer (LS) |
|---|---|---|---|---|---|
| HIV-1 IN Wildtype | 41 | 105 | 290 | 1.2 | tetramer |
| HIV-1 IN F181T | 36 | 107 | 130 | 1.1 | dimer |
| ASV-IN-WT | 33 | 109 | 129 | 2.3 | dimer |
| PFV-IN-WT | 38 | 117 | 95 | 4.3 | monomer |

IN envelopes & volumes

HIV tetramer (290k-A$^3$)

PFV monomer (95k-A$^3$)

ASV dimer (129k-A$^3$)

F181T dimer (130k-A$^3$)

DED= last three residues of HIV IN protein

B.
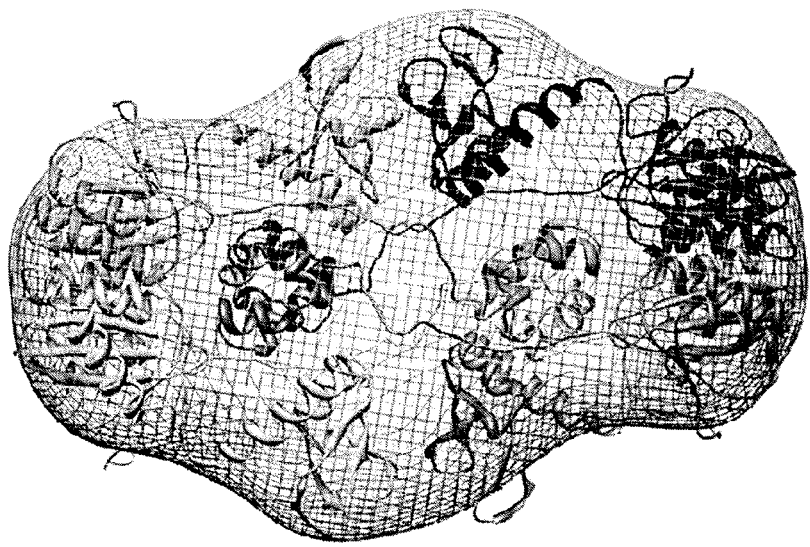
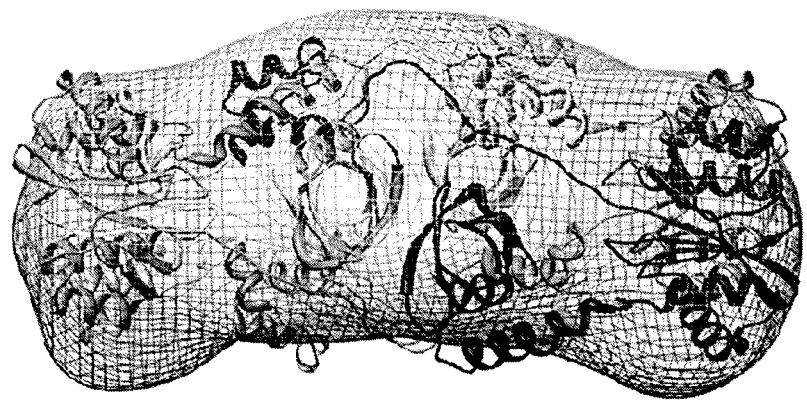
Fig. 29B

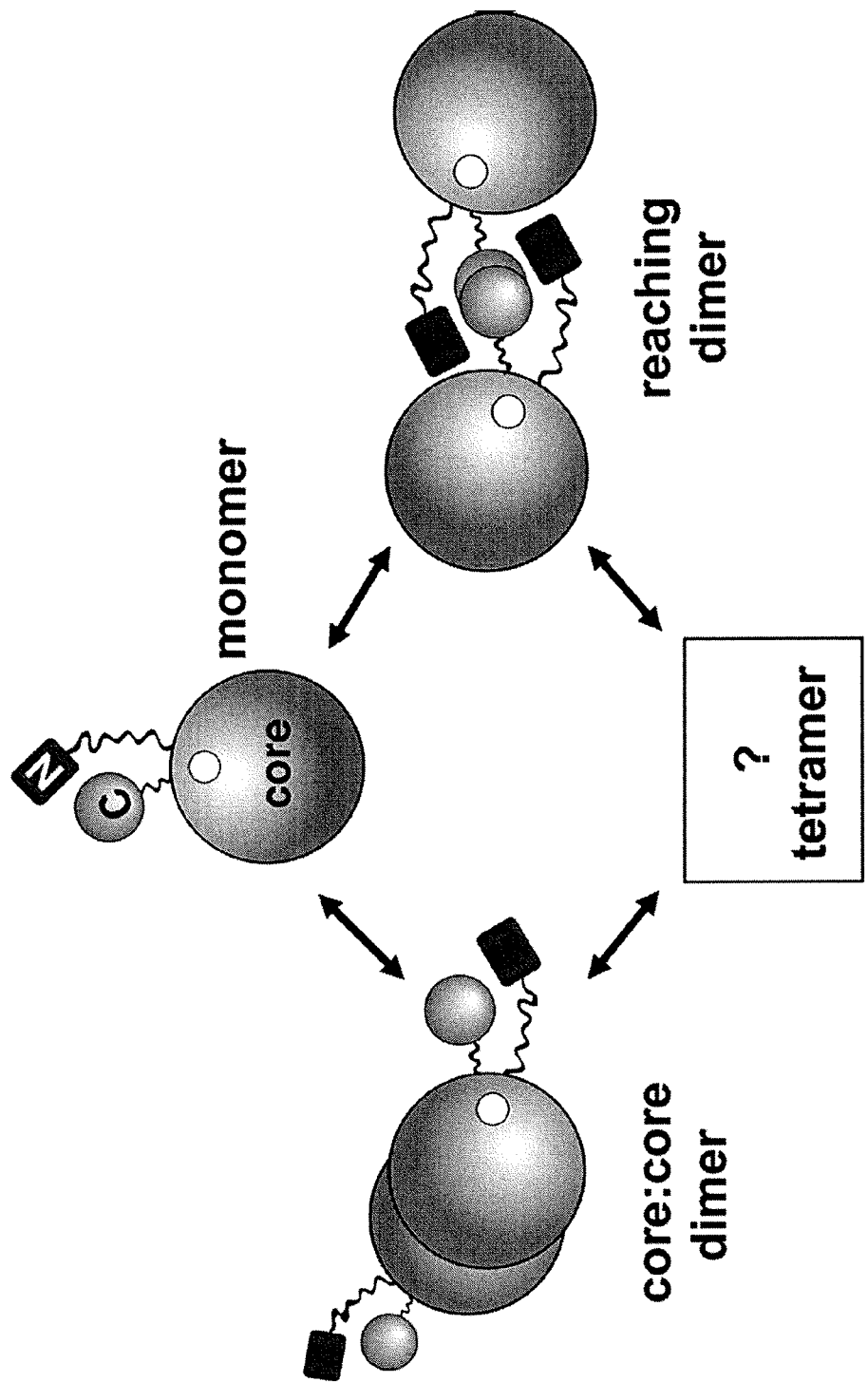

INHIBITION OF HUMAN IMMUNODEFICIENCY VIRUS INTEGRASE REACHING DIMER FORMATION UTILIZING SINGLE-CHAIN VARIABLE ANTIBODIES

CROSS REFERENCE TO RELATED APPLICATIONS

This application is a continuation in part of PCT Application No. PCT/US2011/067200, filed on Dec. 23, 2011, and claims priority to U.S. Provisional Application No. 61/426,615 filed on Dec. 23, 2010 and to U.S. Provisional Application No. 61/430,593 filed on Jan. 7, 2011. The entire contents of each application are incorporated by reference herein, in their entirety and for all purposes.

STATEMENT OF GOVERNMENT SUPPORT

The inventions described herein were made, in part, with funds obtained from the National Institutes of Health, Grant Nos. AI40385, CA71515, and CA006927. The U.S. government may have certain rights in these inventions.

REFERENCE TO A SEQUENCE LISTING

This application includes a Sequence Listing submitted electronically as a text file named Retrovirus IN Sequence Listing.txt, created on Dec. 23, 2011, with a size of 66,000 bytes. The Sequence Listing is incorporated by reference herein.

FIELD OF THE INVENTION

The invention relates generally to the field of the prevention and treatment of retroviral diseases of animals and humans. More particularly, the invention relates to methods for screening compounds for their capability to inhibit the proper multimerization of retroviral integrase proteins, or to stabilize or lock retroviral integrase multimers in a conformation or structure that inhibits the biologic activity of the retroviral integrase. The invention also relates to methods for inhibiting the capability of retroviral integrases to insert retrovirus DNA into host cell DNA.

BACKGROUND OF THE INVENTION

Various publications, including patents, published applications, technical articles and scholarly articles are cited throughout the specification. Each of these cited publications is incorporated by reference herein, in its entirety and for all purposes.

Retroviral integrase (IN) catalyzes the insertion of viral DNA into the DNA of the infected host cell. IN is one of three retroviral-encoded enzymes that are essential for retroviral replication and, therefore, is an important target for drugs to treat HIV/AIDS. Nevertheless, the inevitable development of drug resistant HIV mutants drives a continuing need for additional strategies to block the activity of this viral enzyme.

SUMMARY OF THE INVENTION

The invention features methods for inhibiting retrovirus integrase-mediated insertion of retrovirus DNA into the DNA of a host cell infected with a retrovirus. The methods generally comprise inhibiting the formation of a reaching dimer by the retrovirus integrase monomers (including dissociating a formed reaching dimer), or stabilizing a formed reaching dimer in a conformation that inhibits the capability of the reaching dimer to bind to substrate DNA in the host cell and/or inhibits the capability of the integrase to integrate viral DNA into host cell DNA. The retrovirus preferably is avian sarcoma virus or human immunodeficiency virus. Inhibiting the formation of the reaching dimer may comprises inhibiting intermolecular interactions between amino acids in the C-terminal domain of a first retrovirus integrase monomer and amino acids in the C-terminal domain of a second retrovirus integrase monomer that mediate the formation of the reaching dimer, and/or inhibiting the intermolecular interactions between amino acids in the N-terminal domain of a first retrovirus integrase monomer and amino acids in the C-terminal domain of a second retrovirus integrase monomer that mediate the formation of the reaching dimer, and/or inhibiting the intermolecular interactions between amino acids in the N-terminal domain of a first retrovirus integrase monomer and amino acids in the N-terminal domain of a second retrovirus integrase monomer that mediate the formation of the reaching dimer.

For avian sarcoma virus, the intermolecular interactions between amino acids in the C-terminal domain of the first retrovirus integrase monomer and amino acids in the C-terminal domain of the second retrovirus integrase monomer that mediate the formation of the reaching dimer may comprise one or more of the intermolecular interactions between the tryptophan at position 259 of the first retrovirus integrase monomer and the tryptophan at position 259 of the second retrovirus integrase monomer, the intermolecular interactions between the tyrosine at position 246 of the first retrovirus integrase monomer and the tyrosine at position 246 of the second retrovirus integrase monomer, and/or the intermolecular interactions between one or more of the arginine at position 244, the glycine at position 245, and the tyrosine at position 246 of the first retrovirus integrase monomer and one or more of the arginine at position 244, the glycine at position 245, and the tyrosine at position 246 of the second retrovirus integrase monomer. The intermolecular interactions between amino acids in the N-terminal domain of the first retrovirus integrase monomer and amino acids in the C-terminal domain of the second retrovirus integrase monomer that mediate the formation of the reaching dimer may comprise one or more of the intermolecular interactions between the serine at position 20 of the first retrovirus integrase monomer and the tryptophan at position 213 of the second retrovirus integrase monomer, the intermolecular interactions between the asparagine at position 24 of the first retrovirus integrase monomer and the arginine at position 214 of the second retrovirus integrase monomer, the intermolecular interactions between the serine at position 26 of the first retrovirus integrase monomer and the arginine at position 214 of the second retrovirus integrase monomer, the intermolecular interactions between the glutamine at position 28 of the first retrovirus integrase monomer and the threonine at position 216 of the second retrovirus integrase monomer, the intermolecular interactions between the arginine at position 31 of the first retrovirus integrase monomer and the arginine at position 244 of the second retrovirus integrase monomer, the intermolecular interactions between the glutamine at position 28 of the first retrovirus integrase monomer and the serine at position 262 of the second retrovirus integrase monomer, and/or the intermolecular interactions between the glutamic acid at position 32 of the first retrovirus integrase monomer and the arginine at position 263 of the second retrovirus integrase monomer. The intermolecular interactions between amino acids in the N-terminal domain of the first retrovirus integrase monomer and amino acids in the N-terminal domain of the second retrovirus integrase monomer that mediate the formation of the reaching dimer may comprise the intermolecular interactions between the asparagine at position 24 of a first retrovirus integrase monomer and the arginine at position 53 of a second retrovirus integrase monomer.

For human immunodeficiency virus, the intermolecular interactions between amino acids in the C-terminal domain of the first retrovirus integrase monomer and amino acids in the C-terminal domain of the second retrovirus integrase monomer that mediate the formation of the reaching dimer may comprise one or more of the intermolecular interactions between the tryptophan at position 243 of the first retrovirus integrase monomer and the tryptophan at position 243 or the lysine at position 244 of the second retrovirus integrase monomer, the intermolecular interactions between the lysine at position 236 of the first retrovirus integrase monomer and the glutamic acid at position 212 of the second retrovirus integrase monomer, the intermolecular interactions between the glutamic acid at position 246 of the first retrovirus integrase monomer and the lysine at position 211 of the second retrovirus integrase monomer, the intermolecular interactions between the glutamic acid at position 246 of the first retrovirus integrase monomer and the lysine at position 240 of the second retrovirus integrase monomer, the intermolecular interactions between the glutamic acid at position 246 of the first retrovirus integrase monomer and the lysine at position 264 of the second retrovirus integrase monomer, the intermolecular interactions between the lysine at position 264 of the first retrovirus integrase monomer and the aspartic acid at position 279 of the second retrovirus integrase monomer, the intermolecular interactions between the lysine at position 264 of the first retrovirus integrase monomer and the aspartic acid at position 286 of the second retrovirus integrase monomer, the intermolecular interactions between the lysine at position 264 of the first retrovirus integrase monomer and the glutamic acid at position 287 of the second retrovirus integrase monomer, the intermolecular interactions between the lysine at position 264 of the first retrovirus integrase monomer and the aspartic acid at position 288 of the second retrovirus integrase monomer, the glutamic acid at position 287 of the first retrovirus integrase monomer and the lysine at position 188 of the second retrovirus integrase monomer, and/or the glutamic acid at position 287 of the first retrovirus integrase monomer and the lysine at position 211 of the second retrovirus integrase monomer. The intermolecular interactions between amino acids in the N-terminal domain of the first retrovirus integrase monomer and amino acids in the C-terminal domain of the second retrovirus integrase monomer that mediate the formation of the reaching dimer may comprise one or more of the intermolecular interactions between the phenylalanine at position 1 of the first retrovirus integrase monomer and the aspartic acid at position 116 of the second retrovirus integrase monomer, the intermolecular interactions between the phenylalanine at position 1 of the first retrovirus integrase monomer and the glutamic acid at position 157 of the second retrovirus integrase monomer, the intermolecular interactions between the phenylalanine at position 1 of the first retrovirus integrase monomer and the glutamic acid at position 170 of the second retrovirus integrase monomer, the intermolecular interactions between the phenylalanine at position 1 of the first retrovirus integrase monomer and the glutamic acid at position 212 of the second retrovirus integrase monomer, the intermolecular interactions between the phenylalanine at position 1 of the first retrovirus integrase monomer and the aspartic acid at position 229 of the second retrovirus integrase monomer, the intermolecular interactions between the phenylalanine at position 1 of the first retrovirus integrase monomer and the glutamic acid at position 246 of the second retrovirus integrase monomer, the intermolecular interactions between the phenylalanine at position 1 of the first retrovirus integrase monomer and the glutamic acid at position 270 of the second retrovirus integrase monomer, the intermolecular interactions between the phenylalanine at position 1 of the first retrovirus integrase monomer and the aspartic acid at position 279 of the second retrovirus integrase monomer, the intermolecular interactions between the phenylalanine at position 1 of the first retrovirus integrase monomer and the glutamic acid at position 287 of the second retrovirus integrase monomer, the intermolecular interactions between the aspartic acid at position 6 of the first retrovirus integrase monomer and the lysine at position 159 of the second retrovirus integrase monomer, the intermolecular interactions between the aspartic acid at position 6 of the first retrovirus integrase monomer and the lysine at position 188 of the second retrovirus integrase monomer, the intermolecular interactions between the aspartic acid at position 6 of the first retrovirus integrase monomer and the lysine at position 215 of the second retrovirus integrase monomer, the intermolecular interactions between the glutamic acid at position 11 of the first retrovirus integrase monomer and the lysine at position 215 of the second retrovirus integrase monomer, the intermolecular interactions between the glutamic acid at position 13 of the first retrovirus integrase monomer and the lysine at position 240 of the second retrovirus integrase monomer, and/or the intermolecular interactions between the glutamic acid at position 35 of the first retrovirus integrase monomer and the lysine at position 264 of the second retrovirus integrase monomer. The intermolecular interactions between amino acids in the N-terminal domain of the first retrovirus integrase monomer and amino acids in the N-terminal domain of the second retrovirus integrase monomer that mediate the formation of the reaching dimer may comprise one or more of the intermolecular interactions between the phenylalanine at position 1 of the first retrovirus integrase monomer and the glutamic acid at position 10 of the second retrovirus integrase monomer, the intermolecular interactions between the phenylalanine at position 1 of the first retrovirus integrase monomer and the glutamic acid at position 11 of the second retrovirus integrase monomer, the intermolecular interactions between the phenylalanine at position 1 of the first retrovirus integrase monomer and the glutamic acid at position 13 of the second retrovirus integrase monomer, and/or the intermolecular interactions between the phenylalanine at position 1 of the first retrovirus integrase monomer and the glutamic acid at position 35 of the second retrovirus integrase monomer. The intermolecular interactions may comprise any interactions shown in FIG. 11B, FIG. 26B, FIG. 26C, or FIG. 26D.

The invention also features methods for treating a retrovirus infection in a subject in need thereof. The subject is preferably a human being, and the human being is preferably infected with the human immunodeficiency virus. In some aspects, the methods generally comprise administering to the subject a compound or biomolecule capable of inhibiting reaching dimer formation in an amount effective to inhibit the formation of a reaching dimer by monomers of a retrovirus integrase encoded by the infecting retrovirus. Preferably, the compound or biomolecule is administered, directly or indirectly, to a cell of the subject infected with the retrovirus such that the retrovirus DNA insertion activity of the retrovirus integrase is inhibited in the cell. The compound or biomolecule may inhibit the formation of a reaching dimer by inhibiting intermolecular interactions between amino acids in the C-terminal domain of a first retrovirus integrase monomer and amino acids in the C-terminal domain of a second retrovirus integrase monomer that mediate the formation of the reaching dimer, and/or inhibit the intermolecular interactions between amino acids in the N-terminal domain of a first retrovirus integrase monomer and amino acids in the C-terminal domain of a second retrovirus integrase monomer that mediate the formation of the reaching dimer, and/or inhibit the intermolecular interactions between amino acids in the N-terminal domain of a first retrovirus integrase monomer and amino acids in the N-terminal domain of a second retrovirus integrase monomer that mediate the formation of the reaching dimer. Such intermolecular interactions include those described in the preceding paragraphs, as well as any other interactions described or exemplified herein. In some aspects, the methods generally comprise administering to the subject a compound or biomolecule capable of reaching dimer conformation stabilization in an amount effective to stabilize a formed integrase reaching dimer of the retrovirus in a cell of the subject infected with the retrovirus in a conformation that inhibits the capability of the reaching dimer to bind to substrate DNA. The biomolecule may comprise an antibody.

BRIEF DESCRIPTION OF THE DRAWINGS

FIG. 1A-C show integrase protein domains and a core-stabilized dimer model. FIG. 1A shows a linear representation of integrase, indicating the borders of the three domains (the N-terminal domain (NTD), the catalytic core domain (CCD or core), and the C-terminal domain (CTD)), and the locations of several important residues. FIG. 1B shows ribbon models of the isolated core and CTD of avian sarcoma virus (ASV) IN are based on published data (PDB code 1C1A). The helical NTD is modeled from the HIV-1 IN domain (PDB code 1K6Y). The conserved HHCC residues, in ball-and-stick representation, bind a Zn ion (large sphere). The three conserved, active site residues in the CCD (core) are shown in ball-and-stick coordinating the metal co-factors ($Mg^{+2}$ or $Mn^{+2}$) required for catalysis (medium-sized spheres). Two additional residues of relevance to the present studies (F199 and W259) are also shown in ball-and-stick. FIG. 1C shows a core:core stabilized ASV IN dimer model.

FIG. 2A shows an experimentally-determined SAXS scattering is shown in triangles. Values calculated from the crystal structure of the same IN fragment (PDB coordinate file 1C1A) using the Crysol program are represented by a dark line. FIG. 2B shows an experimentally-derived plot of P(r) function for the SAXS data is compared with values calculated from the same crystal structure. Right: The SAXS envelope shape derived from the experimental data is portrayed as a wire mesh, and the atomic resolution coordinates of 1C1A are shown within the SAXS envelope.

FIG. 3A-C show SAXS analyses of the full-length, wild type ASV IN dimer. FIG. 3A shows experimentally-determined SAXS data, combining scattering data (data points and fit line) and P(r) function (points with error bars) into a four axis plot. FIG. 3B shows a Guinier plot of the natural log of the scattering intensity I(Q) versus Q2. A linear fit with data from 0.5/Rg to 1.2/Rg was used to approximate a radius of gyration (Rg) of 32.8 Å. FIG. 3C shows the shape of the wild type ASV IN dimer in solution, based on the SAXS data and modeled with the program GASBOR. The dimer envelope is shown in a mesh representation and two views.

FIG. 4A-E show a SAXS analyses of monomeric ASV IN proteins, and relative positioning of the terminal domains. FIG. 4A shows SAXS data obtained with the ASV IN C23S/C125S/F199K/W259A monomer. Four axis plot is as described in FIG. 3. FIG. 4B shows SAXS data obtained with the thioredoxin-ASV IN chimeric derivative, trxA-IN-C23S/C125S/F199K/W259A. FIG. 4C shows a comparison of experimentally-derived P(r) function for trxA-IN protein in panel B (squares) with two possible P(r) plots calculated from alternate arrangements of a distal NTD (light line) or distal CTD domain (dark line). FIG. 4D, Left shows the ASV IN monomer envelope indicating possible alternate arrangements of the NTD and CTD; middle shows the trxA-IN monomer envelope; right shows a ribbon model of a trxA-IN chimeric protein with the trxA domain (top domain) in a distal position from the core domain. FIG. 4E shows the envelope of the dimeric wild type ASV IN as an outer mesh representation, with two monomeric envelopes positioned to fit within the dimer envelope.

FIG. 5A-C show monomer and dimer proximities uncovered by protein cross-linking coupled with mass spectrometry. FIG. 5A shows SDS PAGE illustrating the separation of ASV multimers after cross-linking with increasing concentrations of BS3. Positions of cross-linked monomers, dimers, and tetramers, which migrate slightly faster than the non cross-linked forms, are indicated at the right of the gel. FIG. 5B shows a cross-link map of the ASV IN monomer, and a model structure. Residues involved in cross-linking between NTD and CTD in labeled wild type monomers are joined with dashed lines; solid lines identify cross-links within CTD residues or between CTD and CCD residues. Similar cross-links were observed with unlabeled monomers (not shown). Right: A HADDOCK generated monomer IN structure, using the monomer cross-linking data and the SAXS envelope derived from the W259A IN derivative. FIG. 5C shows a map of dimer cross-links between labeled and unlabeled IN subunits. CTD to CTD links are shown with solid gray lines; NTD to core or NTD to CTD links are denoted with dashed black lines.

FIG. 6A shows a summary of core:core cross-link data. Dashed lines show cross-links that were unique to protein in the tetramer band. FIG. 6B shows reciprocal interactions in the core:core dimer interface in the crystal structure of the isolated ASV domain (PDB code 1VSH) are mediated predominantly by side chains in alpha helices 1 and 5 of this domain; potential electrostatic interactions between R114' and E200, as well as H103' and E187 are highlighted; the prime designation distinguishes subunits. FIG. 6C shows single-end processing assays. Times of incubation were 5, 10, 20, and 30 min. The arrow labeled (−2) shows the position of the normal processing product. The position of the 5' $^{32}$P-labeled viral DNA end substrate is indicated by s, at the right of the gel; the control reaction in the lane marked N contained no IN protein. FIG. 6D shows a concerted integration assays. An arrowhead marks the position of a half-site reaction, in which a single end is joined to the plasmid target; the product of concerted integration is identified with an asterisk. Minutes of incubation is shown above each lane. The reaction in lane T contained no donor DNA and in the lane marked No Me²⁺, the divalent metal cofactor, Mg²⁺, was omitted. Lane M contains molecular markers and positions of the supercoiled and nicked circular forms of the target DNA are marked sc and nc, respectively.

FIG. 7A-D show a reaching dimer model of the ASV IN apo-protein. FIG. 7A shows a dimer model of ASV IN that satisfies both distance constraints from the cross-linking experiments and the envelope shape and dimensions from SAXS experiments. Two orthogonal views are shown. FIG. 7B shows a comparison of the experimentally-determined P(r) function (triangles) of dimeric wild type ASV IN, with a P(r) function calculated from the core:core stabilized dimer model shown in FIG. 1C (circles) and the reaching dimer structure in A (squares). FIG. 7C shows the details of the CTD:CTD interface in the ASV IN dimer showing how stacking between proximal W259 side chains from each CTD is a prominent feature of this interface. FIG. 7D shows a model of a reaching dimer of HIV-1 IN revealing the potential for conservation of CTD:CTD interface interactions.

FIG. 8A shows a conformation of a single ASV IN subunit in the apo-IN reaching dimer. FIG. 8B shows a conformation predicted from the inner dimer of an intasome complex that includes the viral substrate DNA. The subunit structure is modeled from the PFV intasome (PDB code 3L2T). The change in orientation of the CTD residue W259, shown in ball-and-stick, is highlighted with arrows. Active site residues are also shown in ball-and-stick fashion.

FIG. 9A shows CTD-CTD dimer linkages between labeled and unlabeled IN monomers. The insert shows a hybrid adduct corresponding to cross-linked peptide precursor ion (MW=2678.6Da) derived from the unlabeled IN sequence KVK and labeled IN sequence JVJPDITQJDEVTJJ (SEQ ID NO:1). Labeled lysines are shown as "J" and lysine residues involved in cross-linking are shown by ($1). FIG. 9B shows mass spectrometry data for NTD-core dimer linkages showing an extensive ion series for the hybrid precursor ion (MW=3328.6 Da) derived from the cross-linked peptides, with sequence U($1)HMPLR (SEQ ID NO:2) and AIJ($1)TDNGSCFTSJSTOEWLAO (SEQ ID NO:3). Cross-linked residues are shown as ($1), N-terminal glycine is shown as U, and further labeled lysine and arginine are shown as J and O respectively.

FIG. 10A-B show iterative HADDOCK docking. FIG. 10A shows statistical analysis of HADDOCK Results for the three iterative runs minimizing the RG for IN dimer formation. FIG. 10B shows the first iterative run was preformed with rigid CTD linkers and fully flexible NTD linkers, while the NTD, CTD, and core domains were allowed to be semi-flexible (i.e., secondary structural elements are preserved). From the first run, one of the minimum structures is shown as Step 1, with a unique interface mediated by tryptophan residues (W259) edge-to-edge orientation (space fill) with an estimated RG of 47. Further iterative refinement of the structure from Step 1, with constraints between interacting NTD and CTD at the interface, yielded the structure labeled Step 2, showing stacked tryptophans at the interface with a RG of 41. Finally, C2 symmetry and tighter distance constraints were imposed on the Step 2 structure to achieve the Step 3 structure with a RG of 37. The direction of the arrow represents the iterative movement of the specific domain.

FIG. 11A shows ASV IN. Hydrophobic and aromatic interactions between proximal W259 residues from each monomer are a primary stabilizing force in this reaching dimer interface. In addition, loop residues 244-246(RGY) from each monomer form direct hydrogen bonds with the other monomer. The same RGY loop residues are also involved in hydrogen bonding with the NTD of the second monomer. Backbone bonds are shown as a solid lines and side chain hydrogen bonds as dashed lines. FIG. 11B shows HIV IN. This interface can be stabilized by H-bonding of the NH group of W243 to the backbone carbonyl of K244, as well as hydrophobic interactions between W243 side chains from each monomer. In addition, the R262 side chain from one monomer, can form H-bonds with P30/V31 of the second monomer. Finally, the β-strand containing residues 257-259 from each monomer can come together in anti-parallel fashion to form a β-barrel structure comprising 3 strands from each CTD.

FIG. 12 shows the sequence of isotopically labeled wild type ASV integrase.

FIG. 15 shows a candidate binding site of another lead compound. Further in silico screening of bioactive scaffolds revealed the compound "A" as a candidate for development of novel PPIs (Protein Protein Inhibitors). Initial studies with this compound revealed 60% inhibition of HIV-IN joining activity. This compound (spacefill representation in the model) is capable of binding in a cavity between clusters 1 and 3, as shown.

FIG. 22A shows Phe-181-substituted proteins compared with wild type IN.

FIG. 23A shows intensity versus Q (A|1) at similar protein concentrations (1.6 mg/ml). FIG. 23B shows P(r) functions show distinct curves but similar $D_{max}$. FIG. 23C shows two orthogonal views of the SAXS-determined envelopes of the wild type HIV IN tetramer and the F181T and E11K dimers.

FIG. 26A shows SDS-PAGE separation of EDC cross-linked monomers, dimers, and tetramers from 1:1 mixtures of isotopically labeled HIV IN proteins and isolation of the dimer bands for mass spectrometry. (i) IN F181T at 1:1 mixtures of unlabeled and isotopically labeled protein at 25 M final concentration. EDC was added at increasing molar ratios of 5:1, 20:1, 50:1, and 100:1. The dimer band was excised from the 5:1 lane as indicated. (ii) IN F181T at a 1:1 mixture at 250 nM final concentration of the labeled and unlabeled proteins. Molar ratios of EDC were 20:1, 50:1, and 100:1, and the dimer band was excised from the 100:1 lane as indicated. (iii) HIV IN wild type protein 1:1 mixture at 450 nM final concentration of labeled and unlabeled protein. Molar ratios of EDC were 5:1, 20:1, 50:1, and 100:1. The dimers were excised from the 5:1 lane as indicated. FIG. 26B shows cross-linked residues identified by mass spectrometry analysis of EDC cross-linked dimers formed with a 25 M mixture of labeled and unlabeled IN F181T (Ai). FIG. 26C shows cross-linked residues identified by mass spectrometry analysis of EDC cross-linked dimers formed with the 250 nM mixture of labeled and unlabeled IN F181T (Aii). FIG. 26D shows cross-linked residues identified by mass spectrometry analysis of the EDC cross-linked dimers formed from a 450 nM mixture of labeled and unlabeled HIV IN wild type (Aiii). Cross-links between different domains of the labeled and unlabeled proteins are indicated with dashed lines, and cross-links between like domains are indicated by solid lines.

FIG. 27A shows a depiction of the three HADDOCK-derived models, generated by docking with distance constraints from EDC cross-links, and published intasome models sans DNA. The best-fit Model A, which includes NTD and CTD stacking interactions at the interface, is shown in two orthogonal views. The interface of this reaching dimer includes interactions between the NTD of one monomer to the NTD of the second monomer and also Trp-243:Trp-243 stacking between the subunit CTDs (spheres). Model B was derived without Trp-243 stacking, and model C was derived with inclusion of NTD to core interactions. The intasome and intasome inner dimer models are derived from the published HIV intasome model by omitting the viral DNAs.

FIG. 28A-C shows an arrangement of the HIV F181T reaching dimer and a model of the HIV E11K core-core dimer in their respective SAXS-derived envelopes. FIG. 28A (left) shows the SAXS envelope for F181T with the model A structure from FIG. 27 is shown; FIG. 28B shows P(r) plots for F181T and E11K proteins compared with those derived for the E11K model shown in A. FIG. 28C shows a plot of the scattering data obtained with the E11K protein compared with plots derived for the F181T and E11K models in 28A.

FIG. 29A-C shows inclusion of established core-core interactions to generate a likely HIV IN tetramer assembly via direct stacking of two reaching dimers. FIG. 29A shows a proposed view of core-core interactions between the two reaching dimers, which maintains a $D_{max}$ similar to that of the F181T dimer. FIG. 29B shows two orthogonal views of the tetramer model arranged inside the SAXS determined envelope of the wild type HIV IN tetramer; for clarity, each of the monomers are colored individually. FIG. 29C shows a comparison of experimental data for the wild type HIV IN tetramer with the proposed tetramer model and an intasome tetramer model without the viral DNA substrate.

FIG. 30 shows two possible HIV apoIN dimer forms. The three domains common to retroviral integrase proteins are depicted in color-coded shapes identified in the monomer as N (rectangles) for the NTD, C (small circles) for the CTD, and core (large circles) for the catalytic core domain. A small white circle symbolizes the active site in the core.

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

Figure 1A:

IN proteins are composed of three distinct structural domains (FIGS. 1A and B). The largest (amino acids 50-207 in avian sarcoma virus (ASV) IN) is the central catalytic core domain (CCD or core). This domain contains the D,D(35)E motif of acidic residues that coordinate the required divalent metal ions, $Mg^{+2}$ or $Mn^{+2}$. The isolated human immunodeficiency virus (HIV) IN core domain forms a dimer in solution, and the 3 dimensional structure of the core from several retroviral IN proteins has been solved by X-ray crystallography of either the isolated domain or two-domain fragments that include the N (NTD) or C-terminal (CTD) domains. The same extensive interface of two core domains (e.g., FIG. 1C) has been observed in every crystal structure analyzed so far and, consequently, it is believed to be physiologically relevant. The isolated, $Zn^{+2}$-binding NTD (amino acids 1-50) and the SH3-like CTD (amino acids 210-286) of HIV IN also form dimers in solution. The spatial relationships between the CTDs and cores are different in each of the two-domain crystal structures that have been determined, and the crystal structure of the NTD+core, two-domain fragment shows a different NTD:NTD interface than that observed in the NMR structure of the NTD alone.

Full-length IN proteins are known to exist as monomers, dimers, and tetramers in solution, and complementation experiments indicate that IN functions as a multimer. An IN dimer appears to be the most catalytically active form for the endonucleolytic processing of a single-end viral DNA substrate in vitro. However, as two processed DNA ends must be joined by IN to host DNA in a concerted fashion in vivo, a tetramer is assumed to be the minimal functional multimer for this step. Analysis of avian sarcoma virus (ASV) IN-DNA complexes imaged by atomic force microscopy revealed that assembly of a tetramer is induced upon interaction with a disintegration substrate, which represents a viral-host DNA integration intermediate, and that four IN monomers are required for a single catalytic turnover with this substrate (Bao, K K et al. (2003) J. Biol. Chem. 278(2), 1323-1327). Purification and analysis of covalently cross-linked multimers of HIV-1 IN showed that although a dimer could process and join a single viral DNA end substrate, only a tetramer was capable of catalyzing the concerted integration of two viral ends into a target DNA (Faure, A et al. (2005) Nucleic Acids Res. 33(3), 977-986). Analyses of in vitro assembled HIV IN synaptic complexes containing viral and target DNA substrates, also indicate that concerted integration is catalyzed by an IN tetramer (Li, M et al. (2006) Embo J. 25(6), 1295-1304).

Models for IN dimers (FIG. 1C) and tetramers have been derived from consolidation of the crystal structures of two-domain protein fragments. However, experimental knowledge has been lacking concerning the disposition of the three domains with respect to each other, in the intact full-length monomer or multimers. The crystal structure of full-length IN from the human prototype foamy virus (PFV) was recently solved in complex with viral DNA (Hare, S et al. (2010) Nature 464, 232-236) revealing two different dimer interfaces for IN within the intasome structures. In accordance with the invention, small angle X-ray scattering (SAXS) and biochemical cross-linking analyses were used to determine the structure of full-length ASV IN monomers and dimers, in the absence of DNA substrates. It was observed that the solution dimer structure is distinct from that previously proposed from analysis of two-domain crystal structures, and more closely resembles the DNA-binding inner dimer in the prototype foamy virus (PFV) intasome. Analyses of the ASV apo-IN structures highlight key domain interactions and the specific conformational changes that may occur upon DNA substrate binding.

It has been observed in accordance with the invention that mutations in ASV IN and HIV IN inhibit the formation of IN reaching dimers, and that certain conformations, structural domain arrangements or structures of an IN multimer are necessary for proper functionality (e.g., integration of viral DNA into host cell DNA) of the IN. It is believed that inhibiting the formation of retrovirus IN multimers, especially those comprising an IN reaching dimer, inhibits the capability of the IN to facilitate the insertion of retrovirus DNA into substrate (e.g., host cell) DNA. Inhibiting IN reaching dimer formation includes inhibiting the intermolecular interactions between amino acids among the NTD, CTD, and core domains of the IN that mediate the formation and/or maintenance of the reaching dimer, for example, preventing formation of a reaching dimer, and also includes dissociating a reaching dimer already formed by inhibiting the intermolecular interactions between amino acids among the NTD, CTD, and core domain of the IN that mediate the formation and/or maintenance of the reaching dimer.

It is also believed that stabilizing IN multimers, including the IN reaching dimer, in particular conformations or structures may modulate the biologic activity of the IN multimer, including inhibiting the capability of the integrase to mediate the integration of viral DNA into host cell DNA. For example, IN multimers, including a reaching dimer, in one structural arrangement may support activation of the integrase and thereby facilitate integration of viral DNA into the host cell DNA, but IN multimers, including a reaching dimer, in another structural arrangement may render the integrase inactive, and thereby inhibit integration of viral DNA into the host cell DNA.

Accordingly, the invention features methods for inhibiting the capability of retroviral integrase to insert or otherwise support or facilitate the insertion of retrovirus DNA into host cell DNA. Additionally, the invention features methods for screening compounds that are capable of inhibiting retroviral integrase multimerization, capable of dissociating retroviral integrase multimers, or capable of stabilizing retroviral integrase multimers in a structure or conformation that inhibits a biologic activity of the retroviral integrase. Any of the methods may be carried out, for example, in vitro, in vivo, ex vivo, or in situ.

In the HIV IN used in the Examples, the phenylalanine at position 1 of the IN (e.g., SEQ ID NO: 12) was changed to a glycine. It is believed that phenylalanine at position 1 will engage and react with substantially the same residues in the NTD and CTD of other IN monomers as the glycine at position 1 as used in the Examples.

In one aspect, a method for inhibiting the capability of a retrovirus to insert retrovirus DNA into host cell DNA comprises inhibiting the formation of multimers, preferably inhibiting the formation of functional multimers, and more preferably inhibiting the formation of a reaching dimer of a retroviral integrase protein in a host cell infected with the retrovirus. Inhibiting the formation of the reaching dimer may comprise inhibiting intermolecular interactions between amino acids in the C-terminal domain of a first retrovirus integrase monomer and amino acids in the C-terminal domain of a second retrovirus integrase monomer that mediate the formation of the reaching dimer, and/or inhibiting the intermolecular interactions between amino acids in the N-terminal domain of a first retrovirus integrase monomer and amino acids in the C-terminal domain of a second retrovirus integrase monomer that mediate the formation of the reaching dimer, and/or inhibiting the intermolecular interactions between amino acids in the N-terminal domain of a first retrovirus integrase monomer and amino acids in the N-terminal domain of a second retrovirus integrase monomer that mediate the formation of the reaching dimer.

Inhibiting the formation of multimers of a retroviral integrase protein may comprise contacting a host cell with an effective amount of a compound or an effective amount of a biomolecule that inhibits the formation of multimers, including the reaching dimer of the retroviral integrase protein. The multimers may comprise any combination of multimers, and preferred multimers include dimers and tetramers. A reaching dimer is highly preferred.

In some aspects the compound or the biomolecule inhibits intermolecular interactions that mediate multimerization of the retroviral integrase, for example, the intermolecular interactions between C-terminal domains of retroviral integrase monomers that facilitate multimerization, for example, that mediate formation of the reaching dimer. The compound or biomolecule may in particular inhibit intermolecular interactions between certain amino acids in the C-terminal domain of retroviral integrase monomers that mediate formation of the reaching dimer. For example, such C-terminal domain amino acids include the tryptophan at position 259 of avian sarcoma virus retroviral integrase (SEQ ID NO:4), as well as the tryptophan at position 243 of human immunodeficiency virus (SEQ ID NO:12). The compound or biomolecule may, in addition or instead, inhibit intermolecular interactions between amino acids in the C-terminal domain with amino acids in the N-terminal domain and/or amino acids in the core domain of the retroviral integrase that mediate formation of the reaching dimer. For example, such amino acids include the arginine at position 263 of HIV-1 retroviral integrase (SEQ ID NO:12), which interacts with the N-terminal domain. The compound or biomolecule may, in addition or instead, inhibit intermolecular interactions between amino acids in the core domain of the retroviral integrase, that is, intermolecular interactions between core domains of each monomer in a multimer. For example, such amino acids include the tryptophan at position 132 of HIV-1 retroviral integrase and the phenylalanine at position 181 of HIV-1 retroviral integrase. The compound may, in addition or instead, inhibit intermolecular interactions between amino acids in the core domain with amino acids in the N-terminal domain and/or amino acids in the C-terminal domain of the retroviral integrase. The compound or biomolecule preferably does not interact with, bind to, or otherwise inhibit the active site of the integrase.

The specific regions of contact between each C-terminal domain have been determined by covalently linking lysines that are within 12 Angstroms (length of the chemical linker) of each other across this interface. Several of these lysine proximity pairs were mapped to determine the conformation of the dimer interface. For example, the lysines residues involved in these cross-links include the lysine residue at position 211, the lysine residue at position 225, the lysine residue at position 266, the lysine residue at position 272, and the lysine residue at position 278 of avian sarcoma virus retroviral integrase. These proximity pairs of lysines define the dimer interface between two C-terminal domains, and many adjacent residues contribute to the stability of this reaching dimer. Thus, in some aspects, the intermolecular interactions targeted for inhibition include those occurring at the interface between C-terminal domains in retroviral integrase multimers. These intermolecular interactions may be targeted with a compound or a biomolecule according to the methods described and exemplified herein.

FIG. 11A, FIG. 11B, FIG. 19, and FIG. 26B-26D highlight the many residues that mediate formation of the reaching dimer for avian sarcoma virus and HIV-1 integrase. These residues participate in intermolecular interactions that facilitate the formation of the reaching dimer, as well as the maintenance and stability of the reaching dimer. These residues may be targeted with a compound or a biomolecule according to the methods described and exemplified herein.

Figure 13:
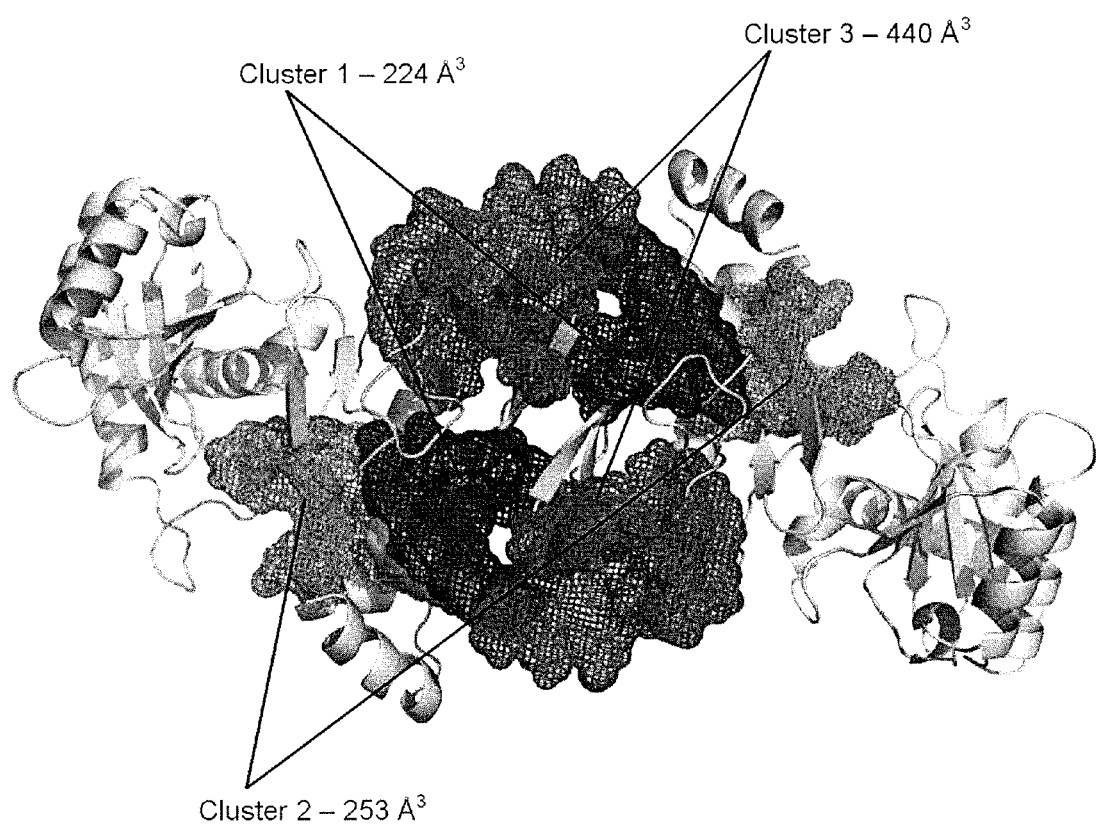
FIG. 13 shows three clusters of amino acids identified that form cavities for small molecule inhibitors of functional multimerization. The novel HIV IN dimer interface model was analyzed for presence of potential binding sites that could accommodate small molecules by QSITE program. The program revealed three clusters of amino acids that can form several binding cavities each shown in mesh representation. Generally, volumes above 200 Å3 are required for most small molecules to bind at a protein:protein interface.
Figure 14:
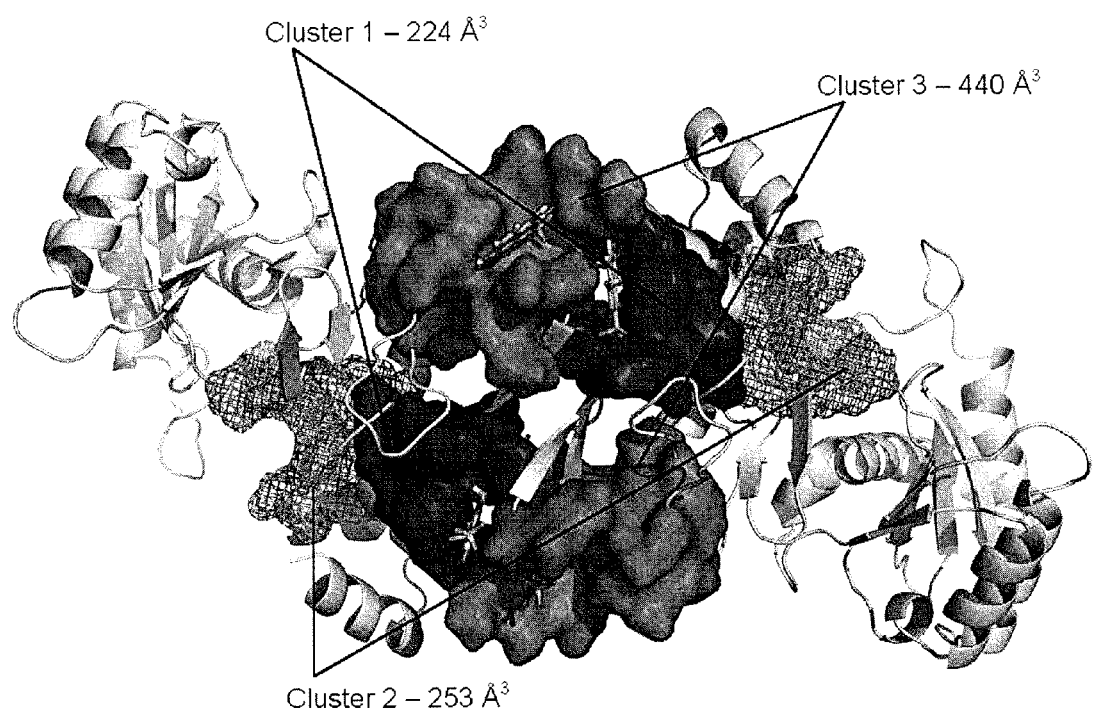
FIG. 14 shows potential binding of a known integrase inhibitor at two of the identified cluster target sites. Previous studies with an integrase inhibitor, 2BrNSA, showed robust inhibition of HIV and ASV IN, though its actual mode of interaction was not clearly understood. In silico docking the 2BrNSA revealed that it has potential to bind in several cavities formed by amino acids in cluster 1 and 3, as shown.

FIG. 13 highlights the identification of three target sites which are found in a reaching dimer. These target sites exceed the volume generally required for high affinity binding of small molecule inhibitors (see sites 1, 2 and 3 in excess of 200 Å$^3$). FIG. 14 shows the potential binding at these identified target sites by a known integrase inhibitor, 2BrNSA, active against both HIV-1 and ASV integrase. Lastly, FIG. 15 shows an example of in silico screening of inhibitor scaffolds capable of binding to these target sites uniquely found in the reaching dimer. The compound "A" shown in FIG. 15 putatively binding to sites 2 and 3 has been recently tested in a joining assay for inhibitory activity against HIV-1 integrase, and shown to result in 60% inhibition. Thus, 2BrNSA and compound A may be used as the compound that inhibits the capability of a retroviral integrase to form a reaching dimer.

For avian sarcoma virus, the intermolecular interactions between amino acids in the C-terminal domain of the first retrovirus integrase monomer and amino acids in the C-terminal domain of the second retrovirus integrase monomer that mediate the formation of the reaching dimer include one or more of the intermolecular interactions between the tryptophan at position 259 of the first retrovirus integrase monomer and the tryptophan at position 259 of the second retrovirus integrase monomer, inhibiting the intermolecular interactions between the tyrosine at position 246 of the first retrovirus integrase monomer and the tyrosine at position 246 of the second retrovirus integrase monomer, inhibiting the intermolecular interactions between one or more of the arginine at position 244, the glycine at position 245, and the tyrosine at position 246 of the first retrovirus integrase monomer and one or more of the arginine at position 244, and/or the glycine at position 245, and the tyrosine at position 246 of the second retrovirus integrase monomer. The avian sarcoma virus retrovirus integrase may comprise SEQ ID NO: 4, and the foregoing amino acid numbering may be according to SEQ ID NO: 4.

For human immunodeficiency virus, the intermolecular interactions between amino acids in the C-terminal domain of the first retrovirus integrase monomer and amino acids in the C-terminal domain of the second retrovirus integrase monomer that mediate the formation of the reaching dimer include one or more of the intermolecular interactions between the tryptophan at position 243 of the first retrovirus integrase monomer and the tryptophan at position 243 or the lysine at position 244 of the second retrovirus integrase monomer, the intermolecular interactions between the lysine at position 236 of the first retrovirus integrase monomer and the glutamic acid at position 212 of the second retrovirus integrase monomer, the intermolecular interactions between the glutamic acid at position 246 of the first retrovirus integrase monomer and the lysine at position 211 of the second retrovirus integrase monomer, the intermolecular interactions between the glutamic acid at position 246 of the first retrovirus integrase monomer and the lysine at position 240 of the second retrovirus integrase monomer, the intermolecular interactions between the glutamic acid at position 246 of the first retrovirus integrase monomer and the lysine at position 264 of the second retrovirus integrase monomer, the intermolecular interactions between the lysine at position 264 of the first retrovirus integrase monomer and the aspartic acid at position 279 of the second retrovirus integrase monomer, the intermolecular interactions between the lysine at position 264 of the first retrovirus integrase monomer and the aspartic acid at position 286 of the second retrovirus integrase monomer, the intermolecular interactions between the lysine at position 264 of the first retrovirus integrase monomer and the glutamic acid at position 287 of the second retrovirus integrase monomer, the intermolecular interactions between the lysine at position 264 of the first retrovirus integrase monomer and the aspartic acid at position 288 of the second retrovirus integrase monomer, the glutamic acid at position 287 of the first retrovirus integrase monomer and the lysine at position 188 of the second retrovirus integrase monomer, and/or the glutamic acid at position 287 of the first retrovirus integrase monomer and the lysine at position 211 of the second retrovirus integrase monomer. The human HIV integrase may comprise SEQ ID NO: 12, and the foregoing amino acid numbering may be according to SEQ ID NO: 12.

For avian sarcoma virus, the intermolecular interactions between amino acids in the N-terminal domain of the first retrovirus integrase monomer and amino acids in the C-terminal domain of the second retrovirus integrase monomer that mediate the formation of the reaching dimer include one or more of the intermolecular interactions between the serine at position 20 of the first retrovirus integrase monomer and the tryptophan at position 213 of the second retrovirus integrase monomer, the intermolecular interactions between the asparagine at position 24 of the first retrovirus integrase monomer and the arginine at position 214 of the second retrovirus integrase monomer, the intermolecular interactions between the serine at position 26 of the first retrovirus integrase monomer and the arginine at position 214 of the second retrovirus integrase monomer, the intermolecular interactions between the glutamine at position 28 of the first retrovirus integrase monomer and the threonine at position 216 of the second retrovirus integrase monomer, the intermolecular interactions between the arginine at position 31 of the first retrovirus integrase monomer and the arginine at position 244 of the second retrovirus integrase monomer, the intermolecular interactions between the glutamine at position 28 of the first retrovirus integrase monomer and the serine at position 262 of the second retrovirus integrase monomer, and/or the intermolecular interactions between the glutamic acid at position 32 of the first retrovirus integrase monomer and the arginine at position 263 of the second retrovirus integrase monomer. The avian sarcoma virus retrovirus integrase may comprise SEQ ID NO: 4, and the foregoing amino acid numbering may be according to SEQ ID NO: 4.

For human immunodeficiency virus, the intermolecular interactions between amino acids in the N-terminal domain of the first retrovirus integrase monomer and amino acids in the C-terminal domain of the second retrovirus integrase monomer that mediate the formation of the reaching dimer include one or more of the intermolecular interactions between the phenylalanine at position 1 of the first retrovirus integrase monomer and the aspartic acid at position 116 of the second retrovirus integrase monomer, the intermolecular interactions between the phenylalanine at position 1 of the first retrovirus integrase monomer and the glutamic acid at position 157 of the second retrovirus integrase monomer, the intermolecular interactions between the phenylalanine at position 1 of the first retrovirus integrase monomer and the glutamic acid at position 170 of the second retrovirus integrase monomer, the intermolecular interactions between the phenylalanine at position 1 of the first retrovirus integrase monomer and the glutamic acid at position 212 of the second retrovirus integrase monomer, the intermolecular interactions between the phenylalanine at position 1 of the first retrovirus integrase monomer and the aspartic acid at position 229 of the second retrovirus integrase monomer, the intermolecular interactions between the phenylalanine at position 1 of the first retrovirus integrase monomer and the glutamic acid at position 246 of the second retrovirus integrase monomer, the intermolecular interactions between the phenylalanine at position 1 of the first retrovirus integrase monomer and the glutamic acid at position 270 of the second retrovirus integrase monomer, the intermolecular interactions between the phenylalanine at position 1 of the first retrovirus integrase monomer and the aspartic acid at position 279 of the second retrovirus integrase monomer, the intermolecular interactions between the phenylalanine at position 1 of the first retrovirus integrase monomer and the glutamic acid at position 287 of the second retrovirus integrase monomer, the intermolecular interactions between the aspartic acid at position 6 of the first retrovirus integrase monomer and the lysine at position 159 of the second retrovirus integrase monomer, the intermolecular interactions between the aspartic acid at position 6 of the first retrovirus integrase monomer and the lysine at position 188 of the second retrovirus integrase monomer, the intermolecular interactions between the aspartic acid at position 6 of the first retrovirus integrase monomer and the lysine at position 215 of the second retrovirus integrase monomer, the intermolecular interactions between the glutamic acid at position 11 of the first retrovirus integrase monomer and the lysine at position 215 of the second retrovirus integrase monomer, the intermolecular interactions between the glutamic acid at position 13 of the first retrovirus integrase monomer and the lysine at position 240 of the second retrovirus integrase monomer, and/or the intermolecular interactions between the glutamic acid at position 35 of the first retrovirus integrase monomer and the lysine at position 264 of the second retrovirus integrase monomer. The human HIV integrase may comprise SEQ ID NO: 12, and the foregoing amino acid numbering may be according to SEQ ID NO: 12.

For avian sarcoma virus, the intermolecular interactions between amino acids in the N-terminal domain of the first retrovirus integrase monomer and amino acids in the N-terminal domain of the second retrovirus integrase monomer that mediate the formation of the reaching dimer include the intermolecular interactions between the asparagine at position 24 of a first retrovirus integrase monomer and the arginine at position 53 of a second retrovirus integrase monomer. The avian sarcoma virus retrovirus integrase may comprise SEQ ID NO: 4, and the foregoing amino acid numbering may be according to SEQ ID NO: 4.

For human immunodeficiency virus, the intermolecular interactions between amino acids in the N-terminal domain of the first retrovirus integrase monomer and amino acids in the N-terminal domain of the second retrovirus integrase monomer that mediate the formation of the reaching dimer include one or more of the intermolecular interactions between the phenylalanine at position 1 of the first retrovirus integrase monomer and the glutamic acid at position 10 of the second retrovirus integrase monomer, the intermolecular interactions between the phenylalanine at position 1 of the first retrovirus integrase monomer and the glutamic acid at position 11 of the second retrovirus integrase monomer, the intermolecular interactions between the phenylalanine at position 1 of the first retrovirus integrase monomer and the glutamic acid at position 13 of the second retrovirus integrase monomer, and/or the intermolecular interactions between the phenylalanine at position 1 of the first retrovirus integrase monomer and the glutamic acid at position 35 of the second retrovirus integrase monomer. The human HIV integrase may comprise SEQ ID NO: 12, and the foregoing amino acid numbering may be according to SEQ ID NO: 12.

The biomolecule may be a polypeptide, or may be an antibody or fragment or derivative of an antibody (e.g., scFv, VH, VL, domain antibody, Fab, and other known antibody constructs). The antibody may, for example, be mAb33 described by Ramcharan J et al. (2006) Retrovirology. 3:34; Levy-Mintz P et al. (1996) J. Virol. 70:8821-32; and Bender, D B et al. (1994) AIDS Res. Hum. Retroviruses 10:1105-1115. A single chain Fv sequence for mAb33 is provided as SEQ ID NO:194. The antibody may, for example, be mAb17 (Levy-Mintz P et al. (1996) J. Virol. 70:8821-32). A single chain Fv sequence for mAb17 is provided as SEQ ID NO:195.

In some aspects, a method for inhibiting the capability of a retrovirus to insert retrovirus DNA into host DNA comprises dissociating multimers of a retroviral integrase protein expressed in or by or otherwise present in a host cell infected with the retrovirus, for example, dissociating a formed multimer, including a formed reaching dimer. Inhibiting the formation of an integrase multimer such as a reaching dimer may comprise dissociating multimers of the integrase. Inhibiting may comprise contacting a host cell with an effective amount of a compound or biomolecule that dissociates multimers of the retroviral integrase. Dissociating may comprise reducing the multimer into monomers, or into smaller multimers, for example, tetramers into dimers, or combinations of monomers and smaller multimers. In preferred aspects, the methods comprise dissociating tetramers or dimers into monomers.

In some aspects, the compound or the biomolecule dissociates intermolecular interactions that mediate multimerization of the retroviral integrase, for example, the intermolecular interactions between C-terminal domains of retroviral integrase monomers that facilitate multimerization, including reaching dimer formation The compound or biomolecule may inhibit or dissociate intermolecular interactions between certain amino acids in the C-terminal domain of retroviral integrase monomers that facilitate multimerization. For example, such C-terminal domain amino acids include the tryptophan at position 259 of avian sarcoma virus retroviral integrase as well as the tryptophan at position 243 of human immunodeficiency virus. The compound or biomolecule may, in addition or instead, inhibit or dissociate intermolecular interactions between amino acids in the C-terminal domain with amino acids in the N-terminal domain and/or amino acids in the core domain of the retroviral integrase. For example, such amino acids include the arginine at position 263 of HIV-1 retroviral integrase, which interacts with the N-terminal domain. The compound or biomolecule may, in addition or instead, inhibit or dissociate intermolecular interactions between amino acids in the core domain of the retroviral integrase, that is, intermolecular interactions between core domains of each monomer in a multimer. For example, such amino acids include the tryptophan at position 132 of HIV-1 retroviral integrase and the phenylalanine at position 181 of HIV-1 retroviral integrase. The compound may, in addition or instead, inhibit or dissociate intermolecular interactions between amino acids in the core domain with amino acids in the N-terminal domain and/or amino acids in the C-terminal domain of the retroviral integrase. The compound or biomolecule preferably does not interact with, bind to, or otherwise inhibit the active site of the integrase.

The specific regions of contact between each C-terminal domain have been determined by covalently linking lysines that are within 12 Angstroms (length of the chemical linker) of each other across this interface. Several of these lysine proximity pairs were mapped to determine the conformation of the dimer interface. For example, the lysines residues involved in these cross-links include the lysine residue at position 211, the lysine residue at position 225, the lysine residue at position 266, the lysine residue at position 272, and the lysine residue at position 278 of avian sarcoma virus retroviral integrase. These proximity pairs of lysines define the dimer interface between two C-terminal domains, and many adjacent residues contribute to the stability of this reaching dimer. Thus, in some aspects, the intermolecular interactions targeted for inhibition include those occurring at the interface between C-terminal domains in retroviral integrase multimers. These intermolecular interactions may be targeted with a compound or a biomolecule according to the methods described and exemplified herein.

FIG. 11A, FIG. 11B, FIG. 19, and FIG. 26B-26D highlight the many residues that are involved in stabilizing the reaching dimer for avian sarcoma virus and HIV-1 integrase. These residues participate in intermolecular interactions that facilitate the formation of a reaching dimer, as well as the maintenance and stability of the reaching dimer. These residues may be targeted with a compound or a biomolecule according to the methods described and exemplified herein.

In another aspect, a method for inhibiting the capability of a retrovirus to insert retrovirus DNA into host cell DNA comprises stabilizing non-functional multimers of a retroviral integrase in a host cell infected with the retrovirus, or otherwise capable of expressing the retroviral integrase, in a conformation or structure that inhibits a biologic activity of the multimers, inhibits active multimer formation, or inhibits DNA binding. Stabilizing multimers of a retroviral integrase may comprise contacting a host cell with an effective amount of a compound or biomolecule that stabilizes multimers of the retroviral integrase in a conformation or structure that inhibits a biologic activity of competent multimers. The biologic activity of the retroviral integrase multimer preferably includes insertion of retrovirus DNA into host cell DNA, and processing of viral DNA ends, and may include other support of retrovirus infectivity. The host cell DNA may be any host DNA into which retrovirus DNA can be or is typically inserted, and host cell DNA may exist as an episomal DNA or within a chromosome, for example, any chromosome into which retrovirus DNA can be or is typically inserted. The multimers may comprise any combination of multimers. Preferred multimers include dimers and tetramers. The methods may be carried out in vitro or in vivo.

The biomolecule may be a polypeptide, or may be an antibody or fragment or derivative of an antibody (e.g., scFv, VH, VL, domain antibody, Fab, and other known antibody constructs). The antibody may, for example, be mAb33 or mAb17 or a fragment or derivative of mAb33 or mAb17.

Any of the methods described or exemplified herein may be employed to treat a retrovirus infection, or to inhibit retrovirus infectivity. For example, the methods may be employed to treat an avian sarcoma virus infection or inhibit avian sarcoma virus infectivity, or may be employed to treat a human immunodeficiency virus infection or inhibit human immunodeficiency virus infectivity, or any other retrovirus described or exemplified herein. The methods may comprise treating a retrovirus infection in a subject in need thereof, and the subject may be any animal, including any bird or mammal. Mammals are highly preferred, including companion animals, farm animals, and laboratory animals. Preferred mammals include non-human primates, and highly preferred mammals include human beings. The methods may comprise administering to a subject in need thereof a compound or antibody, including but not limited to any described or exemplified herein, in an amount effective to inhibit the formation of a reaching dimer by a retrovirus integrase such that the capability of the integrase to bind to host DNA and/or integrate viral DNA into host DNA is inhibited. The compound or biomolecule preferably inhibits the formation of a reaching dimer by inhibiting intermolecular interactions between amino acids in the C-terminal domain of a first retrovirus integrase monomer and amino acids in the C-terminal domain of a second retrovirus integrase monomer that mediate the formation of the reaching dimer, and/or inhibits the intermolecular interactions between amino acids in the N-terminal domain of a first retrovirus integrase monomer and amino acids in the C-terminal domain of a second retrovirus integrase monomer that mediate the formation of the reaching dimer, and/or inhibits the intermolecular interactions between amino acids in the N-terminal domain of a first retrovirus integrase monomer and amino acids in the N-terminal domain of a second retrovirus integrase monomer that mediate the formation of the reaching dimer. Any such amino acid interactions may comprise those described or exemplified herein.

Any of the methods described or exemplified herein may be employed to inhibit the DNA insertion capabilities of any retrovirus encoding and capable of expressing a retroviral integrase. The retrovirus may be any virus that encodes and is capable of expressing a retroviral integrase capable of forming multimers, preferably multimers formed by intermolecular interactions between or among C-terminal domains, and more preferably reaching dimers. Cancer-forming retroviruses are preferred. The retrovirus may be any of those in the genera alpharetrovirus, betaretrovirus, gammaretrovirus, deltaretrovirus, lentivirus, and spumavirus. Mammalian and avian retroviruses are preferred, and human retroviruses are more preferred. Preferred retroviruses include human T-cell leukemia virus, HTLV-1, HTLV-2, Xenotropic murine leukemia virus-related virus (XMRV), simian immunodeficiency virus, feline immunodeficiency virus, avian leukosis virus, Rous sarcoma virus, jaagsietke sheep virus, human endogenous retroviruses, mouse mammary tumor virus, simian retrovirus, bovine leukemia virus, equine infections anemia virus, maedi visma virus, feline foamy virus, bovine foamy virus, and simian foamy virus. Avian sarcoma virus and human immunodeficiency virus are highly preferred examples of retroviruses. Accordingly, in preferred aspects, the methods comprise inhibiting the formation of multimers of avian sarcoma virus integrase in a host avian cell such as a fibroblast or immune cell infected with avian sarcoma virus, or comprise inhibiting the formation of multimers of human immunodeficiency virus integrase in a host human cell infected with human immunodeficiency virus, for example, a human macrophage or T lymphocyte.

The invention also features methods for screening compounds for their capability of inhibiting the formation of multimers by a retroviral integrase. In general, a screening method comprises contacting a retroviral integrase protein with a test compound and measuring the level of multimers of the integrase protein formed in the presence of the test compound relative to the level of multimers of the integrase protein formed in the absence of the test compound. A decrease, preferably a statistically significant decrease, in the level of multimers formed in the presence of the test compound indicates that the test compound is capable of inhibiting the formation of the retroviral integrase protein multimers. Any retroviral integrase may be used in accordance with the screening method, and preferred examples of suitable retroviral integrases include avian sarcoma virus integrase and human immunodeficiency virus integrase. In preferred aspects, the retroviral integrase is free of DNA, but the retroviral integrase may be in the presence of DNA.

The screening methods are preferably carried out in vitro. The methods are capable of medium throughput screening. The methods are capable of high throughput screening.

In some aspects, the multimer is a dimer, preferably a reaching dimer. Thus, the methods comprise measuring the level of dimers, preferably reaching dimers, of the integrase protein formed in the presence of the test compound relative to the level of dimers of the integrase protein formed in the absence of the test compound. In some aspects, the multimer is a tetramer. Thus, the methods comprise measuring the level of tetramers of the integrase protein formed in the presence of the test compound relative to the level of tetramers of the integrase protein formed in the absence of the test compound.

The methods may be carried out on a retroviral integrase free of any host cells, for example, an isolated retroviral integrase. In some aspects, the methods are carried out on a retroviral integrase present in a host cell. Thus, for example, the methods may comprise contacting a host cell capable of expressing the retroviral integrase with the test compound. The host cell may be infected with a retrovirus such as avian sarcoma virus or human immunodeficiency virus such that the retrovirus introduces the retroviral integrase into the host cell. The host cell may be stably or transiently transformed with the gene encoding the retrovirus integrase protein. The host cell may be any host cell that is a natural host for the retrovirus being used, or may be a non-natural host that was infected or transfected with the retrovirus according to any means suitable in the art. The test compound may be included in a suitable carrier to facilitate entry of the test compound into the cell and/or the cell nucleus.

In parallel, a retroviral integrase or host cell infected with a retrovirus or a host cell producing a retroviral integrase may be contacted with an agent that is known to decrease retroviral integrase multimer formation in order to serve as a positive control or as a reference value for inhibiting integrase multimer formation, and/or a retroviral integrase or host cell infected with a retrovirus or host cell producing a retroviral integrase may be contacted with an agent that is known not to decrease retroviral integrase multimer formation in order to serve as a negative control for inhibiting integrase multimer formation. The positive or negative control agent may be a biomolecule, such as an antibody.

The invention also features methods for screening compounds for their capability of dissociating a multimeric retroviral integrase protein, including a reaching dimer of a retrovirus integrase. In general, a screening method comprises contacting a multimeric retroviral integrase protein with a test compound and measuring the level of monomers and/or smaller multimers (e.g., dimers produced from dissociating tetramers) of the integrase formed in the presence of the test compound relative to the level of monomers and/or smaller multimers of the integrase formed in the absence of the test compound. An increase, preferably a statistically significant increase, in the level of monomers or smaller multimers formed in the presence of the test compound indicates that the test compound is capable of dissociating the multimeric retroviral integrase. Any retroviral integrase protein may be used in accordance with the screening method, and preferred examples of suitable retroviral integrases include avian sarcoma virus integrase protein and human immunodeficiency virus integrase protein. In preferred aspects, the retroviral integrase is free of DNA, but the retroviral integrase may also be in the presence of DNA.

Such methods are preferably carried out in vitro. The methods are capable of medium throughput screening. The methods are capable of high throughput screening.

In some aspects, the multimer is a dimer, preferably a reaching dimer. Thus, the methods may comprise contacting a dimeric retroviral integrase with a test compound and measuring the level of monomers of the integrase formed in the presence of the test compound relative to the level of monomers of the integrase formed in the absence of the test compound. In some aspects, the multimer is a tetramer. Thus, the methods may comprise contacting a tetrameric retroviral integrase with a test compound and measuring the level of monomers and/or dimers of the integrase protein formed in the presence of the test compound relative to the level of monomers and/or dimers of the integrase protein formed in the absence of the test compound.

The methods may be carried out on a retroviral integrase free of any host cells, for example, an isolated retroviral integrase. In some aspects, the methods are carried out on a retroviral integrase present in a host cell. Thus, for example, the methods may comprise contacting a host cell capable of expressing the retroviral integrase with the test compound. The host cell may be infected with a retrovirus such as avian sarcoma virus or human immunodeficiency virus. The hose cell may be stably or transiently transformed with the gene encoding the retrovirus integrase. The host cell may be any host cell which is a natural host for the retrovirus being used, or may be a non-natural host that was transformed with the retrovirus according to any means suitable in the art. The test compound may be included in a suitable carrier to facilitate entry of the test compound into the cell and/or the cell nucleus.

In parallel, a retroviral integrase multimer or host cell infected with a retrovirus or host cell producing a retroviral integrase multimer may be contacted with an agent that is known to dissociate retroviral integrase multimers in order to serve as a positive control or as a reference value for dissociating retroviral integrase multimers, including a positive control or reference value for dissociating into integrase monomers or into particular smaller multimers (e.g., dimers), and/or a retroviral integrase multimer or host cell infected with a retrovirus or host cell producing a retroviral integrase multimer may be contacted with an agent that is known not to dissociate retroviral integrase multimers in order to serve as a negative control for dissociating retroviral integrase multimers. The positive or negative control agent may be a biomolecule, such as an antibody.

The invention also features methods for screening compounds for their capability of stabilizing a retroviral integrase multimer in a conformation or structure that inhibits the biologic activity of the integrase. In general, a screening method comprises contacting a retroviral integrase multimer protein with a test compound and measuring a biologic activity of the multimer in the presence of the test compound relative to a biologic activity of the multimer in the absence of the test compound. A decrease, preferably a statistically significant decrease, in a biologic activity of the multimer in the presence of the test compound indicates that the test compound is capable of stabilizing the retroviral integrase multimer in a conformation or structure that inhibits the biologic activity of the integrase. Any retroviral integrase protein may be used in accordance with the screening method, and preferred examples of suitable retroviral integrases include avian sarcoma virus integrase and human immunodeficiency virus integrase. In preferred aspects, the retroviral integrase is free of DNA, but the retroviral integrase may also be in the presence of DNA.

Such methods are preferably carried out in vitro. The methods are capable of medium throughput screening. The methods are capable of high throughput screening.

In some aspects, the methods comprise determining the conformation or structure of the multimer in the presence and absence of the test compound, and comparing the determined conformation or structure with reference values for a conformation or structure in which the retroviral integrase is biologically active and/or reference values for a conformation or structure in which the retroviral integrase is biologically inactive. Thus, the comparison with such reference values may indicate whether the test compound induces the retroviral integrase multimer to assume or stabilize in a conformation or structure that is biologically active or biologically inactive. The determining may be carried out, for example, using a processor or computer specifically programmed to determine the conformation or structure of the integrase protein, including in multimeric form. The comparing may be carried out, for example, using a processor or computer specifically programmed to compare determined conformations or structures with reference values for a conformation or structure in which the retroviral integrase is biologically active and/or a conformation or structure in which the retroviral integrase is biologically inactive.

In some aspects, the multimer is a dimer, preferably a reaching dimer. Thus, the methods comprise contacting a retroviral integrase dimer with a test compound and measuring the level of biologic activity of the dimer in the presence of the test compound relative to the level of biologic activity of the dimer in the absence of the test compound. In some aspects, the multimer is a tetramer. Thus, the methods comprise contacting a retroviral integrase tetramer with a test compound and measuring the level of biologic activity of the tetramer in the presence of the test compound relative to the level of biologic activity of the tetramer in the absence of the test compound.

The methods may be carried out on a retroviral integrase free of any host cells, for example, an isolated retroviral integrase. In some aspects, the methods are carried out on a retroviral integrase present in a host cell. Thus, for example, the methods may comprise contacting a host cell capable of expressing the retroviral integrase with the test compound. The host cell may be infected with a retrovirus such as avian sarcoma virus or human immunodeficiency virus in which the retroviral integrase normally forms functional multimers. The host cell may be transiently or stably transfected with the gene encoding the retroviral integrase. The host cell may be any host cell which is a natural host for the retrovirus being used, or may be a non-natural host that was infected or transfected with the retrovirus according to any means suitable in the art. The test compound may be included in a suitable carrier to facilitate entry of the test compound into the cell and/or the cell nucleus.

In parallel, a retroviral integrase multimer or host cell infected with a retrovirus or host cell producing a retroviral integrase multimer may be contacted with an agent that is known to stabilize the retroviral integrase multimer in a conformation or structure that inhibits the biologic activity of the integrase in order to serve as a positive control or as a reference value for stabilizing the conformation or structure of retroviral integrase multimers, and a retroviral integrase multimer or host cell infected with a retrovirus or host cell producing a retroviral integrase multimer may be contacted with an agent that is known not to stabilize the retroviral integrase multimer in a conformation or structure that inhibits the biologic activity of the integrase in order to serve as a negative control for stabilizing the conformation or structure of retroviral integrase multimers. The positive or negative control agents may be a biomolecule such as an antibody.

In any of the methods described herein, the methods may comprise comparing the measured effect, e.g., the level of integrase monomer, dimer, tetramer, or multimer formed, or the level of integrase biologic activity against reference values established for each of these effects. Thus, the measured value may be compared against reference values in addition to or instead of being compared to parallel cell cultures. It is thus contemplated that over time, databases of reference values may be compiled based on screened test compounds and screening experiments and conditions, and that such databases may be used in conjunction with the methods. Databases may include reference values already established in the art. Comparisons may be carried out, for example, using a processor or a computer specifically programmed to compare the measured effect, e.g., the level of integrase monomer, dimer, tetramer, or multimer formed, or the level of integrase biologic activity against reference values established for each of these effects.

The test compound can be contacted with a retroviral integrase or retroviral integrase multimer according to any means suitable in the art, and for any suitable period of time. The test compound can be assessed at multiple concentrations, and assessed through a time course. Combinations of test compounds may be used.

The invention also features kits to facilitate or carry out the screening methods. In some aspects, a kit for screening compounds for capability of inhibiting the formation of multimers by a retroviral integrase comprises a retroviral integrase and instructions for using the kit in a method for screening compounds for capability of inhibiting the formation of multimers by a retroviral integrase, the multimers include a reaching dimer. In some alternative aspects, the kit comprises a retrovirus capable of inducing the expression of a retroviral integrase and a host cell for the retrovirus and instructions for using the kit in a method for screening compounds for capability of inhibiting the formation of multimers, including a reaching dimer, by a retroviral integrase. The kit may optionally include a positive control compound that inhibits the formation of multimers of the retroviral integrase, and may optionally include a negative control compound that does not inhibit the formation of multimers. The positive or negative control compound may be a biomolecule such as an antibody.

In some aspects, a kit for screening compounds for capability of dissociating retroviral integrase multimers comprises a retroviral integrase multimer such as a retroviral integrase dimer or retroviral integrase tetramer and instructions for using the kit in a method for screening compounds for capability dissociating retroviral integrase multimers, including reaching dimers. In some alternative aspects, the kit comprises a retrovirus capable of inducing the expression of a retroviral integrase and a host cell for the retrovirus and instructions for using the kit in a method for screening compounds for capability of dissociating retroviral integrase multimers, including reaching dimers. The kit may optionally include a positive control compound that dissociates multimers of the retroviral integrase into monomers or smaller multimers such as dimers, and may optionally include a negative control compound that dissociates integrase multimers. The positive or negative control compound may be a biomolecule such as an antibody.

In some aspects, a kit for screening compounds for capability of stabilizing a conformation or structure of a retroviral integrase multimer comprises a retroviral integrase multimer such as a retroviral integrase dimer or retroviral integrase tetramer and instructions for using the kit in a method for screening compounds for capability of stabilizing a conformation or structure of a retroviral integrase multimer, including a reaching dimer, such that the integrase is biologically inactive. In some alternative aspects, the kit comprises a retrovirus capable of inducing the expression of a retroviral integrase and a host cell for the retrovirus and instructions for using the kit in a method for screening compounds for capability of stabilizing a conformation or structure of a retroviral integrase multimer, including a reaching dimer. The kit may optionally include a positive control compound that stabilizes a conformation or structure of a retroviral integrase multimer, and may optionally include a negative control compound that does not stabilize a conformation or structure of a retroviral integrase multimer. The positive or negative control compound may be a biomolecule such as an antibody.

In any of the inventive kits, the retroviral integrase can be avian sarcoma virus integrase and/or human immunodeficiency virus integrase. If included, the retrovirus can be avian sarcoma virus and the host cell can be an avian cell or mammalian cell. If included, the retrovirus can be human immunodeficiency virus and the host cell can be a human cell such as a human macrophage, T lymphocyte, or cell line thereof.

The following examples are provided to describe the invention in greater detail. They are intended to illustrate, not to limit, the invention.

Example 1

Experimental Procedures for Determining ASV Architecture

Light scattering analysis. Measurements were made with a Protein Solutions DynaPro Temperature Controlled Microsampler. Samples were adjusted to the desired concentration and particulates removed by filtration through a 0.2μ microcon device, and subsequent clearing by brief centrifugation at 14,000×g and 4° C. The protein concentration was then determined directly using absorbance at 280 nm and a calculated molar extinction coefficient, taking the average of 3 readings. All samples were analyzed under conditions of 10° C. in a buffer of 25 mM BisTris pH 6.1, 500 mM NaCl, 1 mM DTT, 0.1 mM EDTA, 5% glycerol. The molecular mass (MW I) was calculated from the static light scattering measurements (at least 300 acquisitions per protein sample) using the DynaPro software.

SAXS and ab initio shape modeling methods. X-ray scattering experiments were performed at the Advanced Photon Source at Argonne National Labs, 5ID-D beamline. Data were collected at 10 keV (1.24 Å) with the SAXS detector at a distance of 2.584 m and simultaneous WAXS detector at 291 cm, which produced an accessible q-range of 0.005 to 1.8 Å-1 (where $q=4\pi \sin \theta/\lambda$, where $2\theta$ is the scattering angle). To minimize protein damage, four 10 second exposures were typically taken at 10° C. with sample flowing at 4 μL/sec using a 0.3×0.3 mm2 collimated X-ray beam. Exactly matched dialysates were sampled under the same conditions to subtract from proteins samples which were tested in the range of 0.8 to 3 mg/ml in the same buffer conditions used for light scattering. Samples were filtered and cleared by centrifugation at 16,000×g just prior to placement in the sampler. While initial Rg estimates were made at APS by a linear fit of a typical Guinier plot in the q range of 0.5 to 1.2/Rg, subsequent data analysis using Irena software was used for data in the broader q range of 0.01 to 0.4 to determine Rg, I(0), as well as to calculate a paired distance distribution function (or P(r) function) and Dmax, either by Fourier transform by the method of Moore, or conventional regularization. Goodness of fit was assessed with the reduced $X^2$ parameter. In all cases, equivalent results were obtained by regularization with the program GNOM.

Subsequent ab initio shape modeling was performed with both DAMMIN and GASBOR programs, with and without P2 symmetry when appropriate. In each case, several qmax cutoff values were sampled in the range of 0.3 to 0.9, with the standard final processing using a qmax of 0.4. These produced dummy atom output files which were then used to generate the final envelopes with the Situs software.

Protein cross-linking and In-gel digestion. A mixture of 1:1, unlabeled and isotopically labeled ASV IN proteins (6.5 µM each) was equilibrated overnight and dialyzed in 20 mM HEPES (pH 7.8), 0.5M NaCl, 2 mM DTT, 10% glycerol. Freshly prepared $BS^3$ (Pierce) homo-bifunctional cross-linker was used at increasing concentrations. After addition of the cross-linker the reaction was allowed to continue at 37° C. for 5 min, and then quenched by addition of 20 µl of 2M glycine and left on ice for 30 min. The reactants were then precipitated with acetone then and resuspended in the 20 mM HEPES (pH7.8), 0.5 M NaCl, 2 mM DTT, 10% glycerol. The products were separated on a denaturing NuPAGE® (Invitrogen) 4 12% Bis Tris gel using MES running buffer and Coomassie blue stain. Monomer, dimer, and tetramer bands from a reaction in which the molar ratio of protein to BS3 was 1:20 were excised and destained (50% MeOH, 5% HOAC in water) overnight, after which they were dehydrated completely using 100% acetonitrile. Reduction and alkylation were performed by adding 20 mM dithiothreitol (DTT) and 50 mM iodoacetamide (IAA). After a second dehydration, gel bands were rehydrated at 4° C. for 45 min in trypsin solution (10 ng/µl Promega sequencing grade modified trypsin, 10 mM $NH_4HCO_3$, 10% acetonitrile). Proteins were digested overnight at 34° C.

Mass spectrometry and database searching. The digested samples were acidified with 0.3% formic acid before being injected into a LC/MS/MS instrument QSTAR (Applied Biosystems/MDS Sciex, Foster City, Calif.). An Agilent nano-HPLC (Agilent, Wilmington, Del.) was equipped to interface the Q-TOF mass spectrometer. Samples were automatically loaded onto a C-18 trap column (ZORBAX 300SB-C18, 0.3×5 mm, 5 mm) then eluted to a reversed-phase C-18 analytical column (ZORBAX 300SB-C18, 100× 150 mm, 3.5 mm). A typical HPLC gradient for the tryptic mixture of peptides was 5-80% organic solvent over a period of about 85 min, followed by 80-100% organic solvent for the next 15 min and 100-5% in the last 15 min. The 300 nl/min flow from the column elution was sprayed through a coated emitter (FS360-50-5-CE, New Objective Inc., Woburn, Calif.) into mass spectrometer with a set voltage of +2.5 kV. The system was equilibrated for 15 min at the end of the gradient. The acquisition method of QSTAR was set at a 2 s TOFMS survey scan followed by three MS/MS scans (3 s, 4 s, and 5 s, respectively). Parent ions with charge state of +2 and +3 or intensity above 15 counts were fragmented. The mass range for survey scan was 400 to 1000 amu and was 100 to 2000 amu for MS/MS scan.

The MS wiff files were processed into MGF files using Mascot Distiller with default parameters. Data were searched with MassMatrix PC suite 1.1.3 program, and search parameters were: MS accuracy, 10 ppm; MS/MS accuracy, 0.8 Da (at this level of search stringency, no peptide adducts were identified that are inconsistent with the reaching dimer); enzyme, trypsin; specificity, fully tryptic; allowed number of missed cleavages, four; fixed modifications, carbamidomethylation on cysteine. Further allowed variable modifications were K+8 for lysine; R+10 for arginine; oxidation of methionine, tryptophan, and histidine; deamidation of asparagine and glutamine. End products of BS3 mono cross-linked adducts with lysine and N-termini were allowed with water or glycine. Results of the cross-linked peptides were also manually validated using GPAMW program.

Protein Expression and Purification. Cloning, bacterial expression, and purification of ASV IN and its derivatives has been described in previous publications (Andrake M D et al. (2009) AIDS Res. The. 6:14; Merkel G et al. (2009) Methods 47: 243-248). For isotopic labeling, the IN gene was inserted into the NdeI/HindIII restriction sites of the p11 vector (Structural Genomics Consortium, University of Toronto), which contains an N-terminal His-tag with a TEV protease cleavage site. The resulting plasmid was expressed in BL21 DE3 cells that were grown in an optimized M9 medium supplemented with all unlabeled amino acids except lysine and arginine, which were replaced with 1 mM of L-Lysine (U-13C6, 97-99%; U-15N2, 97-99%) and 1 mM of L-Arginine (U-13C6, 97-99%; U-15N4) (Cambridge Isotope Laboratories, Inc). MS/MS analyses showed that the extent of incorporation of the isotopically labeled amino acids was 95% and 90% respectively (FIG. 5). The proteins were purified as described below except that before the heparin column step, the His-tag was removed with TEV protease.

Standard Protocol for ASV IN Purification. Proteins were produced and purified as described in the following typical example: A 1-liter culture of E. coli BL21(DE3) cells containing the expression plasmid is grown to an optical density of 1.0-1.2 at 600 nm. Cells were then induced by addition of IPTG to 1 mM and harvested 3 h postinduction by centrifugation at 10,000 g for 10 min 4° C. Cells were then suspended to a concentration of 6 ml/g wet cell paste in lysis buffer (50 mM BisTris pH 6.5, 1 M NaCl, 1 M Urea, 5 mM Imidazole, 5% glycerol, 6 mM 2-mercaptoethanol, and protease inhibitors; aprotinin, leupeptin, pepstatin, and phenylmethanesulfonyl fluoride (PMSF from Sigma), and lysed by two passes through a French pressure cell at 18,000 psi. The lysate was subjected to centrifugation at 15,000×g for 30 min, and the supernatant filtered (0.45 micron) prior to loading to an iminodiacetic acid (IDA)-Sepharose (Hi-Trap IDA) column charged with 50 mM $NiSO_4$ and equilibrated with lysis buffer. The column was washed with 5 column volumes of binding lysis buffer and the protein eluted with a gradient from 5 mM to 750 mM imidazole. The eluted fractions were collected into 0.4 mM EDTA (final concentration) to prevent metal induced aggregation of the protein. The salt concentration of the IDA-purified protein fractions was adjusted to 200 mM and they were applied immediately to a heparin-Sepharose column (HiTrap heparin) equilibrated in binding buffer (50 mM BisTris pH 6.5, 0.2 M NaCl, 0.1 mM EDTA, 10% glycerol, 1% Thiodiglycol, 6 mM 2-mercaptoethanol). The column was washed with 5 column volumes of binding buffer followed by a 10 column volume exponential gradient of NaCl (0.25-1.2 M) and fractions containing pure IN were pooled, concentrated on Amicon filters (YM10) and subsequently dialyzed in 25 mM BisTris pH6.1, 500 mM NaCl, 0.1 mM TCEP, 0.1 mM EDTA, 5% glycerol and stored at −70° C. As an alternate to dialysis, some preparations included a final step of size exclusion chromatography on a Superdex 200 column, followed by concentration and flash freezing in liquid nitrogen.

Assays for IN catalytic activities. Concerted integration was assayed according to methods established for HIV IN with the following modifications: final reaction conditions in a 25 or 50 microliter volume were 20 mM Hepes pH 7.5, 5 mM DDT, 10% PEG 3.35K, 20 µM ZnSO4, 30 mM MgCl2, 10 nM DNA donor, 10 µg/ml φX 174 RF I target DNA, and 80 nM ASV IN, for 1 to 2 hrs at 37° C. The reaction was stopped by adding EDTA to a final concentration of 50 mM and SDS to 0.5%, then treating with Protease K at 400 ug/ml final concentration for 60 min at 37° C. Aliquots of each reaction were run on a 0.8% Agarose gel, with a 1×TBE/1M Urea buffer at 80V for 2 hrs and stained with Syber Green.

Fitting the atomic resolution data and cross-linking results with the SAXS determined dimer envelope. Docking of the ASV integrase dimer into the SAXS determined envelope was performed by using the data-driven biomolecular docking software HADDOCK v2.0. The starting monomer IN structure for the docking was constructed from the two domain structure of ASV IN (PDB code: 1C1A) with addition of the ASV IN NTD modeled from the coordinates of the HIV 1-212 (PDB code: 1K6Y) using a fully automated protein structure homology-modeling server at SWISS-MODEL. HADDOCK was performed on the monomer structures taking all residues into consideration as well as distance constraints imposed by the chemical cross-linking data. All lysine's observed in the cross-linking were defined in the ambiguous interaction constraints (AIRs) distance tbl file with a minimum of 2.5 Å distance to a maximum of 11 Å distance between the observed hybrid adducts. The initial run was performed with rigid CTD linkers and flexible NTD linkers in the docking monomers at default parameters in expert interface. The resulting minimum structure was further refined by a final run at the Guru interface with imposed C2 symmetry on each docking monomer with the following docking parameters: Residues 1-41, 60-199, and 224-268 of the NTD, CCD, and CTD, respectively were defined as semi-flexible regions of the docking partners, while residues 42-58 and 200-223 were allowed as fully flexible motifs. During the rigid-body energy minimization, 1,000 structures were calculated with an option of cross-docking between all the randomly generated docking structures based on distance constraints. For each of the 1,000 combinations, 3 rigid-body docking trials were performed, and structures with minimum energy were further refined into 200 energy minima structures. The 200 best solutions based on the intermolecular energy were used for semiflexible simulated annealing, followed by a refinement in explicit water. Finally, the solutions were clustered by using default 7.5 Å rmsd based on the pairwise backbone rmsd matrix to the starting monomer.

Example 2

Experimental Results for Determining ASV Architecture

Figure 1B:
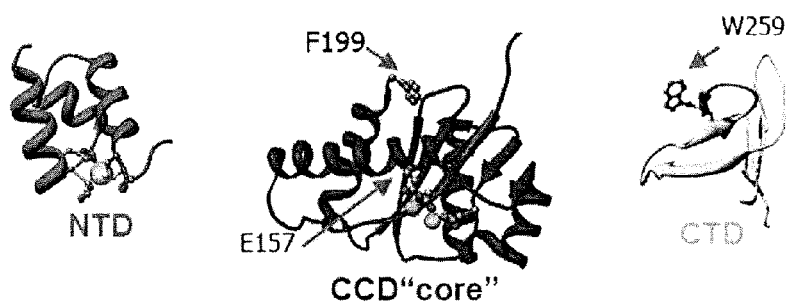

Light scattering analyses reveal homogeneous ASV IN dimers. Static light scattering provided a direct measure of the absolute molecular mass (MW-I) of the proteins and protein complexes in solution. The molecular uniformity of these preparations in the concentration range appropriate for SAXS analysis, 1 to 4 mg/ml (32 uM to 128 uM), was also evaluated by use of dynamic light scattering. As summarized in Table 1, an average molecular mass (MW I) of 69 kDa for wild type IN was obtained, only in slight excess of the calculated mass of a dimer, 64 kDa. This difference could reflect the presence of a minor amount of higher order multimers in the preparation. However, the values calculated from static light scattering can also differ somewhat from the theoretical due to the dynamic exchange of subunits in multimeric complexes. Enzymatic activity assays confirmed that this wild type protein preparation catalyzes single-end cutting and joining of viral DNA as well as concerted integration (Table 1). Among the other ASV IN derivatives prepared and analyzed, several contain an F199K substitution (FIGS. 1B and C). Structural alignments show that residue F199 in ASV IN is adjacent to that of F185 in HIV-1 IN and, as with HIV, its replacement enhances protein solubility, a feature that was required for successful crystallization of the respective two-domain IN fragments of ASV and HIV-1 IN.

To examine the effects of this substitution on ASV IN multimerization full length derivatives containing the F199K substitution alone, or in combination with other substitutions were analyzed. The MW I values observed, 71 and 72 kDa, were not appreciably different from the value for wild type IN, indicating that these preparations also contained primarily dimers under the conditions tested. These results are noteworthy, as F199 lies at the core-core interface in crystals of the isolated core domain or the core+CTD of ASV IN, and substitution of this large hydrophobic side chain is predicted to reduce the stability of this interface, as illustrated with HIV-1 IN. While the data (Table 1) show that the F199K substitution in full length ASV IN does not compromise either dimerization or single end cutting and joining of viral DNA, a role in formation of higher order IN complexes (e.g., a tetramer) is likely, as the F199K derivative is unable to catalyze concerted integration.

TABLE 1

LIGHT SCATTERING AND ACTIVITY SUMMARY

| Protein | mg/ml | MW-I kDa[e] | Apparent multimer[b] | Single-End[a] Joining | Cutting | Concerted[a] integration |
|---|---|---|---|---|---|---|
| IN(1-286) wild type | 2.3 | 69 (3.6) | Dimer [32] | +++ | +++ | +++ |
| IN(1-286) F199K | 2.5 | 71 (3.6) | Dimer [34] | +++ | +++ | − |
| IN(1-286) E157C/F199K | 2.2 | 72 (1.8) | Dimer [34] | − | − | − |
| IN(49-286) F199K | 2.0 | 54 (5.2) | Dimer [27] | +++ | +++ | − |

TABLE 1-continued

LIGHT SCATTERING AND ACTIVITY SUMMARY

| Protein | mg/ml | MW-I kDa[e] | Apparent multimer[b] | Single-End[a] Joining | Cutting | Concerted[a] integration |
|---|---|---|---|---|---|---|
| IN(1-207) | 1.5 | 28 (1.9) | Monomer [23] | +(-3)[c] | − | − |
| IN(1-286) C259/C125S/F199K/W259A | 1.0 | 34 (6.8) | Monomer [34] | +(-3) | − | − |
| IN(1-286) W259A | 2.5 | 37 (3.8) | Monomer [34] | +(-3) | − | − |
| PFV-IN(1-402) wild type | 1.0 | 57 (8.8) | Monomer [45] | N.D.[d] | +++ | +++ |

[a]Activities expressed relative to wild type.
[b]The numbers in square brackets are values for the mass of a monomer calculated from the amino acid sequence, and includes N-terminal tag residues where appropriate.
[c]Cleavage is observed at the -3 position rather than the expected -2 position. Similar -3 activity is observed with the ASV IN isolated core.
[d]ND = not tested.
[e]Molecular mass determined by static light scattering. The number in parentheses is the percent standard error (% s).

The importance of the ASV CTD for IN multimerization is illustrated by comparison of the molecular mass of IN fragments in which either the NTD or CTD is absent. The MW-I of ASV IN(49-286), which lacks the NTD is 61 kDa, more than twice the mass calculated from the amino acid sequence of a respective monomer, 27 kDa. In contrast, under comparable conditions the MW-I of the ASV IN (1-207) which lacks the CTD, is 28 kDa, a value close to the calculated monomer mass of 23 kDa.

Figure 2A:
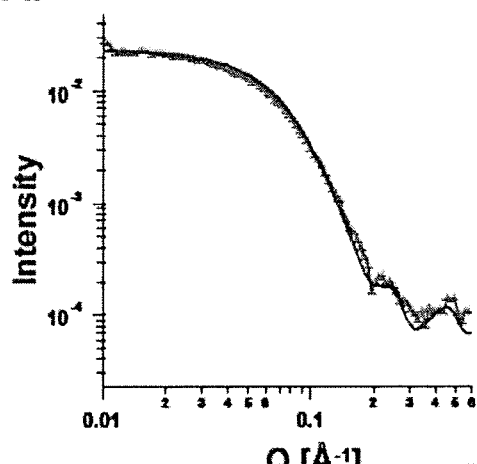
FIG. 2A-B show a comparison of the crystal structure with solution SAXS dimensions and shapes of the same NTD-lacking, two-domain ASV IN fragment [IN (49-286) F199K].
Figure 2B:
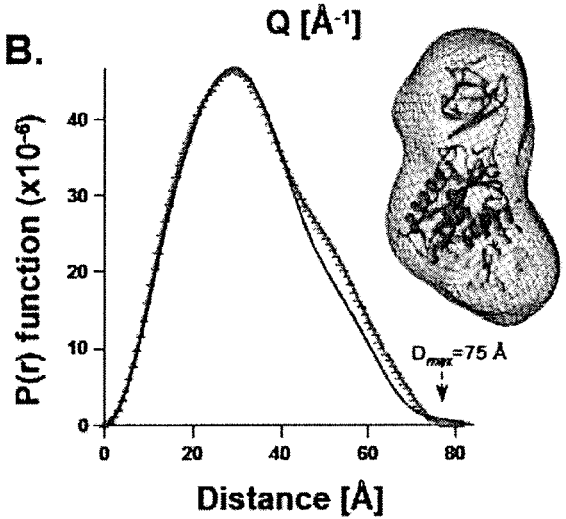

Shapes and lengths of IN proteins in solution determined by small angle X-ray scattering analysis (SAXS). SAXS analyses provide a rotationally-averaged version of the scattering of a single particle, from which size and shape can be determined. Certain features can be established unambiguously: the radius of gyration (Rg) and the longest dimension of the particle (Dmax). As verification, SAXS was performed on preparations of the two-domain fragment lacking the NTD, ASV IN (49-286) F199K, and the results were compared with the shape and size determined from the published crystal structure of the same fragment. FIG. 2 shows the light scattering data and the P(r) function for this fragment from which the Dmax was determined to be 75 Å, close to the maximum of 81 Å calculated from the coordinates of the crystal structure. A low resolution shape of the dimer was derived from the SAXS data. Computational methods were used in reverse to calculate the expected scattering and P(r) function from the published atomic coordinates of the dimer. As shown in FIG. 2, these results were nearly super imposable on the experimental data, and the SAXS-derived envelope was found to accommodate the atomic model of the crystal dimer neatly within its borders (FIG. 2B, right).

SAXS was then applied to the full-length wild type ASV IN protein, which is a homogeneous dimer at the relevant concentrations (Table 1). From the results in FIG. 3A a Dmax of 109.4 Å was established for this dimer. FIG. 3B shows a plot of the scattering intensity (I(q)) verses Q2 (a "Guinier plot") for this protein; an Rg of ~32.8 Å was calculated from the slope of a linear fit of these data in the Q·Rg<1.2 region. A similar value (Rg=33.1 Å+/−0.6) was obtained from a nonlinear regression fitting. The linearity of the data at low angles verifies that the preparation was free of aggregates.

The SAXS parameters obtained for full-length ASV IN and several other IN derivatives are summarized in Table 2. It is noted that, as with light scattering (Table 1), data obtained with the IN fragment that lacks the CTD (IN 1-207) are as expected for a monomer, confirming that important determinants of dimerization reside in the CTD of ASV IN. Therefore, while core:core interactions can facilitate dimerization of the isolated catalytic core domain under crystallization conditions, under the conditions tested herein, these interactions are not sufficient to allow dimerization of a protein that lacks the CTD. Furthermore, because a full-length derivative with an alanine substitution for residue W259 in the CTD also displays the parameters of a monomer in solution (Table 2), it is believed that this tryptophan residue plays a key role in the dimerization interface of full-length ASV IN in solution.

TABLE 2

PARAMETERS DERIVED FROM SAXS EXPERIMENTS

| Sample | Concentration (mg/mL)[a] | Q range[b] | $R_g$[c] (Å) | Dmax[c] (Å) | I(0)[c] (a.u.) | $\chi^{2f}$ |
|---|---|---|---|---|---|---|
| ASV-IN (1-286)[d] (wild type) | 2.3 | 0.007-0.4 | 33.1 ± (0.6) | 109.4 ± (1.3) | 0.033 | 0.8 |
| ASV-IN (1-286)[d, e] (E157C/F199K) | 2.4 | 0.01-0.4 | 36.8 ± (0.2) | 119.7 ± (0.8) | 0.034 | 3.4 |
| ASV-IN (1-286)[d] (C23S/C125S/F199K/W259A) | 0.7 | 0.01-0.45 | 31.5 ± (0.2) | 92.8 ± (1.5) | 0.024 | 1.7 |
| trxA-ASV-IN (1-286)[d] (C23S/C125S/F199K/W259A) | 1.4 | 0.01-0.4 | 39.3 ± (0.4) | 114.9 ± (1.3) | 0.030 | 1.1 |
| ASV-IN (49-286)[d, e] (F199K) | 1.1 | 0.01-0.42 | 26.0 ± (0.8) | 75.0 ± (2.2) | 0.022 | 2.2 |
| ASV-IN (1-207)[d, e] | 3.6 | 0.01-0.41 | 20.0 ± (0.1) | 61.0 ± (0.4) | 0.011 | 0.8 |

TABLE 2-continued

PARAMETERS DERIVED FROM SAXS EXPERIMENTS

| Sample | Concentration (mg/mL)[a] | Q range[b] | $R_g$[c] (Å) | Dmax[c] (Å) | I(0)[c] (a.u.) | $\chi^{2f}$ |
|---|---|---|---|---|---|---|
| PFV-IN (1-402)[d] (wild type) | 4.3 | 0.007-0.42 | 38.5 ± (0.2) | 117.9 ± (0.6) | 0.031 | 2.7 |

[a]As determined by absorbance at 280 nm with concentration determined with a calculated molar extinction coefficient (MEC) at $A_{280}$.
[b]$Q = 4\pi \sin\theta/\lambda$, where $2\theta$ is the scattering angle; recorded data in this range was used for P(r) analysis and subsequent ab initio shape reconstructions.
[c]As determined using the program IRENA. Comparable results were obtained. using the program GNOM, and by Guinier analysis with auto $R_g$.
[d]Data was collected at APS beamline DND-CAT 5ID-D.
[e]Data was also collected at local source.
[f]Goodness of fit as assessed by reduced chi squared analysis.

The SAXS-determined shape of monomeric IN establishes constraints for the relative arrangement of the three domains. In order to determine how the subunits and their respective domains could be arranged within the experimentally determined IN dimer envelope, SAXS analysis was performed on a full length ASV IN derivative that includes the W259A substitution. This protein contained three additional substitutions (C23S/C125S/F199K) that improve solubility, but have no affect on single-end cutting or joining activity (data not shown). The data obtained with this monomer (FIG. 4A), and its predicted elongated shape (FIG. 4D), are consistent with a structure containing the IN core domain (at the base in the Fig.) and the two smaller terminal domains, one close and one distal to the core. To determine if the distal domain corresponds to the NTD or CTD, a chimeric protein was produced in which thioredoxin (trxA) is fused to the NTD of the W259A derivative (trxA-IN-W259A). The SAXS parameters for this derivative are summarized in Table 2, and the scattering data are shown in FIG. 4B. The envelope derived for the chimeric protein is considerably longer than that of the monomer lacking the N-terminal trxA domain, consistent with a distal placement for the NTD (FIG. 4D). Furthermore the theoretical curve for a structure in which the CTD of this derivative is the distal domain, produces parameters and an envelope that are inconsistent with the data in FIG. 4B (FIG. 4C). It is believed that the distal domain in the ASV IN monomer is the NTD. A provisional model consistent with this conclusion is shown to the right of the trxA ASV-IN envelope in FIG. 4D. This model is also supported by results from SAXS analysis of wild type PFV IN, which contains a natural N-terminal extension called NED, and is a monomer under the conditions of analysis; like the chimeric protein, the PFV monomer is longer than the ASV IN monomer (Table 2) with a shape consistent with an NTD extension (envelope not shown). FIG. 4E shows how two monomer envelopes of ASV IN might fit within the dimeric envelope of wild type ASV IN with the approximate positions of each domain noted.

Strategy for identifying amino acid proximities in the IN monomer and multimers. To identify their regions of proximity within a dimer, it is necessary to be able to distinguish the two subunits. To do so, wild type ASV IN protein that was isotopically labeled with 13C and 15N in lysine and arginine residues was prepared, FIG. 12, SEQ ID NO:4. The doubly-labeled IN was then equilibrated with an equal amount of unlabeled IN. After equilibration, half of the dimers are expected to be mixed dimers, containing one labeled and one unlabeled monomer, and the remainder either fully labeled or fully unlabeled. The mixture was then treated with Bis(sulphosuccinimidyl) suberate (BS3), a reagent that forms covalent cross-links between primary amines in lysine side chains and also with protein N-termini, that lie within 11.4 Å of each other. Samples were then subjected to electrophoresis in a denaturing polyacrylamide gel to determine the optimal concentration of BS3 (FIG. 5A). Cross-linked monomer, dimer, and tetramer bands were excised from the 1:20 lane, and the proteins eluted for identification of intra- and inter-subunit cross-links respectively, using trypsin digestion followed by mass spectrometry.

Proximities determined from analysis of cross-linked monomeric IN. MS/MS analysis of protein excised from the monomer band, which contained both labeled and unlabeled IN protein, showed extensive intra-protein cross-linking (FIG. 5B). However, no peptides corresponding to chemical cross-linking between the labeled and unlabeled IN proteins were detected in the isolated monomers. Demonstrating the uniform accessibility of side chains by this methodology, 15 of the total 20 surface accessible lysine residues in all three domains of IN, as well as the N-termini were found to be mono-modified by the BS3, with dead ends comprising glycine or water. As summarized in FIG. 5B, 5 of the 10 lysine residues in the CTD are within ~11 Å of lysines in the NTD and the core; CTD tail residue K278 was cross-linked to NTD G1, and residues in the core domain, K116 and K191 were cross-linked to CTD K264. In the CTD linker region, residues K211 and K225 were cross-linked to K266 and K272 respectively (FIG. 5B), consistent with the SH3 like fold of the CTD.

A monomer structure of IN that satisfies the observed cross-link constraints would place the NTD close to the C-terminal tail region of the CTD. In addition, the observed cross-links between lysine residues in the CTD with those in the NTD and core domains places the CTD in a position proximal to both. A structure consistent with all of the cross-linking data (FIG. 5B, right) has an extended NTD, which points away from the core domain, and a CTD in the cleft between the NTD-core-linker region. This independently-derived arrangement is consistent with the SAXS data summarized in FIG. 4.

Figure 9A:
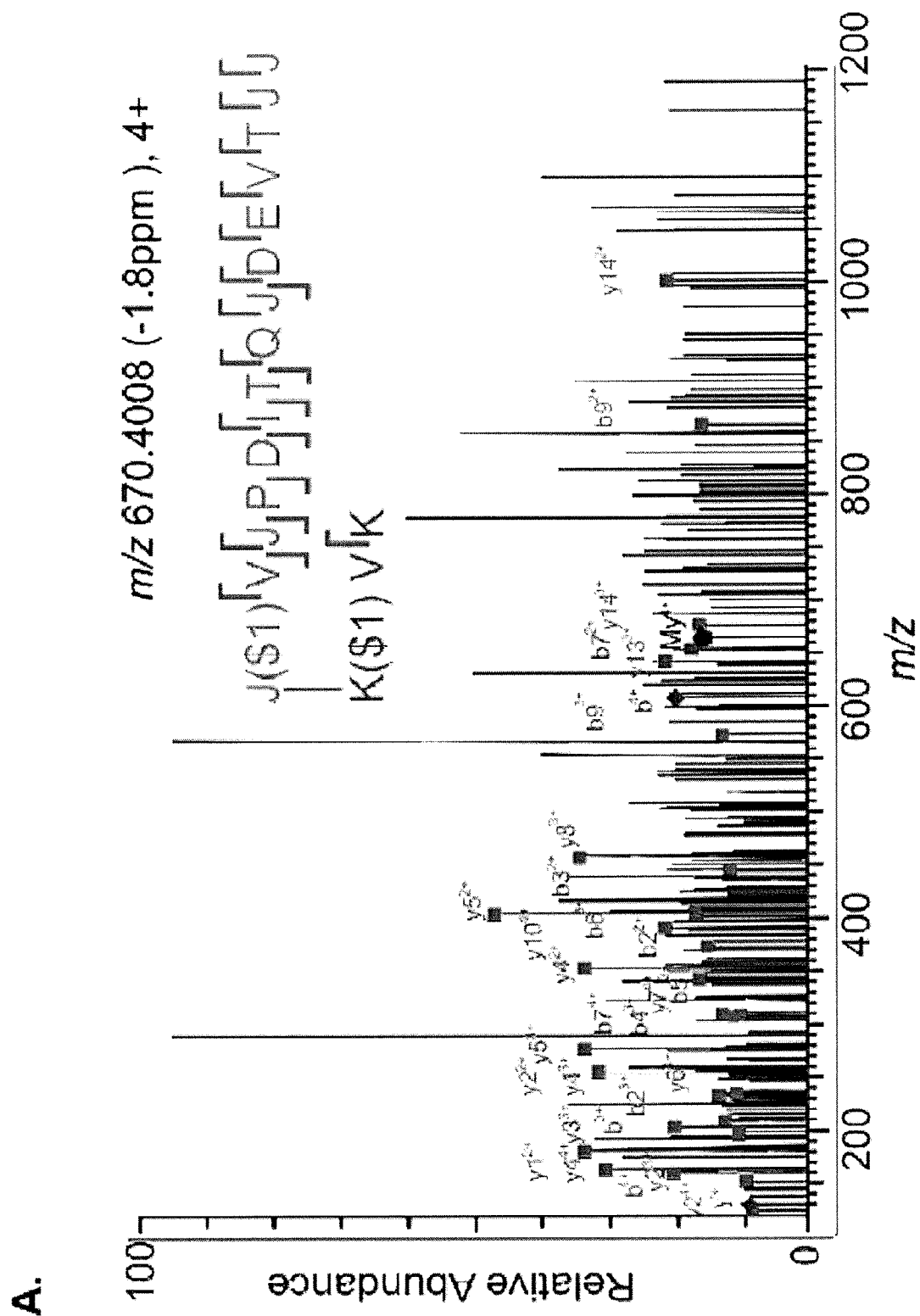
FIG. 9A-B show representative mass spectrometry data.
Figure 9B:
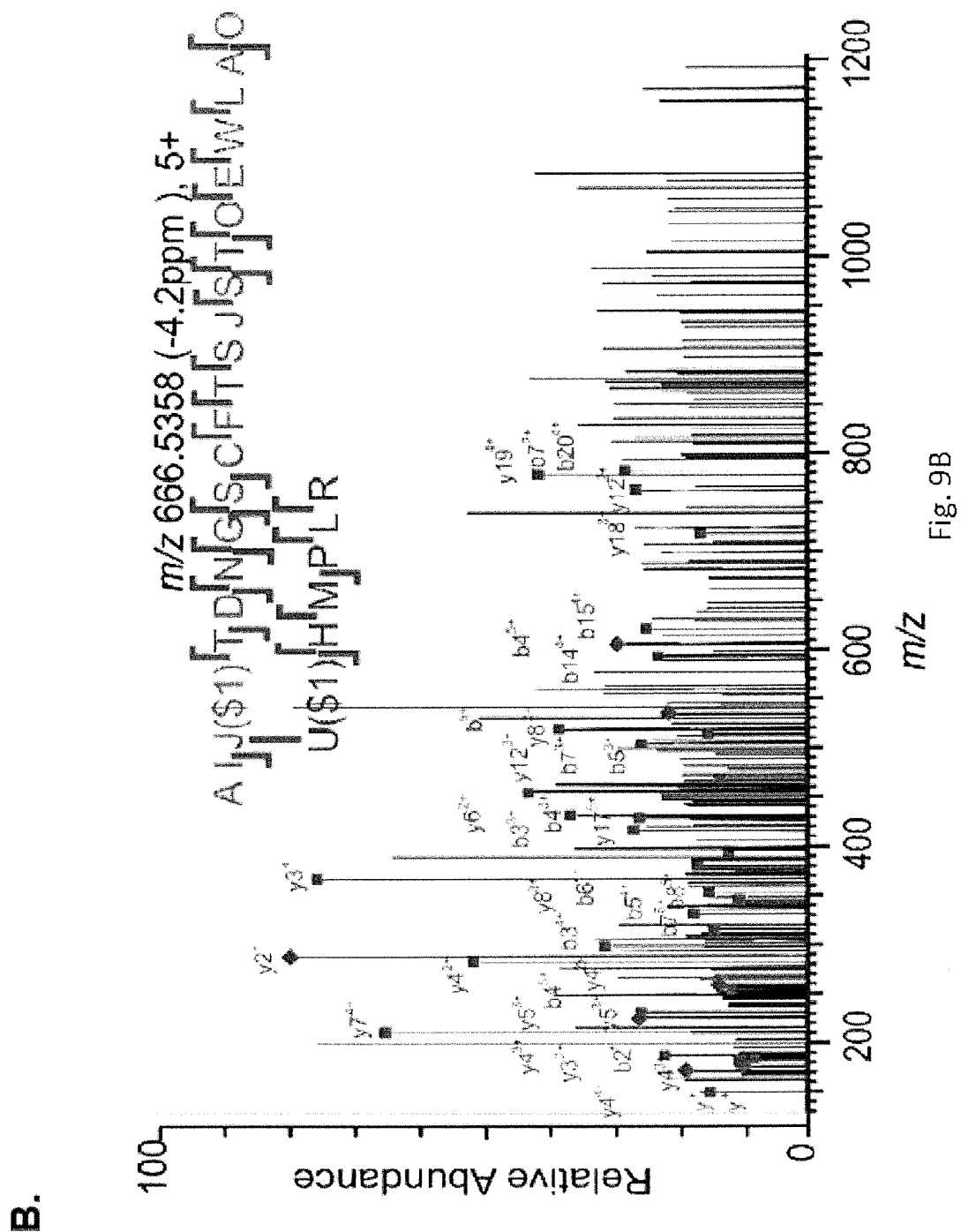

Identification of inter-subunit proximities in the IN dimer. Protein excised from the cross-linked dimer band was then analyzed. In this sample, inter-subunit proximities in mixed dimers can be identified unambiguously by mass spectrometry owing to the hybrid mass of cross-linked peptides. Results from analysis of such peptides revealed an extensive network of interactions with a total of 21 cross-links between lysine residues in all domains of both subunits (FIG. 5C). For example, NTD residue K6 in the unlabeled IN monomer cross-linked with core domain K116 in the labeled IN, and NTD K21 in the unlabeled subunit formed cross-links with K166 in the core and the CTD K264. In addition, the amino group of the N-terminal glycine in the labeled IN subunit formed cross-links with core domain residues K116 and K164, and CTD residues K264, K266 and K278 near the base of the tail in the unlabeled subunit. Reciprocal cross-links were identified between the core domain residue K164 in the unlabeled subunit to the N-terminal G1 and CTD residue K264 in the labeled subunit. At least 5 lysine residues in the CTD of the unlabeled IN were found to cross-link with 6 residues in the labeled IN, the identified cross-link adduct pairs were: K211:K264, K264:K6, K264:G1, K264:K264, K164:K264, K21:K278, K21:K166, K6:K116 and K266:K264 respectively. Representative mass spectrometry data from the analysis of cross-linked peptides with hybrid mass are shown in FIG. 9. In summary, a total of 16 unique cross-links were uncovered, of which 8 of the 20 lysine residues in the unlabeled IN subunit formed cross-links with lysines in the labeled IN subunit, and 7 of the 20 lysine residues in the labeled IN subunit formed cross-links with unlabeled IN subunit (FIG. 5C). The failure to identify completely reciprocal adducts could be due to incomplete detection, or to minor asymmetry of interactions between the dimer interfaces, perhaps reflecting some flexibility in the subunit domains. With greater than 95% sequence coverage, we favor the latter interpretation.

The proximity data obtained from the analyses of cross-linked IN monomers and dimers support a dimer model that includes the following notable features: a) In the dimer interface, CTD domains from each monomer come into close enough contact (i.e., ≤11 Å) to form the following cross-links: K264:K211, K264:K264, K264:K266, and others not included in FIG. 5C. b) No cross-links between the two core domains were detected in the dimer. Consequently, the position of this domain in each subunit is sufficiently remote to exclude such interaction. As no cross-links were observed between NTDs in the mixed dimers, a similar constraint applies to this domain. c) The NTD from one subunit is sufficiently close to the core domain and CTD of the other subunit to permit the following cross-link interactions between the subunits: G1:K116, G1:K164, G1:K264, K116:K6, K166:K21, and K264:K21.

The features delineated above are uniformly inconsistent with the core:core dimer model proposed from the two-domain crystal structures. The full length dimer structure deduced from the results is stabilized by CTD:CTD interactions between both subunits and by interactions of the NTD of one IN subunit with the core domain and the CTD of the second subunit.

Figures 6A, 6B, 6C, 6D:
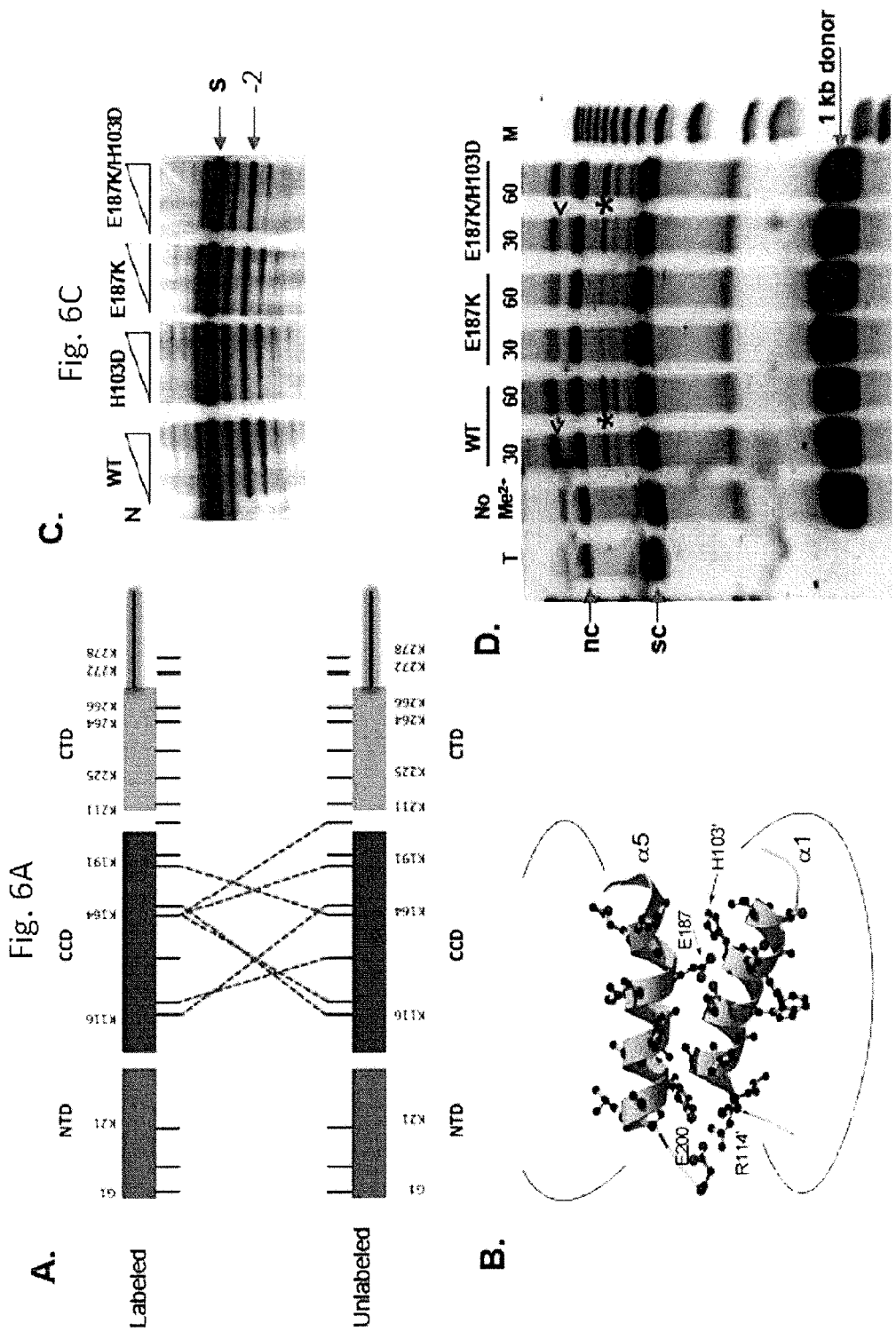
FIG. 6A-D show cross-linking evidence for core-core interactions in tetramers and their functional relevance.
Figure 8A:
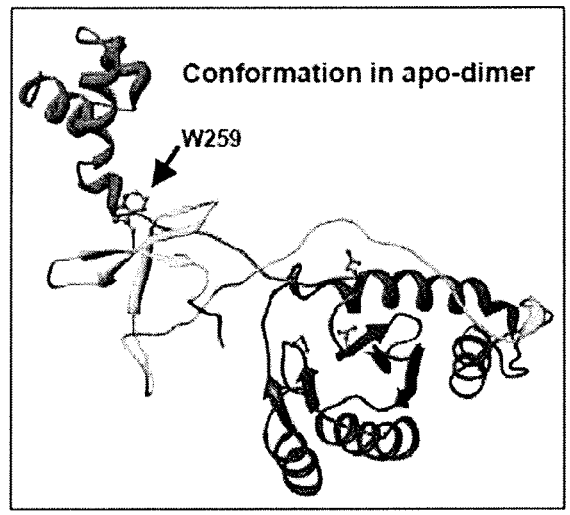
FIG. 8A-B show the conformational change required for the transition from a reaching dimer to the intasome complex with DNA.
Figure 8B:
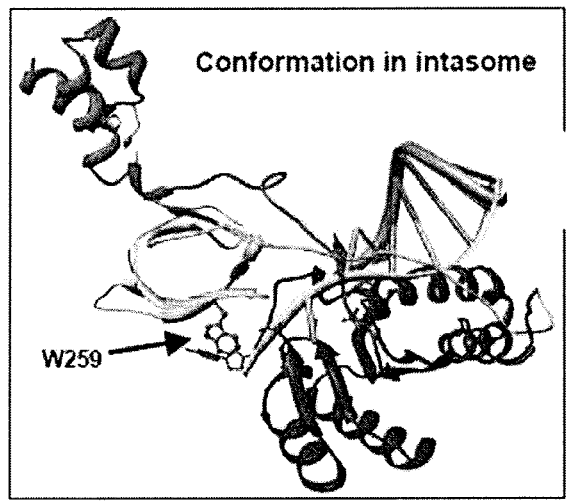

Identification of core-core interactions in the IN tetramer. MS/MS analysis of protein from the IN tetramer band (FIG. 5) revealed core:core cross-links in addition to the novel cross-links identified in protein from the dimer band. Cross-links were observed with 5 of the 7 lysine residues in this domain, of which reciprocal adducts of K164:K184 were observed between the labeled and unlabeled subunits (FIG. 6A). The remaining cross-links between these subunits were: K116:K166, K119:K164, K129:K116, K164:K116 and K211:K164. These interactions are consistent with the interface observed in the crystal structure of the isolated ASV IN core domain and the core+CTD two domain structure.

As illustrated in FIG. 6B, reciprocal interactions in the core:core dimer interface of ASV IN are mediated predominantly by side chains from alpha helices 1 and 5; potential electrostatic interactions between R114 and E200, and H103 and E187 are highlighted. To investigate the functional importance of these interactions, charge-reversing single substitutions, E187K and H103D, and a compensatory double substitution, E187K/H103D, were made. Comparison of the single-end processing activity as a function of time showed no significant differences; each derivative was capable of −2 cleavage (FIG. 6C). In contrast, an assay for concerted integration activity showed that the protein with a single substitution, E187K, is defective in this reaction (FIG. 6D; lanes 5 and 6). However, this function is restored in the derivative with the compensatory substitutions, which exhibits activity similar to that of the wild type protein (FIG. 6D, lanes 7 and 8). It is believed that stability of a core:core interface, which is detected only in the cross-linked tetramers, is required for concerted integration but not single-end processing.

Figure 10B:
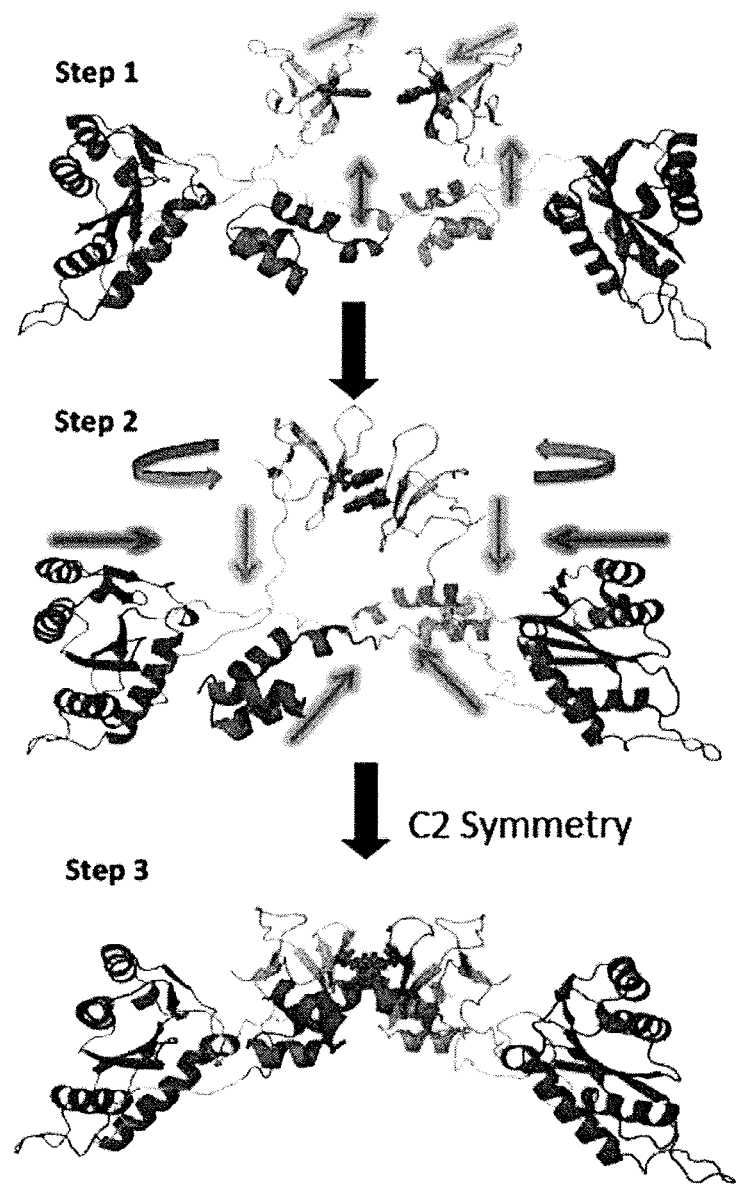

The ASV IN solution dimer structure derived via data-driven docking. To gain detailed insight into the architecture of the IN dimer, the employed the HADDOCK 2.0 docking program was used with distance constraints established by the cross-linking data (FIG. 5C). These data-driven runs were performed on superimposed monomers constructed from the coordinates of the ASV core+CTD crystal structure (1C1A) and HIV core+NTD crystal structure (1K6Y) maintaining a minimum distance of 2.5 Å to a maximum reach of 11 Å between the defined cross-linked lysines across both monomers. Iterative runs were performed until Rg's from the docked structures were in close approximation to the experimentally-determined SAXS envelope (FIG. 10). Rigid body fitting of these models within the SAXS envelope was performed by steepest descent local optimization which converges on an orientation that minimizes the number of atoms lying outside the envelope. The resulting minimized symmetrical structure, shown in FIG. 7A, is stabilized by face-to-face hydrophobic interaction between W259 from each of the monomers.

FIG. 7B shows the P(r) function derived from the SAXS analysis of the wild type ASV IN dimer and theoretical curves calculated from the core-stabilized dimer model (FIG. 1C) and the reaching dimer structure (FIG. 7A). This comparison shows that the core-stabilized dimer structure possesses a significantly shorter Dmax, and is less elongated and more spherical in shape than that deduced from the experimental SAXS data. The theoretical curve for the reaching dimer matches the experimental data more closely, and shows the same Dmax. These results, together with the observation that the IN W259A derivative behaves as a monomer, are consistent with a subunit arrangement in which the CTDs, rather than the core domains, play a critical role in dimerization. FIG. 7C shows a close-up view of CTD interactions in the reaching dimer, including stacking of the W259 residues.

A reaching dimer model for HIV 1 IN. Although sequence identity between ASV and HIV IN proteins is less than 20%, they have very similar domain architecture. Consequently, a reaching dimer model for HIV IN, based on the ASV IN structure, was constructed to uncover any conserved features and evaluate the correlation with previous mutagenesis data. A comparison of the two reaching dimers shows that the CTD interfaces of both can be stabilized by face-to-face interactions between aromatic residues: W259 residues as described above for ASV IN, and W243 residues for HIV 1 (FIGS. 7C and 7D). As noted in Table 2, replacement of W259 with alanine, abolishes both dimer formation by ASV IN and proper cleavage at the minus 2 position relative to the 3'OH ends in the viral DNA substrates. The comparable substitution in HIV IN (W243A) also results in the loss of single-end processing activity, as would be expected if W243 played a similar role in HIV 1 IN.

Figure 11A:
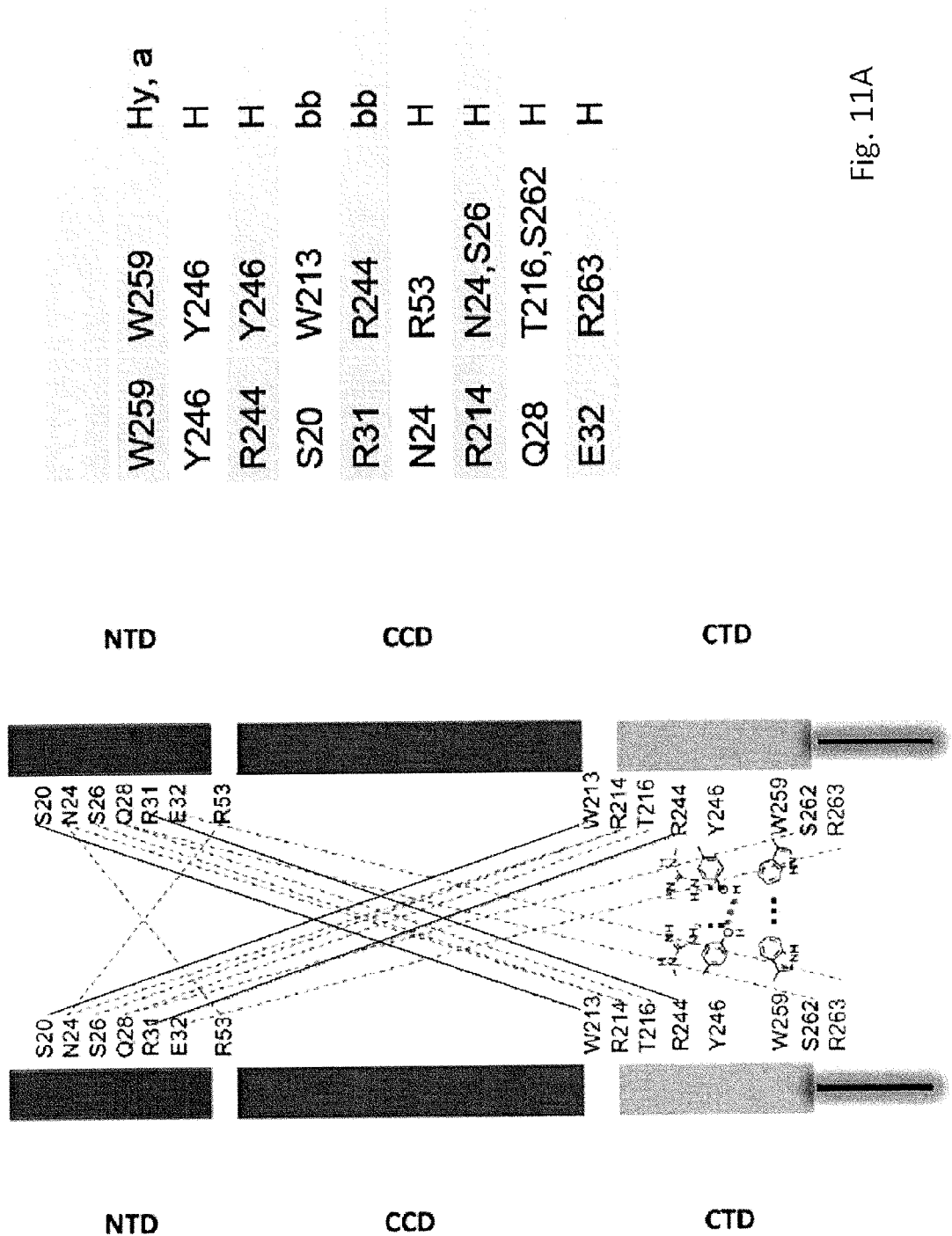
FIG. 11A-B show stabilizing interactions in ASV and HIV-1 IN reaching dimers.
Figure 11B:
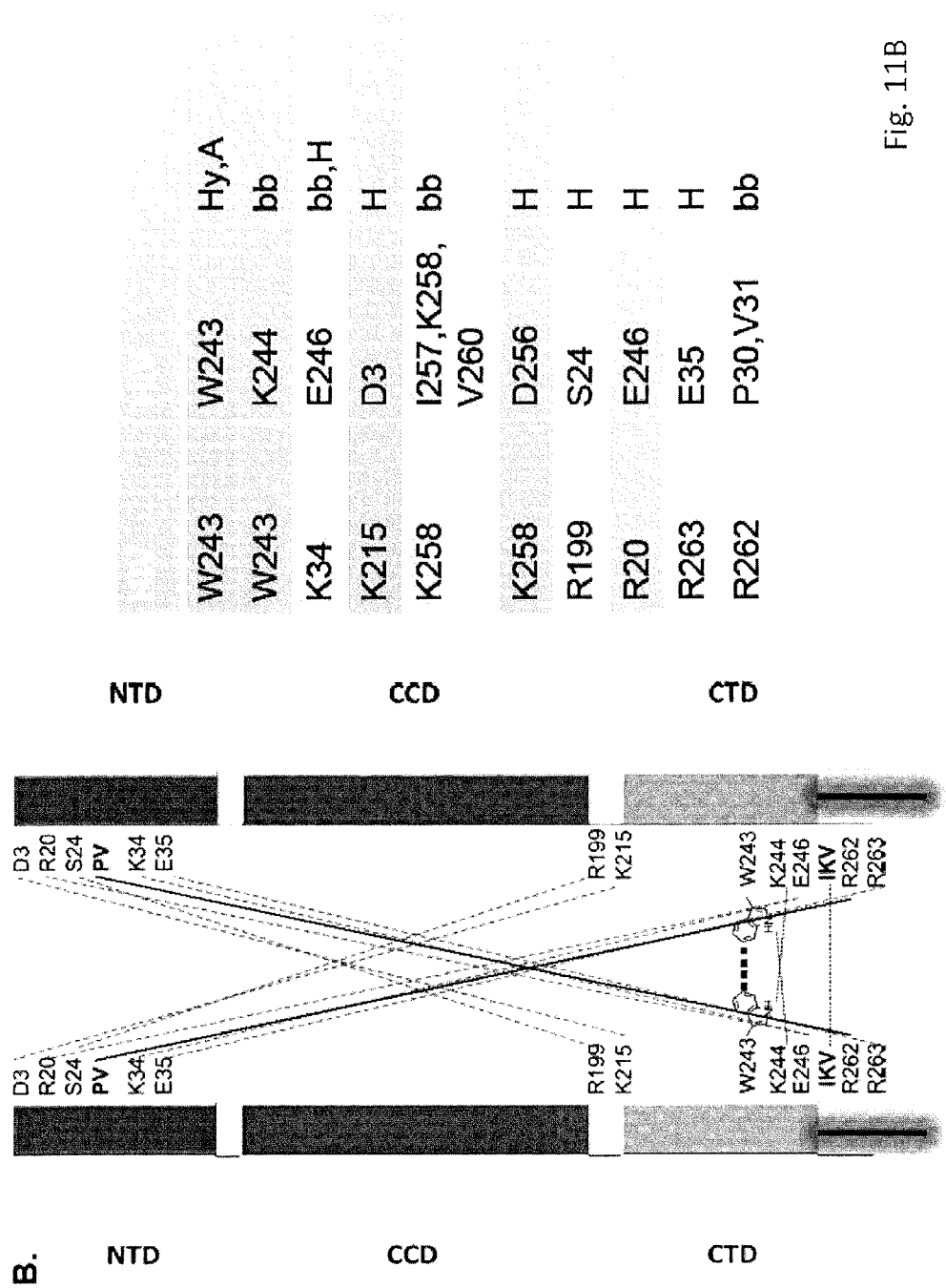

Further inspection of the reaching dimer interfaces of ASV IN and HIV 1 IN reveals a network of potential hydrogen bonds between the NTD from one monomer to both of the linkers and the CTD in the second monomer (FIG. 11). With ASV IN, it was observed that interruption of the proposed hydrogen bonding between N24 and R53 in the linker region (FIG. 11A) by replacement of the latter residue with alanine, resulted in loss of single-end joining activity (data not shown). Potential interactions between the CTD from one monomer with the CTD and NTD in the second monomer, include buried hydrophobic interactions involving W259 in ASV IN and W243 in the HIV IN. In the ASV IN structure, side chains from residues 244-246, can stabilize the dimer interface further through formation of intermolecular hydrogen bonds between the two tyrosine side chains (FIG. 11A). It was observed that substitution of alanine for Y246 results in a 50% decrease in single-end joining activity (data not shown). These results are consistent with a role for such hydrogen bonds in the architecture of a functional dimer. The potential hydrogen bond interactions in the proposed reaching dimer interface of HIV IN (FIG. 11B) includes residues that are highly conserved in the HIV genome, with less than 1% variance observed in the genomes of viruses isolated from 488 inhibitor-naïve patients in a recent study (Ceccherini-Silberstein, F et al. (2009) AIDS Rev. 11(1) 17-29). Such conservation would be expected from stringent evolutionary pressure for assembly of a functional form of the apoenzyme.

Example 3

Summary of ASV Architecture Experiments

It is believed that the foregoing are the first, experimentally-derived full length apo-protein solution structures of IN to be reported. Although relatively low resolution, the use of SAXS with wild type IN and IN derivatives provided valuable insight into the length, shape, and domain organizations in full length monomers and dimers. Protein cross-linking which tethers all dynamically involved intra- and inter-facial lysines separated by ≤11 Å, coupled with mass spectrometry, provided independent constraints for docking within the SAXS-derived envelopes. After equilibrating an equal mixture of unlabeled and labeled IN proteins, intermolecular cross-links could be identified unambiguously by the isolation of adducts with hybrid mass. As no hybrid adducts were observed in the analyses of cross-linked monomers isolated from the mixture, it is believed that the native structure was conserved within the cross-linked proteins.

In the IN monomers, the CTD was found to cross-link with the core and the NTD, and the NTD with the CTD "tail" (residues 270-289). A model for the full length IN monomer structure that combines the SAXS and cross-linking data (FIG. 5B) shows the core and NTDs at distal poles and the NTD in close proximity to the extended tail of the centrally located CTD. The solution dimer structure revealed in these studies is noteworthy for the absence of any core:core domain interactions, which had previously been thought to stabilize this multimeric form. Analysis of the cross-linked dimers uncovered a cluster of hybrid adducts formed between two IN monomers. The unanticipated architecture so revealed shows a reciprocal arrangement in which the CTD from one monomer anchors into the CTD of the second monomer, and the NTD from one monomer interacts with core and CTD of the second monomer. The absence of any core:core and NTD:NTD cross-links between the subunits implies that these domains are distantly separated in the two subunits. A model consistent with results from the SAXS and cross-linking studies places the two core domains at opposite ends, with the association of subunits stabilized by interactions between opposing NTDs and CTDs, which reach out to each other (FIG. 4E and FIG. 7A).

Cross-links corresponding to the core:core interface observed in crystals of the isolated core and two-domain fragments were detected only in full-length ASV IN tetramers (FIG. 6A). Results from the mutational studies suggest that the stability of this interface is required for concerted integration, but it is not essential for catalysis of single-end processing or joining by IN, which can be accomplished by IN dimers. Consequently, it is believed that the primary role of the core:core interface is in assembly of a tetrameric synaptic complex, which can catalyze the concerted joining of two 3' viral DNA ends into a target DNA.

A detailed structural model of the reaching dimer of ASV IN was obtained by combining the observed chemical cross-linking distance constraints with data-driven docking (FIG. 7A and FIG. 10). In the iterative docking runs, the protein-protein buried surface area increased from 1100 Å2 to 2200 Å2, while Rg was reduced from 47 to 34 in the final minimum structure. Increase in the buried surface area and decrease in Rg implies a structure that is considerably more compact that the sum of the initial docking monomers.

The interface in the reaching dimer is dominated by aromatic interactions between a cluster of residues in the CTDs, which represent a unique hot spot for the maintenance of dimer stability. Results from the mutational studies indicate that the tryptophan residues, W259 in ASV IN and W243 in HIV IN, play a role in both the catalytic activity and stability of an intersubunit interface (Table 2, FIG. 5).

Example 4

Preparation and Analysis of Monomers, Dimers, and Tetramers of HIV Integrase Using SAXS The findings described in Examples 1-3 have allowed the construction of a similar model for an HIV integrase (IN) reaching dimer (FIG. 7D), for its stability, which enables the prediction of the dynamic changes that must occur to accommodate viral DNA binding. It was hypothesized that HIV W243 is likely to play a similar pivotal role as ASV W259, as it has been shown that a non-conservative substitution (W243A) renders the protein unable to catalyze processing or joining.

From comparison of the core:core dimer and reaching dimer interfaces, different stabilities can be predicted for HIV, ASV, and PFV IN proteins. Whereas ASV IN has an extensive array of stabilizing reaching dimer interactions, PFV IN does not and in the absence of DNA the PFV protein is mostly monomeric even at relatively high concentrations. Conversely, core:core interactions in HIV IN are predicted to be significantly stronger than ASV IN, and it has been observed that at concentrations at which ASV apo-IN is a dimer, HIV apo-IN is a tetramer (FIG. 16A).

Figures 16A, 16B:
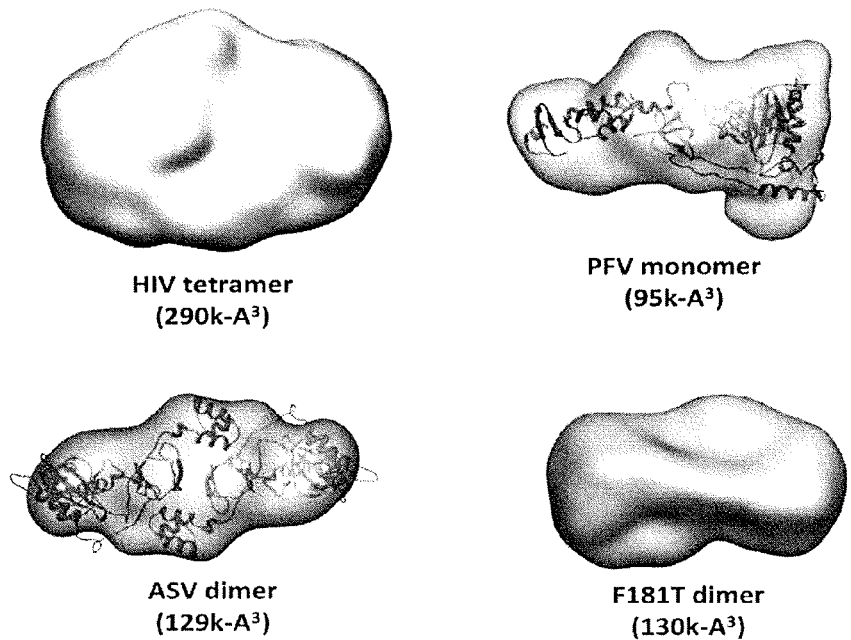
FIG. 16A shows sizes and multimers formed for various IN proteins. SAXS scattering data were processed with the program IRENA to determine the radius of gyration (Rg) and the maximum length of the scattering multimer Dmax. Situs and Chimera softwares were then used to determine the volume of the resulting SAXS envelope.
FIG. 16B shows SAXS-determined shapes and proteins from FIG. 16A.

Buffer conditions have been defined in which unliganded wild type HIV IN is soluble at concentrations that are suitable for SAXS analysis (FIG. 16A), and efforts have been initiated to determine the dimensions and shape of HIV-1 apo-IN monomers, dimers, and tetramers in solution (FIG. 16B). Disruption of core:core interactions in HIV IN block tetramer, but not dimer formation, and substitution of the conserved, stabilizing aromatic residues in this interface result in substantial loss of single end joining, but not 3'-end processing activity.

HIV IN derivatives containing threonine substitutions in two of these residues have been prepared. Although one, W132T, is insoluble, analysis of the second, F181T, revealed that this protein is soluble, and is in the form of a dimer at the same concentration that the wild type protein is a tetramer (FIG. 16A). The rate of joining by the F181T derivative is 5% that of wild type HIV IN, and the rate of 3' processing is 24% of wild type. These values are comparable to the (−; 0-10%) and (++; 40 80%) for F181G, given variations in assay methods.

SAXS analyses revealed distinct Pr curves for HIV apo-IN monomers, dimers, and tetramers. However, similar $D_{max}$ values were obtained for the wild type ASV IN dimer, and both the wild type HIV IN tetramer and the F181T dimer. It is believed that the larger volume of the HIV IN tetramer can be explained by a structure comprising two stacked reaching dimers that are stabilized by core-core interactions. The SAXS results for PFV IN are consistent with a monomer that can accommodate the atomic structure determined by X-ray crystallography.

Figure 17:
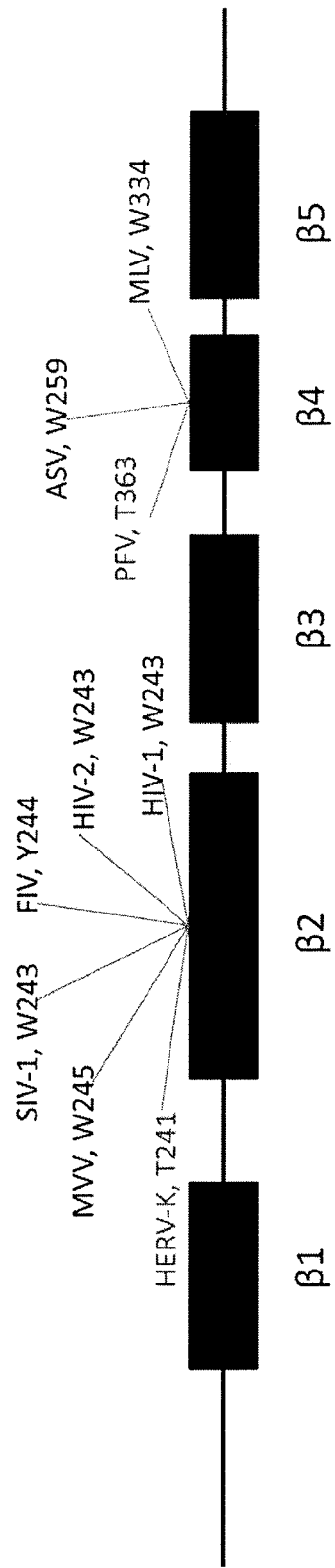
FIG. 17 shows the location of hotspots for IN CTD:CTD interactions in different retroviral proteins.
Figure 18:
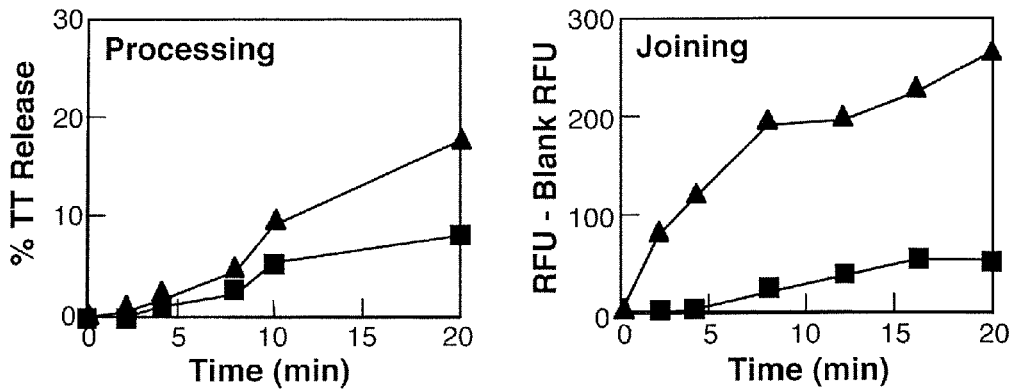
FIG. 18 shows enzymatic activities of HIV IN and the W243T derivative. ♦=wild type HIV IN; ▲=IN(W243T).

From the model of an HIV IN reaching dimer (FIG. 7D), it is predicted that tryptophan 243 is critical for its stability. Comparisons with PFV IN, (FIG. 16A and FIG. 17), suggest that substitution of non aromatic amino acids for this residue will reduce the stability of reaching dimers (in the absence of DNA), but will not affect formation of core:core stabilized dimers. As shown in FIG. 18, an HIV IN W243T derivative retains 58% of the 3' processing activity and 8% of the single-end joining activity of the wild type protein, approximately twice the values (25% and 5%, respectively) that were previously reported for the W243A protein, using similar sensitive, kinetic assays. This result is consistent with the PFV crystal structure, which shows that a threonine at the analogous position facilitates intasome formation via interactions of these CTD residues in the "inner" dimer with the uncleaved viral DNA strands. However, the HIV IN W243T derivative has no detectable concerted integration activity, suggesting that in HIV IN this residue has an additional role, which may be exerted in a tetramer.

The homogeneity and multimeric states of the substituted HIV IN proteins will be determined by dynamic light scattering, and their catalytic activities will be monitored by standard methods. As it has been verified that the F181T derivative assembles primarily into dimers, a CTD:CTD-disrupting substitution will be introduced into this derivative (e.g., in L241, L242, or W243) to render it monomeric, and then it will be determined if such full-length monomers can bind or process viral DNA. After evaluation of the homogeneity of the proposed HIV IN derivatives and, if necessary, introduction of additional solubility-promoting substitutions, the sizes and shapes of the monomers and multimer forms will be determined by SAXS. Because previous work revealed that metal cofactors can affect HIV IN conformation and viral DNA binding/end fraying, these structural analyses will compare results in the absence and presence of $Zn^{+2}$, $Mg^{+2}$, or $Mn^{+2}$.

Example 5

Determining Inter-Molecular Proximities in HIV IN Dimers and Tetramers Using Chemical Cross-Linking Coupled with Mass Spectrometry To distinguish between intra- and inter-subunit interactions in HIV IN dimer assemblies the approach used in the studies with ASV IN, above, will be employed. Briefly, each of the substituted IN proteins will be expressed in bacteria grown in minimal medium supplemented with $^{13}C$ and $^{15}N$ labeled lysine and arginine (Cambridge Isotopes Inc). The isotopically-labeled proteins are required for identification of hybrid peptide adducts by mass spectrometry. To evaluate amino acid proximities and inter-domain distances predicted from the shapes and sizes generated from SAXS analysis of the proposed HIV IN reaching dimers and core:core dimers, chemical cross-linking ($BS^3$ or EDC) will be employed with 1:1 mixtures of labeled and unlabeled IN under conditions in which hybrid dimers are formed.

The cross linked proteins will be separated by SDS electrophoresis (as in FIG. 5A) and after proteolytic digestion, the peptides will be analyzed by mass spectrometry. Peptides derived from inter-subunit cross-links will be identified by their hybrid mass. The distance constraints established from the cross-linking results will be combined with the SAXS data and in silico docking (e.g., the program HADDOCK, de Vires S J et al. (2010) Nature Protocols 5:883-97) to determine the architecture of the full-length HIV dimers in solution.

Figure 19:
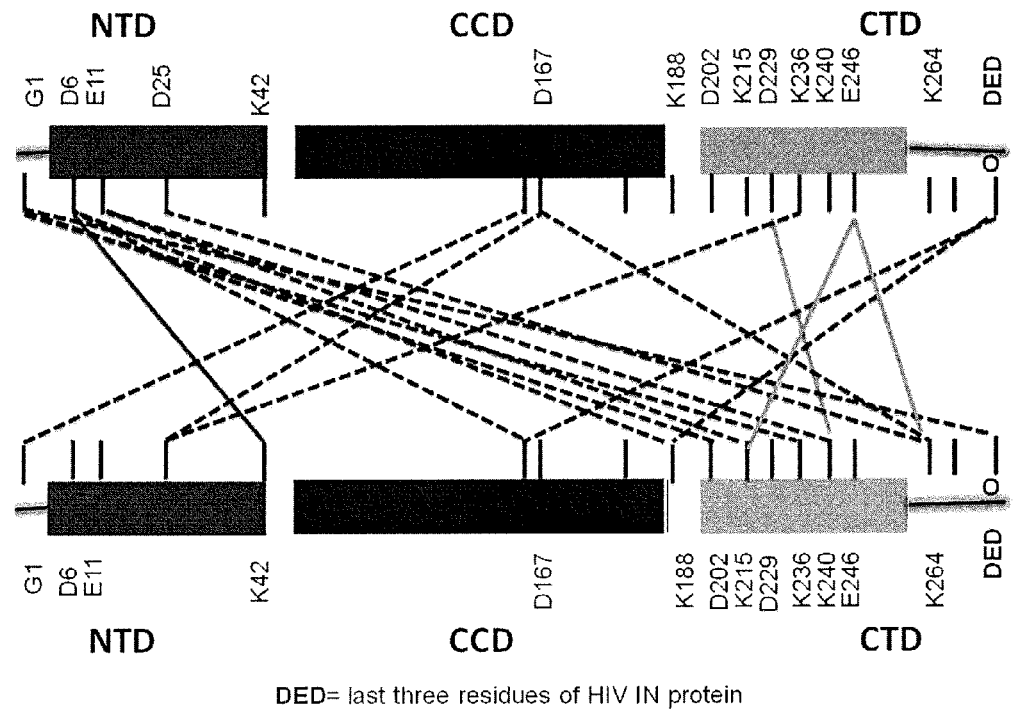
FIG. 19 shows a map of the dimer cross-links between unlabeled and labeled HIV F181T IN subunits. NTD to NTD cross-link is shown by a solid black line, CTD to CTD cross-links are shown by solid gray lines, amd inter-domain cross-links are denoted by dashed black lines.

As with the ASV reaching dimer, results from preliminary analyses have revealed two major classes of intermolecular contacts in protein excised from the cross-linked wild type HIV IN dimer (formed at low concentration) and the F181T derivative: namely, links from NTD to either the CCD or CTD residues, and links from CTD to CTD residues (FIG. 19). Although a comprehensive mapping of all contacts will be required to perform in silico docking, these data, together with the SAXS analyses, confirm the existence of reaching dimer architectures for both wild type and F181T HIV IN proteins. Once the mapping of contacts has been completed, the process of constructing and further testing both the HIV apo-IN reaching dimer and tetramer models will begin.

Example 6

Evaluating the DNA-Binding and Catalytic Properties of HIV IN Core:Core Dimers and Reaching Dimers The characterized substituted HIV IN proteins that form primarily core:core or reaching dimers, will be tested both for viral DNA binding and catalytic activity. As a control, an S119D substitution will be introduced in the target DNA binding site to eliminate interactions of the viral DNA substrates at this site. Time resolved fluorescence anisotropy will be used to determine the stoichiometry of particular IN-DNA complexes. It is predicted that some HIV IN derivatives that can form reaching dimers but cannot make stable core-core interactions, will perform the processing reaction but not the concerted integration of two viral ends into a target host DNA.

It will be determined whether addition of IN derivatives that can only make core:core dimers will restore concerted integration activity. Such restoration would be consistent with the notion that the additional "outer" subunits can contribute to tetramer formation and the structural determinants required for concerted integration. Standard procedures will be used to assay for DNA binding, processing, joining, and concerted integration. If the roles of the two dimeric interfaces in HIV IN mirror what has been described for ASV IN, it is predicted that substitutions that compromise the reaching dimer interface will affect both processing and joining, whereas substitutions that target the core:core dimer interface will primarily affect concerted integration.

These alternate dimer preparations will also allow the determination of the association constants for each dimer type, and may suggest the mode of assembly for HIV IN dimers and tetramers that is relevant to function.

To obtain a more detailed understanding of the dynamic changes that occur in the absence and presence of a viral DNA substrate, a single-molecule, Förster-type resonance energy transfer (FRET) experiments will be conducted. Initial experiments, will look for the CTD rotation predicted to occur in a reaching dimer (FIG. 17).

a His-tagged HIV IN reaching dimer (e.g., the IN F181T derivative) will be prepared in which all accessible cysteine residues have been substituted with serines, but which includes a single cysteine substitution at a solvent-accessible position in the CTD. A second preparation will include a single cysteine substitution in the NTD, but no His-tag. Experiments will verify that these substitutions do not compromise viral DNA binding and processing.

The cysteine in one preparation will then be labeled with a FRET donor and the cysteine in the other with a FRET acceptor. A mixture of these two preparations will be allowed to exchange and equilibrate in high salt before being affixed onto slides via the His-tag. Only mixed dimers will produce a FRET signal. As FRET changes can be measured in milliseconds with these methods, the normal molecular fluctuations that involve these two domains in solution will be detected. Changes in FRET signal that occur upon addition of viral DNA in reduced salt concentration will then be monitored.

It is predicted that DNA binding will stabilize a rotated CTD acceptor, at a position further removed from the NTD donor, which can be measured. It may be necessary to test several possible labeling positions to find a combination for which enzymatic activity is retained and the dyes are at a favorable distance. However, success with this strategy in preliminary experiments with NTD(C23)- and CTD (V257C)-labled ASV IN derivatives and with the HIV derivatives described in Example 7 below, indicate that this approach is feasible. The capabilities of this system will allow analysis of other dynamic domain interactions and conformational changes, and will complement the static models derived from X-ray crystallography.

No technical difficulties with most of the proposed experiments are expected as the required methods were successfully employed in the studies with ASV IN (Examples 1-3), and in preliminary experiments with HIV IN (FIGS. 16A, 16B, and 19). It is possible that the particular amino acid substitutions predicted to disrupt a reaching dimer interface will not be sufficient, or will have confounding effects. If this is the case additional substitutions will be made, informed by the models of potential interactions.

With HIV IN proteins and protein-DNA complexes, aggregation will need to be monitored. Buffer conditions that reduce this problem significantly with the wild-type HIV IN protein have already been identified, and the conditions will be adjusted as required.

These experiments will generate valuable new data concerning the architecture of uniliganded, full length HIV IN in solution, and provide important details relevant to protein dynamics and multimer assembly. It is expected that the results will show that the unliganded reaching dimer interface plays an important role in HIV IN function. The detailed structural information that will be uncovered will allow the identification of additional potential allosteric susceptibilities as targets for inhibitors to be identified using strategies described in Example 7.

Example 7

Identifying Compounds that May Block or Stabilize HIV Reaching Dimer Formation

A compound screening approach. To identify potential inhibitors that affect the stability of reaching dimers, an unbiased screen for small molecules that affect either HIV-1 IN dimer assembly or stability will be undertaken. A first step will be to optimize a specific, high throughput assay for this function.

Figure 20:
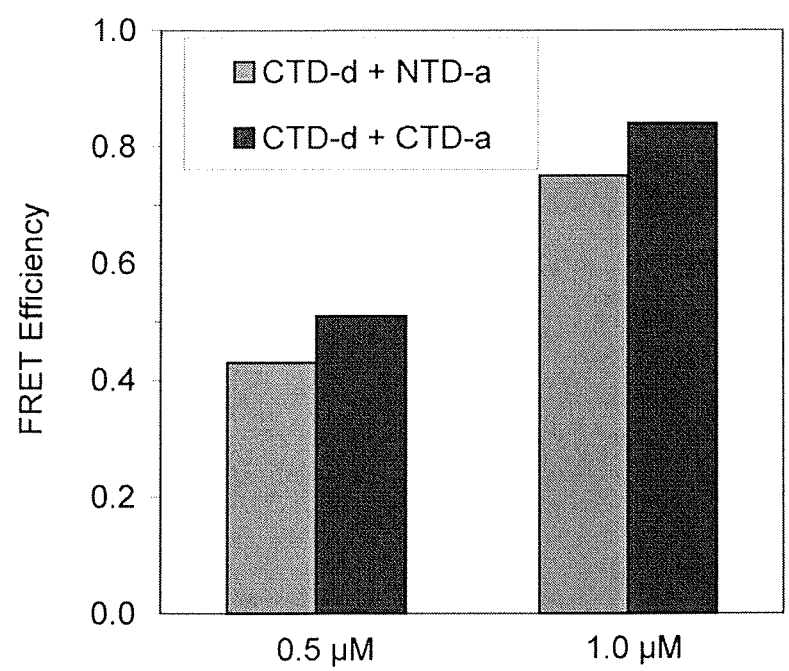
FIG. 20 shows ASV IN reaching dimer-induced FRET. ASV IN proteins were labeled in the CTD(V257C) or NTD(C23) with Cy3 (donor-d) and Cy5 (acceptor-a) fluorophores according to manufacturer recommendations (Invitrogen). Equal amounts of the separately labeled proteins were equilibrated and FRET efficiency was measured.

An assay based on fluorescence resonance energy transfer between donor and acceptor dyes attached to cysteine residues at specified locations on either subunit in the dimer has been developed. To test the feasibility of this approach, preliminary studies have been performed using enzymatically active ASV IN derivatives that contain single accessible cysteine residues at pre-determined locations. FIG. 20 shows the FRET efficiencies obtained when such a derivative, labeled with a donor fluorophore on the CTD (V257C), was equilibrated with the same derivative labeled with an acceptor fluorophore on the same residue, or with a second derivative labeled with an acceptor fluorophore on the NTD (C23). As expected, in both cases the efficiency is highest at 1.0 μM, which is close to the ASV IN equilibrium constant for dimer formation.

The differences between the values are consistent with the differences in distances between the labeled cysteines in the reaching dimer model. Based on these encouraging results with ASV IN similar HIV derivatives will be designed to establish an assay with acceptable Z' scores for high throughput screening. Compounds with intrinsic fluorescence may not be analyzed in such an assay, and those with FRET acceptor or quenching capabilities may score as false negatives or positives. However, proper controls and follow-up validation, including determination of effects on multimerization as assayed by light scattering will be performed with all strong "hits." Should the FRET assay prove inadequate, as an alternative the AlphaScreen technology of Perkin Elmer will be used, which has been used for selection of inhibitors of the HIV IN-LEDGF interaction. The AlphaScreen is not influenced by compound fluorescence, however, the relaxed distance constraints, lack of ability to distinguish different conformations, and increased expense, make this methodology less desirable.

An in-house facility maintains three separate chemical libraries that can be employed for screening: the ICCB Known Bioactives library (~400 compounds), the Johns Hopkins Clinical Compound Library (~1100 compounds) and a 50,000 compound collection from ChemDiv. Compounds in these libraries are structurally diverse and compliant with the Lipinski Rule-of-5 for drug likeness.

Experiments will begin with an assay that is optimized for detection of reduced FRET signal, to identify molecules that may be active in blocking dimerization. Initially screen the smaller ICCB library of bioactive compounds will be screened to test for a hit rate. Compounds will be pin-spotted onto dark 384-well plates that are suitable for FRET signal capture by a plate reader initially at a final concentration of ~0.5 mM for maximum sensitivity. An assay will also be optimized to identify molecules that "lock" or stabilize dimers, by monitoring for increased FRET or sustained FRET following challenge with excess unmodified IN. Controls in the latter screen will include challenge by a molar excess of IN derivatives with amino acid substitutions that prevent dimerization. Screening will continue with the ChemDiv collection, as it contains a large number of synthetic compounds, and has the potential of providing information concerning relevant pharmacophore structure(s) that can inform the in silico modeling described below.

Alternative approaches/follow-up: Additional cross-linking studies using reagents with a variety of lengths, will assist in creating a higher resolution model for the HIV IN reaching dimer. If adequately high resolution structures become available, computational docking will be used to screen available in silico libraries for molecules that are predicted to bind in identified cavities (e.g., Life Chemicals, which is composed of small molecules designed to be drug-like and adhere to Lipinski's Rule of Five), using the Schrodinger suite of programs that includes GLIDE software.

After their structures are confirmed, hit compounds will be tested for their abilities to affect IN multimerization in a screening assay, by protein cross-linking and PAGE, chromatography, and with a subunit exchange assay. Hydrogen-deuterium exchange coupled to liquid chromatography-electrospray ionization mass spectrometry will be used to identify contacts between inhibitors and IN. Where possible, binding at the predicted location will be verified by identification of the expected covalent adducts via mass spectrometry. The contributions of specific amino acids will be analyzed by introducing substitutions and testing for their affects on compound binding.

Example 8

Testing the Effect of Inhibitors on IN Activity In Vitro and In Vivo

The most promising candidate compounds identified from the screening described in Example 7 will be tested rigorously in vitro to determine dose-responses and to confirm their modes of action with wild type IN proteins, using light scattering and SAXS. Compounds that reduce or stabilize IN multimerization, or inhibit subunit exchange and conformational flexibility, might have preferential effects on different steps in the reaction. Effects on DNA binding will be monitored by fluorescence anisotropy assays. Effects on catalytic activities (processing and single end joining activity, as well as concerted integrations) will be monitored using standard methods.

The order of addition of substrates and inhibitor will be varied to identify the most likely mode of action for each compound. It is epected that that one or more compounds that are active in the µM range will be identified and will provide proof-of-concept for the target-selection strategy; these and possible derivatives, will be tested further in cell-based assays.

Initial in vivo tests will take advantage of an assay system in which transduction of 293T cells with an HIV-1 vector encoding a LacZ reporter gene can be used as a simple readout for integration. Cells will be treated with the compound in a range of concentrations and simultaneously infected with the vector. The ideal lead compound will have an $EC_{50}$<50 µM and no or >100 µM toxicity for uninfected cells. The specificity of active compounds will be evaluated by monitoring for effects on reverse-transcription (early and late DNA synthesis), nuclear entry (via 2LTR circle formation), and integration (via alu-PCR). The most promising compounds will be tested for their ability to inhibit replication of HIV infection in primary human PBMCs using X4, T-cell tropic (NL4-3) and R5, Macrophage tropic (ADA) laboratory strains of HIV. With these infectious viruses, selection and analysis of resistant mutants can be used to confirm the molecular basis of inhibitor action.

Although it is not possible to predict how many inhibitory molecules will be identified, screening various compound libraries for inhibitory molecules should prove successful and yield valuable mechanistic insights. It is expected that some of these compounds will be active inhibitors in vitro, but inactive in vivo, or will be toxic to cells. In these cases, the inhibitory compounds can nevertheless be useful as probes for further biochemical analyses and also as leads for future development. Active compounds will be analyzed for specificity with respect to the replication pathway. A compound that has the expected action in vivo will be of major interest to the field.

Example 9

Architecture and Assembly of HIV Integrase Multimers in the Absence of DNA Substrates A. Materials and Methods Static/Size Exclusion Chromatography (SEC)-SAXS/WAXS of ApoHIV IN. X-ray scattering experiments were performed at the Advanced Photon Source at Argonne National Laboratories, 5ID-D beamline, Chicago, Ill. Data were collected either directly from the homogeneous protein solutions or with protein fractions that were eluted at 600 l/min from a Tricorn column (Superdex™ 200, 10/300 GL, GE Healthcare) immediately upstream of the SAXS flow cell. In the latter case, because the proteins were eluting at high concentrations, 3 scans at the retention time were averaged at an interval of 14 s.

Protein Cross-linking. Tag-less HIV IN proteins were buffer-exchanged by dialysis in 0.1 M MES-HCl, 1 M NaCl, pH 6.0, 1 mM Tris(2-carboxyethyl)phosphine, 20% glycerol. For wild type HIV IN cross-linking, a 1:1 mixture of unlabeled and isotopically labeled protein (final concentration 450 nM) was equilibrated overnight and freshly prepared 1-ethyl-3-[3-dimethyaminopropyl]carbodiimide hydrochloride (EDC; Pierce) bifunctional zero-length cross-linker was added at increasing concentrations. After 5-10 min at 37° C., the reactions were quenched by addition of 20 I of 1 M mercaptoethanol and then left on ice for 60 min. After centrifugation at 14,000×g at 4° C. for 10 min to remove unwanted aggregates, the supernatant fractions were transferred to new test tubes. The reactants were then precipitated with acetone and resuspended in 20 mM HEPES, pH 7.8, 0.5 M NaCl, 2 mM DTT, 10% glycerol. For HIV IN F181T cross-linking at 25 M or 250 nM concentration, the mixture of 1:1 unlabeled and isotopically labeled IN was first treated with 10 mM EDTA for 10-15 min on ice, and then dialyzed on ice in 0.1M MES-HCl 1M NaCl, pH 6.0, 20% glycerol supplemented with 2 mM DTT, 20 mM $MgCl_2$, and 50 M $ZnSO_4$. After 60 min to allow for refolding of the NTD, the mixture was dialyzed in 0.1 M MES, pH 5.8, 1 M NaCl, 1 mM Tris(2-carboxyethyl)phosphine, 20% glycerol. Cross-linking of the IN F181T mixtures was as described for wild type IN. The cross-linked products were separated by electrophoresis in denaturing NuPAGE 4-12% BisTris gels using MES running buffer and Coomassie Blue stain. Sample recovery was only slightly diminished by acetone precipitation. The dimer bands from all EDC reactions were excised, trypsin-digested, and analyzed for cross-links by mass spectrometry.

HADDOCK Docking and Fine Model Fit. To model the flexible HIV F181T IN dimer interface, we used HADDOCK docking (Guru Interface) together with SAXS-driven refinement parameters and distance constraints from the mass spectrometric analysis of the protein chemical cross-linking. Starting models for docking were based on homology with the model of the ASV IN dimer using the SWISSMODEL resource, and cross-linking residues were defined to have a proximity of approximately 4 Å between each pair. Based on the flexibilities of the IN domains, docking was grouped into three classes that satisfied the identified chemical cross-links. Structures were selected for further refinement based on the HADDOCK score, and models were clustered with a cutoff root mean square of 10 Å that satisfied the SAXS maximum distance (Dmax). All the final models from each group that have a maximum dimension equivalent to experimental SAXS data were compared using CRYSOL analysis fit (ATSAS). In addition, P(r) functions were plotted for each model and compared with the experimental data to assess the quality of the dock model using the Igor Pro package (frena macro).

B. Experimental Results

Figure 21:
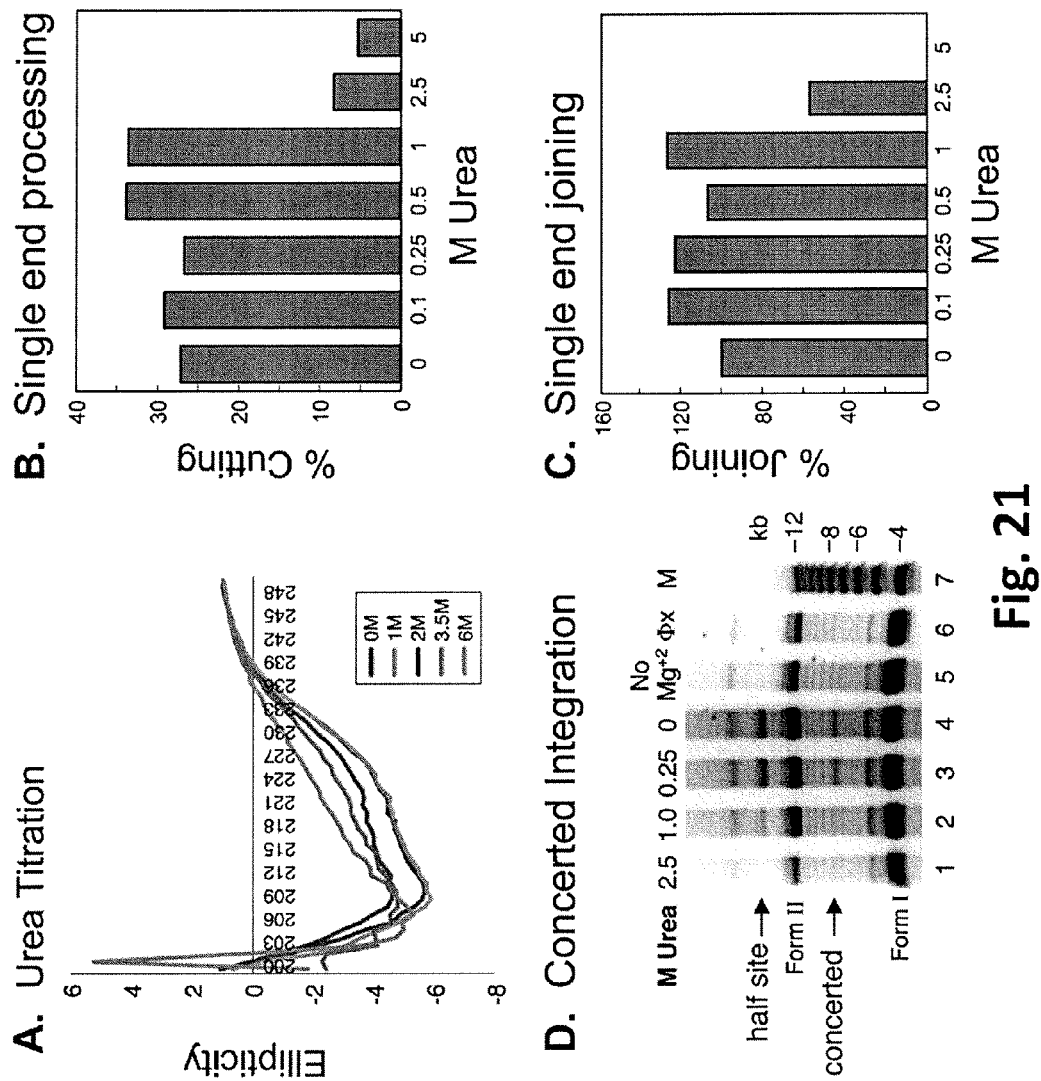
FIG. 21A-D show HIV IN is enzymatically active in the presence of urea. A, shown are CD spectra of wild type HIV-1 IN in the absence and indicated concentrations of urea. Fluorescence-based assays for single end processing are shown in 21B and joining in 21C. Reactions included the indicated concentrations of urea. 21D shows concerted integration; Positions of half-site and concerted integration products are indicated by the arrows; positions of Form I (supercoiled) and Form II (relaxed) circles of the target DNA are also shown. Lane 5, a negative control, contained all reaction components except $MgCl_2$. Lane 6 contained only the target DNA. Markers are shown in lane 7. As with the SAXS experiments, the HIV IN analyzed in these experiments was a His6-tagged version of the wild type protein.

Preparation and Characterization of Wild Type HIV ApoIN. HIV IN is notoriously difficult to maintain at moderate to high concentration because of its tendency to aggregate. After investigating a variety of buffer conditions it was found that solubility and stability could be optimized by the inclusion of 1 M urea during protein purification. Analysis of wild type HIV IN (8 M) by CD spectroscopy revealed no significant differences in the alpha-helical structural elements of the protein in the region of interest (218-223 nm) in the presence of 0-1 M urea; denaturation was not detected until the urea concentration reached 2 M or higher (FIG. 21A). In addition, enzymatic assays showed that single viral DNA end processing and joining activities were unaffected in the presence of 1 M urea; concerted integration into a target DNA was unaffected by 250 mM urea, and this activity was still detectable in 1Murea (FIG. 21B-D). It is believed that these results show that HIV IN retains its native structure in the presence of this chaotropic reagent at concentrations in these biophysical analyses.

Static and dynamic light scattering analyses were used to determine molecular mass and to gauge the homogeneity of the HIV IN protein preparations. It was observed that wild type HIV IN exhibited properties expected of a homogeneous tetramer in the presence of 250 mM and 1 M urea at protein concentrations in the 1-2 mg/ml range (Table 3). In contrast, the protein appeared to be a mixture of tetramers and larger aggregates at similar concentrations in the absence of urea (data not shown).

TABLE 3

Light Scattering data for wild type HIV IN and derivatives

| Protein | [Protein][a] mg/ml | MW-I[b] kDa | S[c] % | PD[d] % | Pd-D[e] % | Comment | R[f] Å |
|---|---|---|---|---|---|---|---|
| HIV-1 IN wild type | 1.63 | 167 | 7.7 | 56 | 10 | Tetramer | 62 |
| HIV-1 IN wild type + $Mg^{2+}$ | 1.58 | 132 | 4.2 | 45 | 11 | Tetramer | 65 |
| HIV-1 IN wild type + EDTA (SEC) | 1.2 | 50 | 7.3 | 77 | 10 | Dimer | 43 |
| HIV-1 IN D64N | 2.48 | 149 | 2.2 | 29 | 18 | Tetramer | 70 |
| HIV-1 IN D64N + $Mg^{2+}$ | 2.4 | 156 | 3.5 | 30 | 27 | Tetramer | 76 |
| HIV-1 IN F181T | 1.5 | 68 | 12 | 57 | 9 | Dimer | 46 |
| HIV-1 IN F181T + $Mg^{2+}$ | 1.2 | 76 | .8 | 53 | 19 | Dimer | 44 |
| HIV-1 IN F181A | 3.2 | 64 | 5.4 | 57 | 11 | Dimer | 44 |
| HIV-1 IN F181G | 2.3 | 116 | 8.5 | 57 | 11 | Mixture | 57 |
| HIV-1 IN E11K | 1.85 | 76 | 9.5 | 44 | 29 | Dimer | 60 |

[a]Protein concentration in mg/ml, measured using molar extinction coefficient of the respective IN protein.
[b]Apparent molecular mass (MW-I) was determined by static light scattering and calculated using DynaPro Version 5 software.
[c]Percentage standard deviation, S.
[d]The % polydispersity of the same was determined using a cumulants analysis.
[e]Polydisperity index.
[f]Hydrodyname radius, $R_h$, of the apparent multimer calculated from differential coefficient of the Stokes Einstein equation.

Disruption of Hydrophobic Interactions in the Core-Core Interface of HIV IN Blocks Tetramer but Not Dimer Formation. As shown in the foregoing examples, in the absence of DNA, full-length ASV IN forms two distinct subunit interfaces. A reaching dimer interface is stabilized by CTD-CTD interactions and interactions of the NTD from one monomer with the CTD and core domain of the second monomer. A second interface stabilized by core-core domain interactions is observed in ASV IN tetramers, which is believed to be required for catalysis of concerted integration but not 3-end processing of viral DNA.

Figure 22:
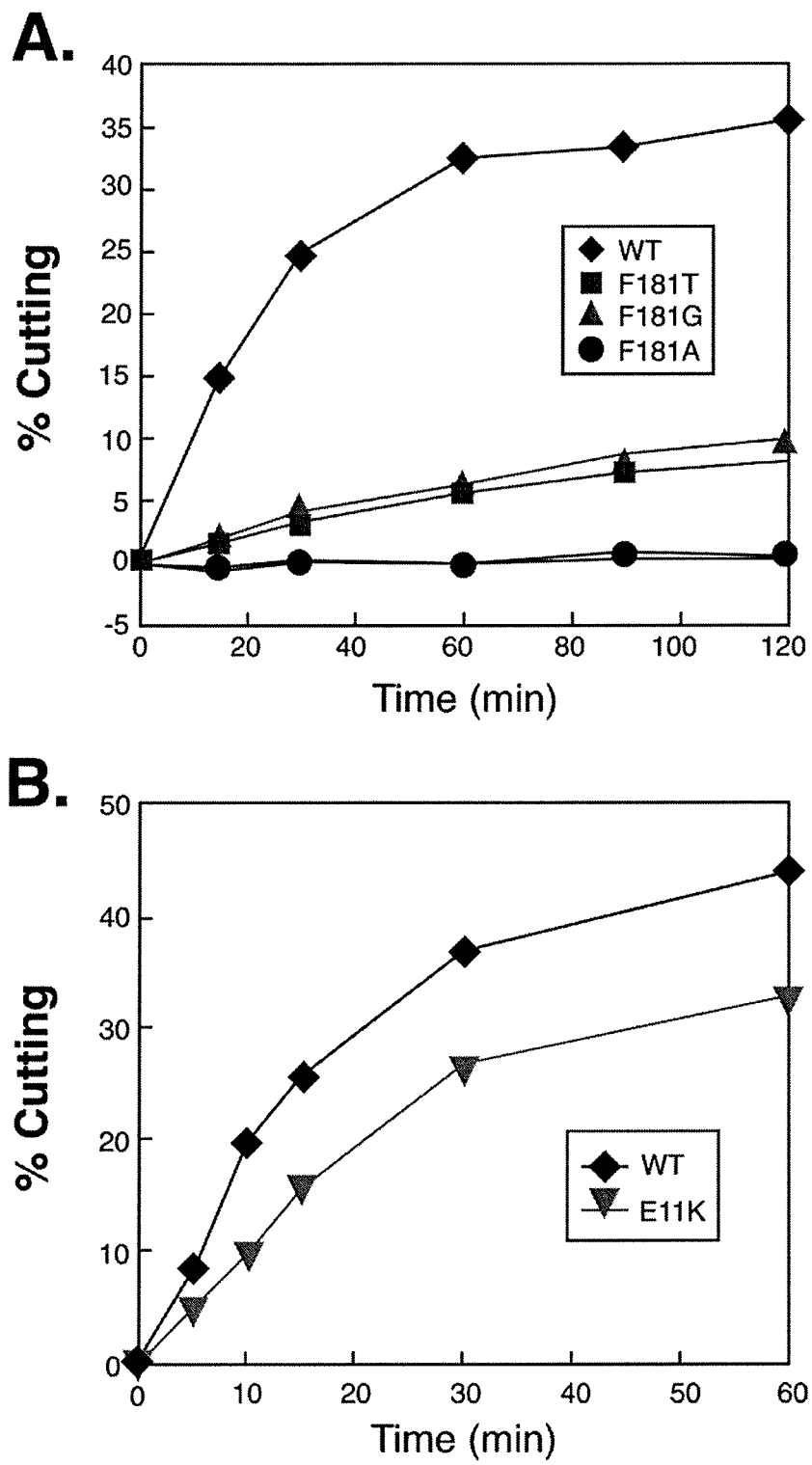
FIGS. 22A and B show processing activities of HIV-1 IN Phe-181- and E11K-substituted derivatives.
FIG. 22B shows a comparison of wild type HIV IN and the Glu-11-substituted protein.

By analogy with ASV IN, it was hypothesized that substitution of one or more conserved hydrophobic residues in the HIV IN core domain might block formation of tetramers but not reaching dimers. To test this idea, three independent, non-conservative substitutions were introduced for residue Phe-181 in wild type HIV IN these proteins were analyzed by dynamic light scattering. The results showed that the HIV IN derivatives with either threonine (1.2 mg/ml) or alanine (3.2 mg/ml) at position 181 were homogenous dimers in the presence of 1 M urea; the protein that contained glycine (2.3 mg/ml) at this position had properties expected for a mixture of dimers and tetramers (Table 3). The enzymatic assays showed that the IN F181A derivative was essentially inactive for 3 end-processing, but F181T and F181G retained 12% of the catalytic rate exhibited by wild type HIV IN (FIG. 22A). These data indicate that the HIV IN protein can form partially active dimers when core-core interactions are disrupted.

Destabilization of NTD Structure Blocks Formation of Reaching Dimers but Not Core-Core Dimers. The NTD of HIV IN contains a conserved $Zn^{+2}$ binding motif (HH-CC), and the presence of this ion is required for conformational integrity of this domain. As the reaching dimer of ASV IN is stabilized by interactions of the NTD with the core and CTD of the second IN monomer, it was reasoned that disruption of the NTD structure would prevent formation of an HIV IN reaching dimer but not a dimer formed by core-core interactions (illustrated in FIG. 30, left). To remove the NTD-bound $Zn^{+2}$ ion, wild type HIV-1 IN (1.5 mg/ml) was dialyzed overnight in buffer (including 1MNaCl and 1Murea) supplemented with 10 mM EDTA and then concentrated to 5 mg/ml.

A sample of this protein was then applied to a SEC column that had been pre-equilibrated with the same EDTA-supplemented buffer. A homogeneous peak of protein was eluted from this column with retention time (24.3 min) expected for a dimer. The F181T derivative eluted as a dimer in SEC (24.75 min) in the absence of EDTA treatment. When the IN F181T was treated with EDTA and chromatographed in the presence of EDTA, its retention time was 26.2 min, consistent with a monomer. Light scattering analysis of untreated IN F181T and EDTA-treated wild type IN confirmed that both were dimers (Tables 3 and 4). These results support the hypothesis that destabilization of the NTD by removal of $Zn^{+2}$ ion leads to disruption of the reaching dimer interface but will allow core-core stabilized dimers to assemble. The light scattering data, at higher concentrations (Table 3), also revealed dimers, and an expected reduction in enzymatic activity of this derivative is illustrated by analysis of 3 processing (FIG. 22B).

TABLE 4

SAXS parameters for wild type HIV IN and derivatives

| Protein | [Protein] mg/ml | $R_g{}^a$ Å | $D_{max}{}^a$ Å | $I(0)^a$ |
|---|---|---|---|---|
| HIV-1 IN wild type | 1.7 | 40 ± 1 | 117 ± 2 | 0.053-0.06 |
| HIV-1 IN wild type + $Mg^{2+}$ | 1.6 | 41 ± 1 | 132 ± 1 | 0.06 |
| HIV-1 IN D64N | 2.8 | 44 ± 2 | 142 ± 3 | 0.06 |
| HIV-1 IN D64N + $Mg^{2+}$ | 2.3 | 45 ± 1 | 147 ± 1 | 0.07 |
| HIV-1 IN F181T | 1.9 | 33 ± 2 | 107 ± 3 | 0.03 |
| HIV-1 IN F181T + $Mg^{2+}$ | 1.9 | 34 ± 1 | 103 ± 1 | 0.027 |
| HIV-1 IN WT EDTA(SEC)$^e$ | 1.2 | 33 ± 2 | 100 ± 2 | 0.04 |
| HIV-1 IN F181T EDTA(SEC)$^e$ | 1.9 | 29 ± 1 | 88 ± 1 | 0.025 |
| HIV-1 IN E11K | 1.8 | 39 ± 1 | 124 ± 1 | 0.032 |

| Protein | Volume$^b$ Å$^3$ | Apparent multimer (LS)$^c$ | MW-I$^d$ kDa |
|---|---|---|---|
| HIV-1 IN wild type | 260 | Tetramer | 168 |
| HIV-1 IN wild type + $Mg^{2+}$ | 305 | Tetramer | 132 |
| HIV-1 IN D64N | 281 | Tetramer | 149 |
| HIV-1 IN D64N + $Mg^{2+}$ | 288 | Tetramer | 156 |
| HIV-1 IN F181T | 150 | Dimer | 60 |
| HIV-1 IN F181T + $Mg^{2+}$ | 166 | Dimer | 76 |
| HIV-1 IN WT EDTA(SEC)$^e$ | 233 | Dimer | 50 |
| HIV-1 IN F181T EDTA(SEC)$^e$ | 82 | ND | ND |
| HIV-1 IN E11K | 179 | Dimer | 76 |

ND, not determined
$^a$SAXS scattering data obtained from IN proteins at the listed concentrations were processed with the program IRENA to determine the radius of gyration ($R_g$) and the maximum length of the scattering multimer ($D_{max}$) and I(0).
$^b$The volume of the Situs-derived envelope was calculated with Chimera software (UCSF).
$^c$The apparent multimer was determined from light scattering (LS).
$^d$The MW-I as determined by DynaPro Dynamica software is expressed in kilodaltons.
$^e$EDTA-treated IN proteins separated by SEC were directly injected into the SAXS beam line.

SAXS Analysis of Wild Type HIV IN and the F181T and E11K Dimers. The homogeneous preparations of wild type HIV IN tetramers and derivative dimers were next analyzed by SAXS at protein concentrations ranging from approximately 1 to 2 mg/ml. A summary of the SAXS determined parameters and apparent multimeric state of each of the proteins analyzed is provided in Table 4. Consistent with the light-scattering results, SAXS data for all proteins in the Guinier regions and Kratky plots confirmed the absence of aggregation or unfolding of IN (data not shown). A PRIMUS analysis of scattering intensity versus a q range of 0.01-0.04 for four independent wild type IN concentrations also showed that there was no concentration dependent aggregation in the range tested (data not shown).

The scattering profiles for wild type HIV IN and the F181T and E11K dimers are shown in FIG. 23A; their pair distance distribution P(r) functions using data to a qmax of 0.4 Å|1 revealed no major deviations in the $D_{max}$ as a function of concentration in the range of 1-1.5 mg/ml (FIG. 23B). SAXS scattering parameters for IN F181T, either as a stock preparation or from direct analysis of a size exclusion column fraction (SEC-SAXS), show average $R_g$ values of 33-36 Å, and $D_{max}$ values of 107-113 Å, respectively, whereas the E11K protein showed an $R_g$ of 39 Å and $D_{max}$ of 124 Å. An $R_g$ of 40 Å and $D_{max}$ of 117 Å were obtained with the wild type HIV IN. The SAXS derived I(0) value for the wild type HIV IN tetramer, is approximately twice that observed for both dimers (Table 4). The similar values of I(0) for F181T and E11K proteins indicate that both contain the absolute mass expected of an HIV IN dimer (Tables 3 and 4). However, the significant differences in the $D_{max}$ and $R_g$ values of F181T and E11K dimers are indicative of distinct assemblies; that is, a compact dimer in the case of F181T and a more extended dimer for E11K.

SAXS envelopes for these proteins were derived using GASBOR modeling (FIG. 23C). The dimensions of the HIV F181T IN dimer are similar to those of the reaching dimer of full-length ASV IN, as described in the foregoing Examples, with minor differences in the contours of the envelopes. Furthermore, the $D_{max}$ of 117 Å observed for the HIV IN tetramer is only slightly larger than that of the F181T dimer, whereas the volume calculated for the tetramer is approaching twice that of the F181T dimer (Table 4). The envelope derived for E11K is larger than that of F181T and the shape is longer than either the wild type tetramer or the F181T dimer with a distinct contour and narrower ends.

Figure 24:
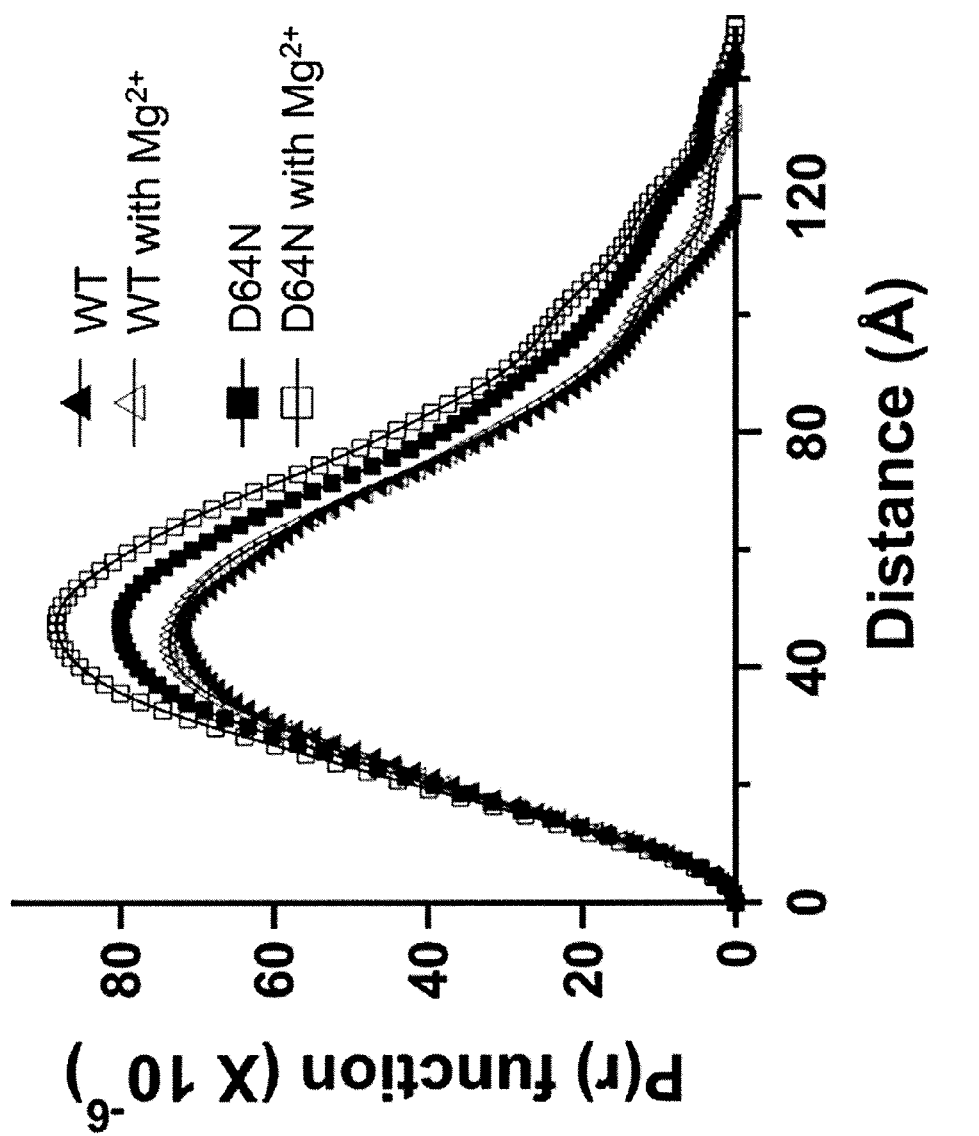
FIG. 24 shows a comparison of P(r) functions of wild type HIV IN and a D64N derivative in the presence and absence of the metal cofactor ($Mg^{+2}$).

SAXS Analysis of Wild Type HIV IN and Derivatives in the Presence of the Metal ($Mg^{+2}$) Cofactor. As the enzymatic activities of HIV IN are highly cofactor-dependent, it was asked whether the presence of $Mg^{+2}$ would alter the overall architecture of the protein in solution. These experiments included wild type IN, a D64N derivative that cannot bind the metal cofactor at the active site, and the F181T dimer. The results from light scattering studies indicated that the size of these three proteins was not altered significantly in the presence of $Mg^{+2}$ (Table 3). Comparison of the SAXS parameters in the absence or presence of the metal showed minor variations in the $D_{max}$ values but no drastic change in the $R_g$ values (Table 4). P(r) functions for wild type IN and the D64N derivative in the absence and presence of $Mg^{+2}$ are shown in FIG. 24.

As summarized in Table 4, in the presence of $Mg^{+2}$, slight increases were observed in the $D_{max}$ of $\Delta^-+10$ Å and $\Delta^-+5$ Å for the wild type IN and D64N IN respectively, whereas the F181T derivative showed a decrease in the $D_{max}$ of 4 Å in the presence of the metal. The volume of IN envelopes in the presence of the metal changed in a corresponding manner. Finally, the shapes determined for proteins in the presence of $Mg^{+2}$ showed only slight variations in the contour and extent of the envelopes compared with proteins in the absence of metal (data not shown). Based on these results it is believed that there are no gross changes in HIV IN architecture upon addition of the metal cofactor.

Figure 25:
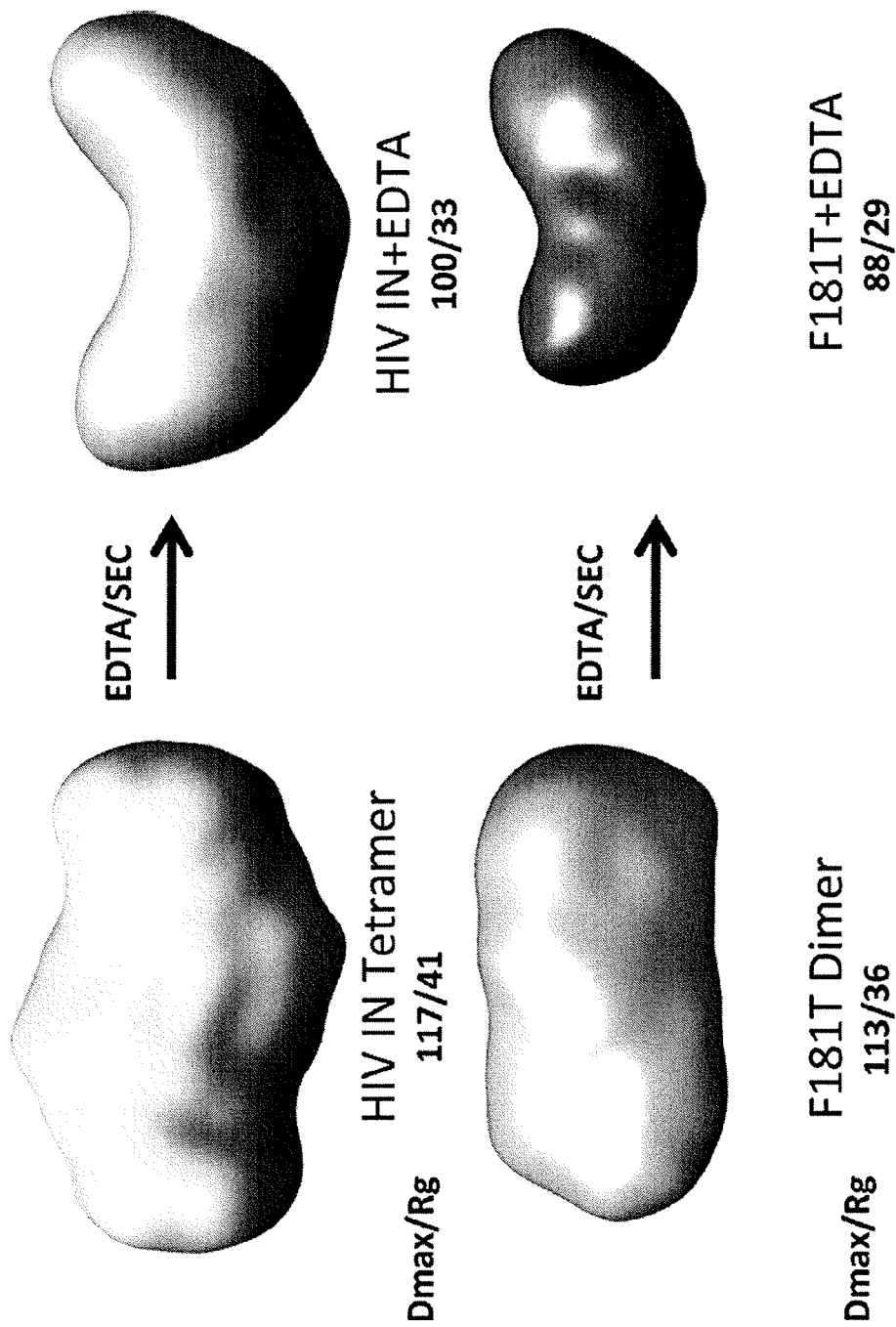
FIG. 25 shows destabilization of the wild type HIV IN tetramer and F181T dimer assembly by EDTA treatment. SAXS envelopes were derived for proteins treated with EDTA and separated by size exchange chromatography (SEC-SAXS).

SAXS Analysis of EDTA-treated HIV IN Proteins. EDTA-treated, SEC-purified wild type HIV IN dimers and F181T monomers were also analyzed by SAXS. Envelopes derived for these EDTA-treated proteins are shown in FIG. 25 and, judging from their Kratky plots (not shown), both of these proteins have lost some secondary structure compared with untreated proteins. SAXS parameters for the EDTA-derived wild type IN dimer show values of 33 Å for the $R_g$ and 100 Å for $D_{max}$, which are quite similar to the values of 36 and 113 Å, respectively, for the SEC isolated IN F181T dimer. However, the volume of the wild type EDTA derived dimer is larger than that of the IN F181T dimer, indicating that the conformations are likely to be distinct (Table 4). Indeed, the envelopes derived for the wild type IN EDTA dimer and the F181T IN dimer are quite different, consistent with the notion that there are two distinct modes of stabilization of their respective dimer interfaces. The difference in contours of the wild type EDTA dimer and the E11K dimer likely reflects the disorder of the NTD associated with the removal of $Zn^{+2}$ ion. The EDTA-treated HIV IN F181T monomer exhibited reduced values for $R_g$ and $D_{max}$ compared with the untreated protein. These results are consistent with a monomer with disordered NTD (FIG. 25).

Identification of Intersubunit Proximities in the HIV IN Reaching Dimer. In the foregoing Examples, isotopic labeling followed by chemical cross-linking and mass spectrometry was used to map the interacting interfaces in ASV IN dimers and tetramers. In this Example, similar methods were employed to identify the intermolecular proximities of protein domains in the HIV IN F181T dimer, and the wild type IN dimer(s) that exist at low protein concentration. The strategy was to mix equal amounts of separate preparations of unlabeled and isotopically labeled lysine ($^{13}C$, $^{15}N$) and arginine ($^{13}C$, $^{15}N$) proteins and allow the mixtures to equilibrate such that they formed mixed multimers. In preliminary tests, it was observed that labeled and unlabeled monomers of the F181T derivative did not exchange as readily as those of wild type IN, indicating that the F181T dimer was somewhat more stable than the wild type. To facilitate exchange the F181T protein was treated with 10 mM EDTA to form monomers; mixed dimers were readily assembled upon the addition of $Zn^{+2}$ ion through slow dialysis (see above).

After treatment with the EDC cross-linking reagent, the wild type IN or F181T IN products were separated by electrophoresis in a denaturing gel. Protein excised from the dimer band was then subjected to trypsin digestion and mass spectrometry. Intersubunit cross-linked peptides are recognized uniquely by their hybrid mass. The observed mass differences for cross-linked labeled and unlabeled tryptic peptides were consistent with the expected values of K+8.014 and R+10.008, where K and R are masses of unlabeled lysine and arginine, respectively.

The reagent used in these experiments, EDC, promotes formation of trypsin-resistant, irreversible cross-links between the carboxyl groups of acidic amino acids, such as aspartate and glutamate, with the side chains of lysine residues that act as salt bridge partners. Gel electrophoresis of the IN F181T products revealed robust cross-linked dimer bands at 25 M concentration (FIG. 26A(i)). At 250 nM, only dimers were detected (FIG. 26A(ii)), and the same was true for wild type IN at 450 nM (FIG. 26A(iii)). Unfortunately, this method is not useful for mapping oligomers higher than dimers, as cross-links from more than two interacting monomers are difficult to distinguish. Consequently, efforts focused on mapping the dimer interfaces.

Figure 26:
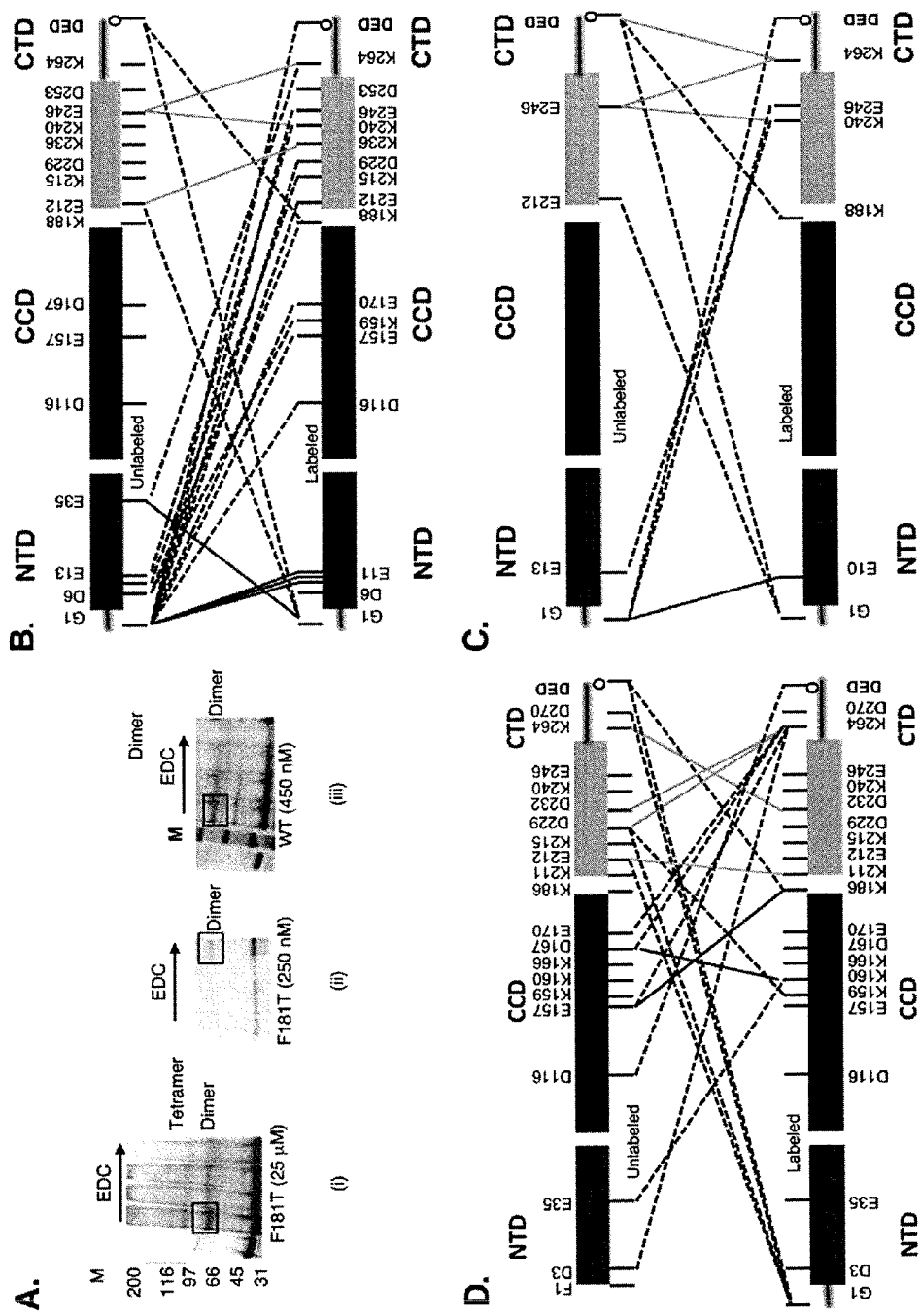
FIG. 26A-D shows inter-protein proximities in HIV IN dimers identified by chemical cross linking coupled with mass spectrometry.

Data obtained with F181T IN at 25 M revealed numerous cross-links between residues in the NTD of the unlabeled monomer with the CTD of the labeled monomer (FIG. 26B). This included interactions between Glu-11, Glu-13, and Glu-35 in the NTD with lysines at positions 215, 240, and 264 in the CTD. Cross-links of NTD to NTD, NTD to core, and CTD to CTD were also detected. The IN F181T derivative includes an N-terminal extension of three amino acid residues, Gly, His, and Met, which remains after removal of the His tag. This Gly-1 is also capable of forming cross-links to the core domain at Glu-157 and Glu-170. The C-terminal tail extremities of both the labeled and unlabeled monomers were found to form cross-links to G1 in the other subunit. As the labeled IN only incorporates isotopes of Lys and Arg, the origin of the cross-linked tryptic fragments that include the extreme tail, with sequence QDED, could not be determined. G1 of the unlabeled monomer of F181T IN is observed to form cross-links with labeled IN at helical regions of the NTD at positions Glu-10, Glu-11, and Glu-13. Glu-35 from unlabeled IN is crosslinked with G1 of the labeled IN. These cross-links reveal the proximities of the NTD helical regions in the unlabeled and labeled IN subunits.

In addition to cross-links to secondary structural elements of the NTD, core, and CTD tail ends, G1 was observed to crosslink at CTD beta-sheet elements at positions Asp-229 and Glu-246 in IN F181T. Furthermore, Glu-212 from both labeled and unlabeled IN was found to cross-link with G1 on unlabeled and labeled IN, respectively (FIG. 26B). Helical regions of the NTD from the unlabeled IN at positions Asp-6, Glu-11, Glu-13, and Glu-35 were also cross-linked to the labeled lysines in either the core or CTD regions. Cross-links between beta-sheet regions in the CTDs of the unlabeled and labeled F181T IN were observed between residues Glu-212 and Glu-246, with Lys-236, Lys-240, and Lys-264 (FIG. 26B). Overall these results indicate that the HIV IN F181T dimer is stabilized by interactions of the NTD of the one monomer subunit with the core, CTD, and NTD of the second subunit. In addition, CTD-CTD interactions are also detected between the two subunits. Finally, no cross-links were observed between the core domains of the monomer subunits, indicating that this dimer is not stabilized by core-core interactions but rather more the reaching dimer architecture observed with wild type ASV IN. Results from mass spectrometry closely resembles analysis of cross-linked peptides formed with IN F181T at 250 nM protein concentration are summarized in FIG. 26C. Fewer interactions were detected under these conditions. However, all of the cross-links found in this sample were included in the set obtained at the higher protein concentration (FIG. 26B).

Results from mass spectrometry analysis of cross-linked peptides from the dimer band of wild type HIV IN treated with EDC at 450 nM concentration are summarized in FIG. 26D. Seventeen cross-links were detected between labeled and unlabeled IN. Although prominent interactions of the NTD with the core and CTD were observed, the crosslinks are at different positions than observed with the IN F181T dimer. For example, the CTD to CTD cross-links in the wild type IN dimer were Glu-212-Lys-211, Asp-229-Lys-264, Asp-232-Lys-264, and Lys264-Asp-232, whereas with IN F181T, the cross-links were Glu-212-Lys-236, Glu-246-Lys-240, and Glu-246-Lys-264 (compare FIGS. 26B and 26D). Other distinct features of the wild type dimer were observed in the region of the core-CTD interface, including cross-links of Glu-170-Lys-264, Asp-229-Lys-159, and Asp-167-Lys-264, and NTD-core and NTD-CTD cross-links at Glu-35-Lys-160 and Asp-3-Lys-264. Furthermore, core-core cross-links at Glu-157-Lys-186 and Asp-167-Lys-160 were interactions observed only with the wild type dimer. Most notably, unlike the F181T dimer, no cross-links were observed between the NTDs from each interacting monomer in the wild type dimer. A number of the intermolecular cross-links observed with the wild type HIV IN were mutually exclusive, likely arising from a mixture of oligomers. The possibility that some of the cross-links (e.g., core-core adducts) reflect inclusion in the SDS PAGE dimer band of products from cross-linked tetramers cannot be excluded.

That caveat aside, the results are most consistent with a cross-linked population comprising alternate reaching dimer configurations as well as some core-core dimer forms. With respect to the wild type reaching dimer architecture, the NTD-core cross-link between Glu-35 and Lys-160 is likely to represent a biologically relevant interface, as a careful analysis using PROTCID reveals that a common interface with these residues in close proximity exists in all two-domain (NTD+core) IN proteins that have been crystallized to date, including those of HIV-1, HIV-2, PFV, and maedi visna virus. The interface is observed in both intra- and intermolecular interactions. In contrast to the wild type, there is no evidence for this common interface in the IN F181T reaching dimer. It seems probable that the non-conservative substitution of Phe-181, which is located in this interface, disrupts this common NTD-core interaction leading to a shifted reaching dimer conformation that is manifested most clearly in the adjacent arrangement of NTDs in the IN F181T dimer. Such a shift could account for the increased stability of the F181T dimer noted above.

Figure 27:
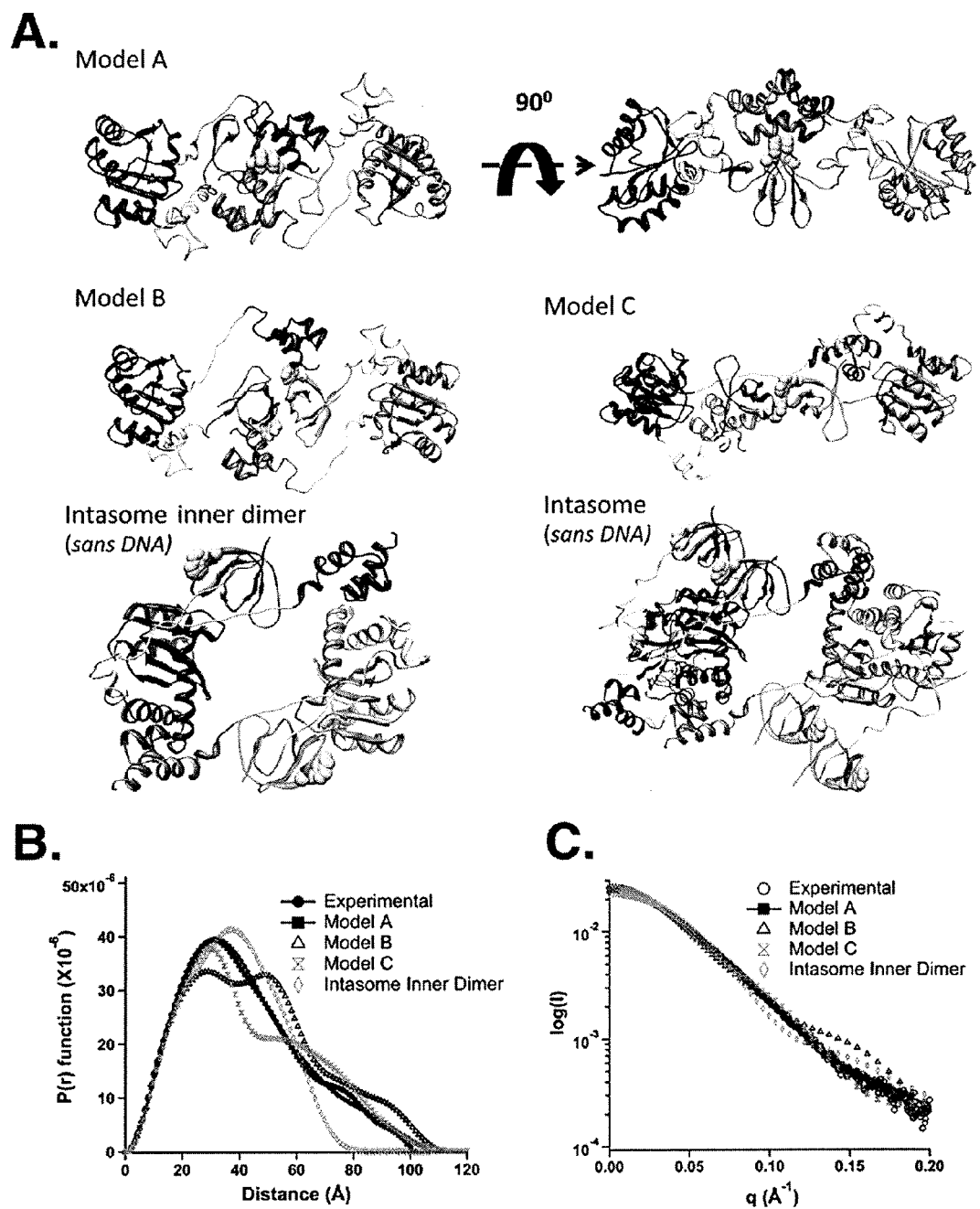
FIG. 27A-C shows models of the HIV IN F181T reaching dimer and selection of the best fit.

Data-driven Docking and Model Fit into SAXS Envelopes. To obtain a more detailed model of the HIV IN F181T dimer, the mass spectrometric data obtained from the cross-linking experiment summarized in FIG. 26B was used. The starting template for a monomer of F181T IN was a homology model derived from the ASV IN reaching dimer (Examples above), with data-driven docking using the HADDOCK module. The presence of mutually exclusive beta-strand cross-links at the CTD-CTD interface (FIGS. 26B and 26C) is likely to reflect dynamic movement at this interface. For example, NTD residues are observed with cross-links to either core or CTD, and further cross-links between CTD domains engage different beta-strands (FIG. 26B). Therefore, to characterize the predominant conformational state of the IN F181T dimer, cross-link contacts were parsed into three groups for which the distance constraints are compatible and satisfy the maximum distance ($D_{max}$) from SAXS data (FIG. 27). In the first group dock model A (FIG. 27A, top) the distance constraints of the Glu-246-Lys-240 were maintained in addition to NTD-NTD interactions with cross-links of G1 with Glu-10, Glu-11, Glu-13, and Glu-35; NTD cross-links to CTD at G1-Glu-212 and Glu-11-Lys-215 are also included (FIG. 26B). In the second group dock model B, the salt bridge distances of Glu-246-Lys-264 were maintained in addition to the links between Glu-11-Lys-215, Glu-35-Lys-264, and G1-Asp-116. In this conformation, the interactions between the Trp-243 residues from each monomer are disrupted. In the third group dock model C interactions are similar to dock model A, except NTD-NTD proximities were relaxed. NTD-to-core distances were enforced at G1-Asp-116, G1-Glu-157, Asp-6-Lys-159, and Asp-6-Lys-188. In this model, NTD cross-links to CTD at G1-Glu-212 and Glu-11-Lys-215 are not taken into consideration. During successive cycles of the optimization for each group, we included newly observed features that increased the hydrophobic packing in the interacting domains at the interface and that satisfied the SAXS determined maximum distance $D_{max}$.

Because of the dynamic nature of movements of the NTD and CTD with respect to the core domain, in all three dock models studies were carried out to determine which configuration might represent the closest parity with the actual experimental data and, therefore, the predominant dimer architecture. Although independently obtained, comparison of the CRYSOL-derived P(r) function for each of the models with the experimental data and analysis of the predicted scattering profiles (FIGS. 27B and 27C) indicated that the closest identity was obtained with model A. Furthermore, a predicted inner dimer model based on the PFV intasome crystal structure with viral DNA removed (i.e., intasome inner dimer sans DNA; FIG. 27A) showed a large difference of 30 Å in $D_{max}$ and scattering when compared with experimental data. These analyses showed good correlation between the data-driven docking reaching dimer model A and the observed SAXS parameters.

Figure 28:
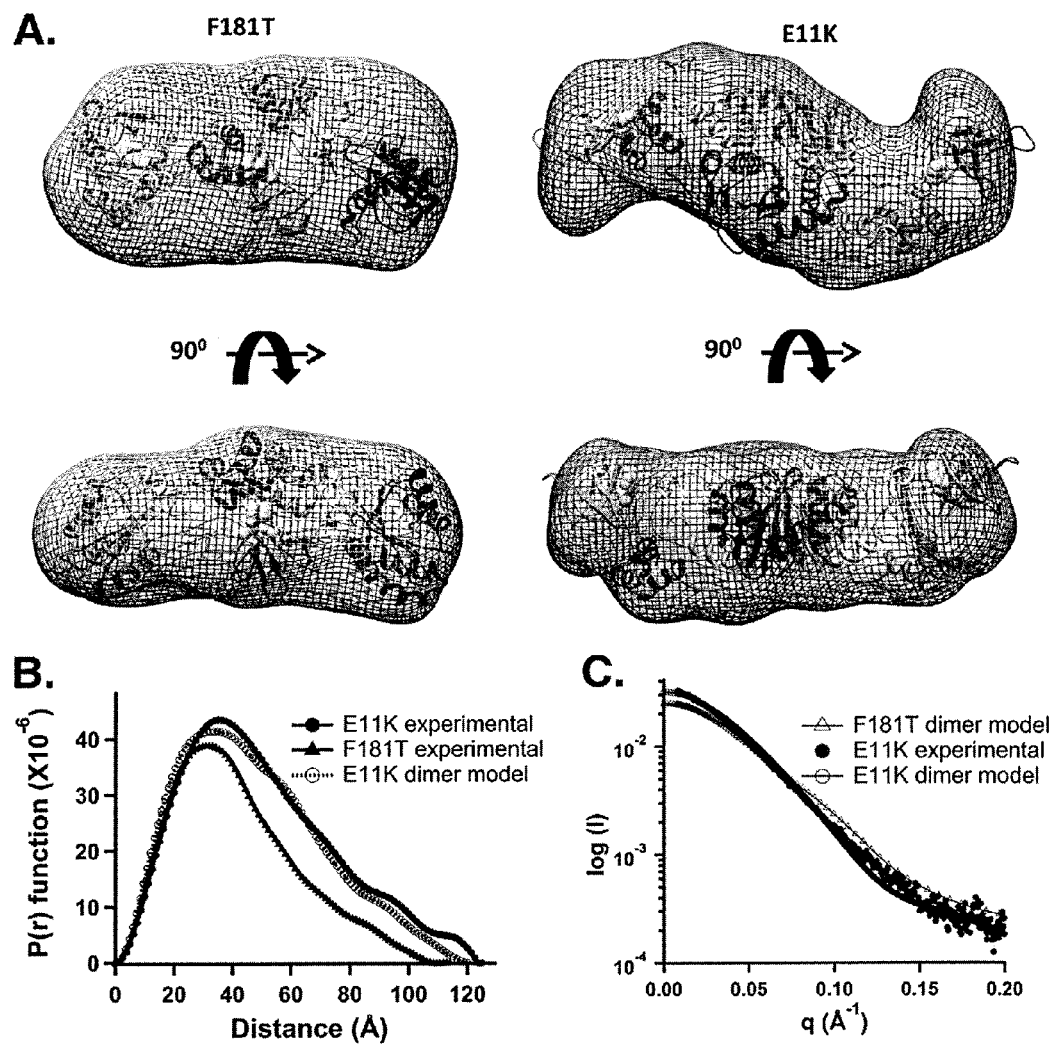
FIG. 28 (right) shows a model of E11K fit into its SAXS-derived envelope.

The unique features of the HIV IN F181T model A reaching dimer are a CTD-CTD interface with prominent Trp-243 hydrophobic interactions (FIG. 27A) and stacking of both NTD domains above the CTD domains. The final, most accurate model from the HADDOCK docking was fitted into the experimental SAXS envelope, and its occupancy inside the envelope was 95% (FIG. 28A, left). Although model A in FIG. 27A includes only residues 1-270, the analyses indicated that the addition of the 18-amino acid tail and disordered N-terminal His6 into the final model had insignificant effects on the CRYSOL profiles (data not shown).

As noted above, the SAXS-derived envelope of the E11K IN dimer is longer than either the F181T dimer or the wild type tetramer; its unique shape includes narrow extremities and bulging occupancy at the center (FIG. 23C). As the core interface residues are not changed in the E11K substitution, this dimer should include a core-core domain interaction. To model an architecture that would satisfy these features, residues 60-186 of the core domain crystal structure (PDB ID IBIS) was selected to represent the core domain dimer, which could only be accommodated in the central bulge of the E11K envelope. Attempts to place NTD and CTD dimer pairs at the narrow extremities of the envelope (PDB IDs 1E0E and 1QMC, respectively) resulted in a model that did not fit the experimental data (not shown). The alternative arrangement, with an NTD and CTD at both ends, was a better fit, and this model was further refined with SWISS MODEL by placing one CTD domain at either extremity with the NTDs nested between the CTD and core domains; the missing linkers were built between the domains as shown in FIG. 28A, right. The SAXS scattering data and P(r) function derived for this E11K dimer model compared well with the experimental data (FIGS. 28B and 28C) and, as expected, was distinct from F181T data.

Figure 29A:
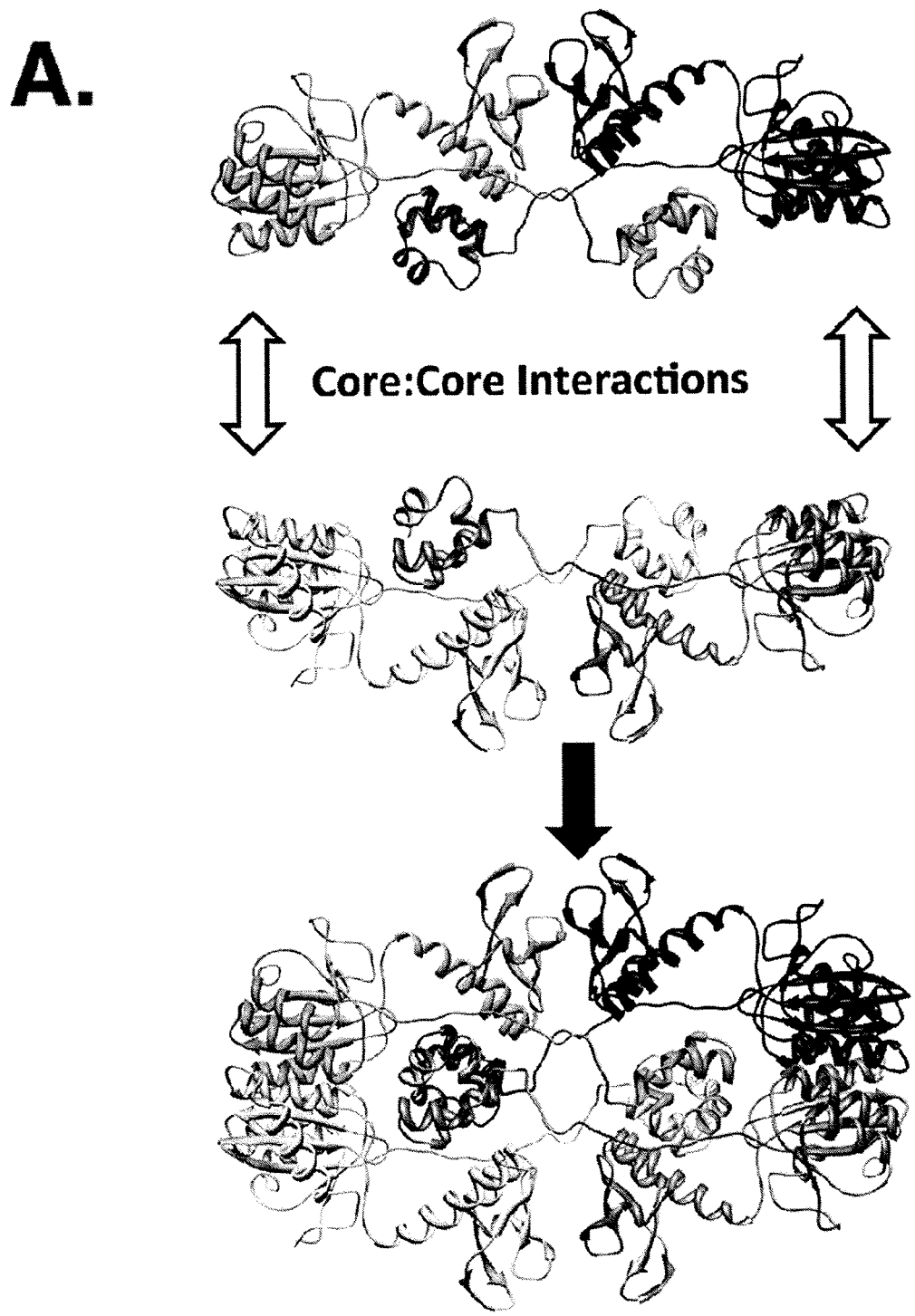

Building an HIV IN Tetramer. As described above, disruption of core-core interactions at Phe-181 of HIV IN revealed a unique homo-dimer whose SAXS analyses yielded very similar Dmax to that of the homo-tetramer of wild type IN (FIG. 23B). The volumes from the SAXS-derived envelopes of the wild type IN tetramer and F181T IN dimer, 260 and 130 Å3, respectively (Table 4), indicated that the homo-tetramer has twice the volume of a homo-dimer with similar $D_{max}$. Comparison of these parameters and the SAXS envelope shapes suggests that IN tetramers assemble by the stacking of two reaching dimers through core-core interactions of both dimers. FIG. 29A shows a plausible model for the formation of a wild type tetramer by such stacking. Coalescence of the two reaching dimers in this manner results in a tetramer that has same maximum dimension as a reaching dimer. The corresponding wild type tetramer model, which places the NTDs in close proximity to the core interfaces, fits into the SAXS envelope as shown in FIG. 29B.

Figure 29C:
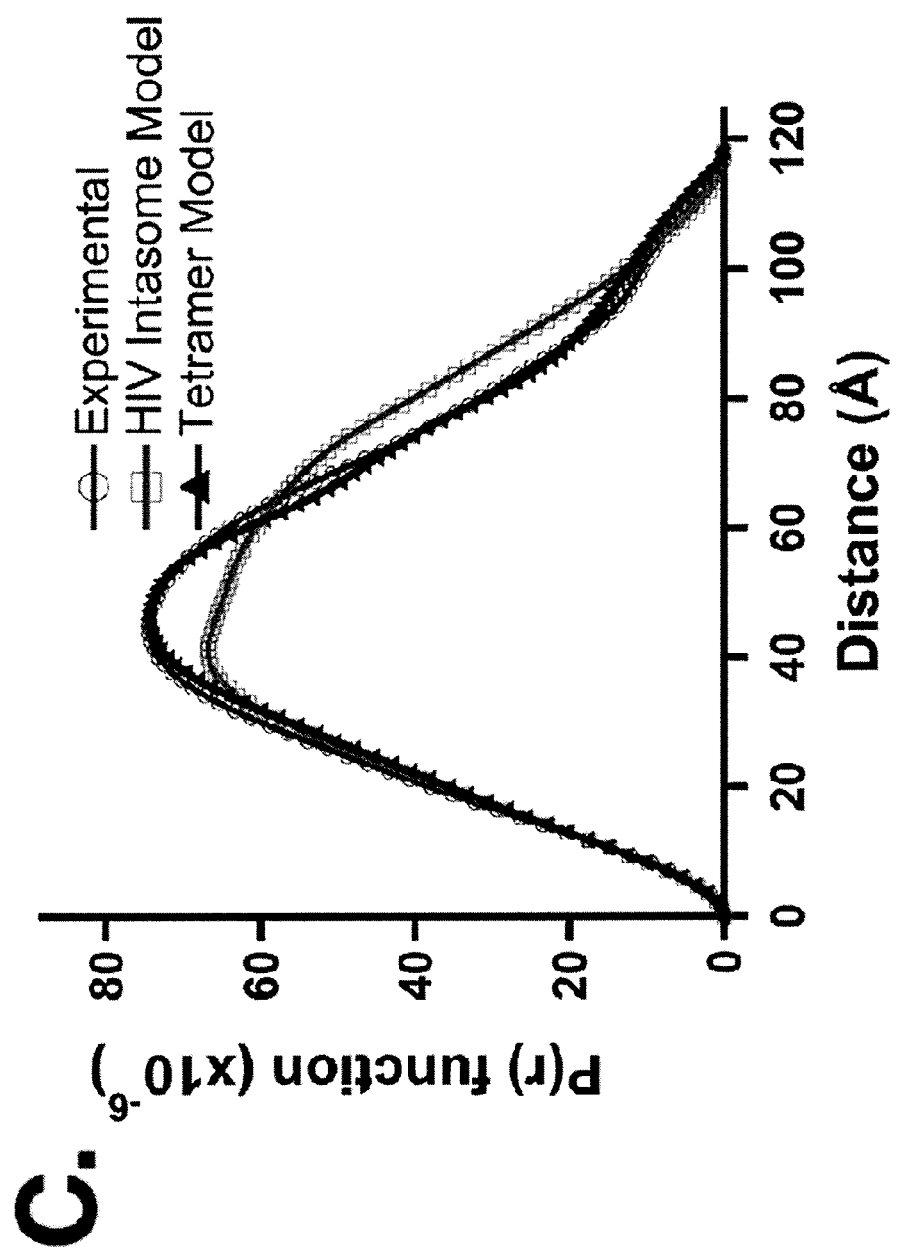

CRYSOL was applied to gauge the correctness of this tetramer model without any bias with respect to the experimental data. The intasome sans DNA model was also included in this comparison. The results indicate that the apoform of the HIV IN tetramer comprising stacked reaching dimers is most compatible with the experimental data (FIG. 29C). Furthermore, the SAXS data for apoIN are inconsistent with the elongated model of the HIV intasome sans DNA tetramer derived from the crystal structures or solution structures of PFV.

C. Summary

Figure 23:
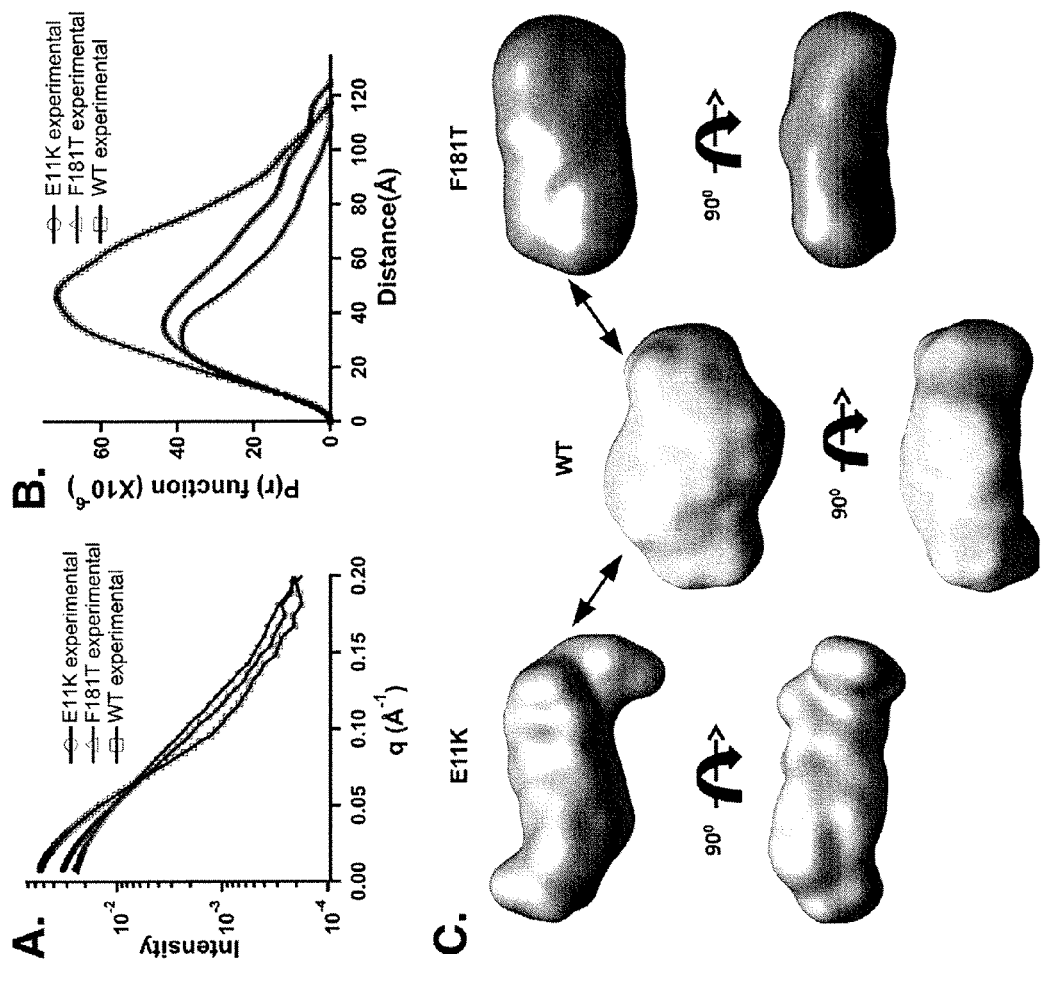
FIG. 23A-C shows SAXS data and envelopes for wild type HIV IN and the F181T and E11K derivatives.

In this Example, SAXS, protein cross-linking coupled with mass spectrometry, and molecular modeling were used to reveal the architectures of full-length HIV IN dimers in the absence of DNA substrates (apoIN). The analyses distinguish two dimer forms of the protein. One form, stabilized by core-core interactions, is observed when a charge substitution, E11K, is introduced into the NTD (Table 3; FIG. 23) or the NTD is destabilized through removal of an essential $Zn^{+2}$ ion from the wild type protein (Table 4; FIG. 25). The modeling experiments indicate that the envelopes of the E11K derivative (FIG. 28) and EDTA-derived wild type dimer (not shown) can accommodate a centrally located core-core interface, with the NTD and CTD domains extended to either side. The second dimer form has a reaching dimer architecture similar to that derived for wild type ASV IN (Examples above). In this dimer, the core domains lie at opposite poles, and the structure is stabilized by interactions of the NTD of one monomer with the core and CTD of the second monomer as well as CTD-CTD interactions, mediated by Trp-243 stacking (Table 4 and FIG. 27). Interruption of the 4-tiered π interaction between conserved hydrophobic amino acids at the HIV IN core-core interface resulted in formation of a homogeneous reaching dimer. Only substitution of Phe-181 to either T or A produced monodispersed dimer preparations. Proteins with substitutions at the other positions formed either aggregates or equilibrium mixtures. When the core-core interface is compromised by the F181T substitution, disruption of NTD interactions by EDTA treatment leads to production of IN monomers (FIG. 25).

SAXS analysis indicates that the wild type IN tetramer has a $D_{max}$ similar to that of the F181T dimer, but that the envelope volume of this tetramer and the F181T IN dimer are 260 and 130 Å3, respectively (Table 4). The results also showed that the HIV IN tetramer conformations are only slightly affected by the presence of the metal cofactor $Mg^{+2}$ without any gross change in the overall architecture.

Comparable values were obtained from the PFV intasome crystal structure: (AG) for the NTD-core interface of the PFV inner dimer is −14.5 kcal/mol and for the core-core interface in the outer dimer the value is −15.3 kcal/mol. Although this calculation only relates to protein-protein interactions in the reaching dimer interface of the PFV NTD+NED with the core residues, it is believed that bound viral DNA contributes to complex formation and stability of the intasome. Overall, the HIV and PFV examples suggest that both dimer interfaces have similar stabilities. These estimates imply that wild type HIV IN can exist in two dimer forms in solution. If one interface has been compromised, the predominant form will be the alternate dimer.

Given the existence of flexible linkers from the core to the NTD and CTD and the potential for dynamic motion of these domains, as suggested in the Examples above, it is believed (without intending to be limited to any particular theory or mechanism of action) to be possible that a transient tetramer conformation can favor viral DNA capture by one of the stacked reaching dimers, which then becomes the inner dimer of an intasome that performs catalysis. The terminal domains of the other stacked reaching dimer might simultaneously disengage to assume auxiliary functions.

Example 10

Reaching Dimer Dissociation and Stabilization

Figure 31:
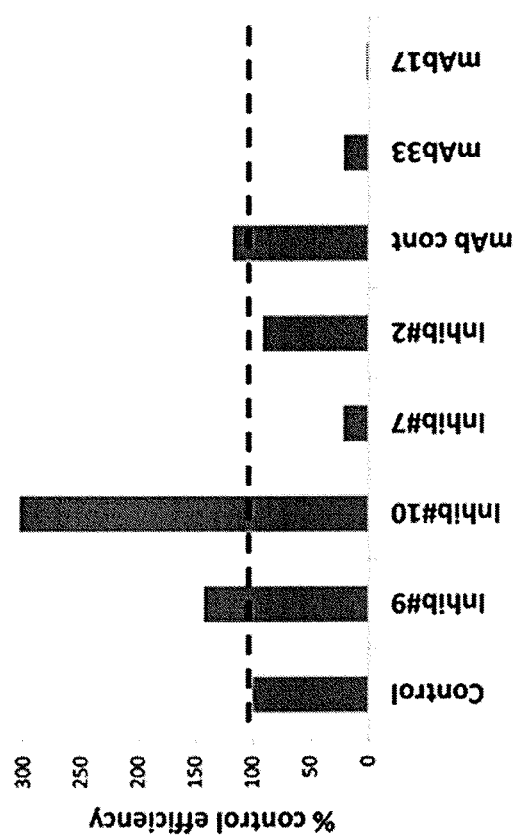
FIG. 31 shows FRET assay validation. This graph shows protein dimer association as assayed by intermolecular FRET, with values expressed as a percent efficiency for untreated HIV IN (F181T) dimer formation at 2 µM (control). The effects of monoclonal antibodies and four small molecule inhibitors (each at 1 µM) are shown.

A multimerization assay based on fluorescence resonance energy transfer (FRET) between donor and acceptor dyes attached to C280 in HIV IN was used. The F181T substitution was introduced in order to monitor reaching dimer formation specifically (see Table 1 and FIGS. 9 and 11). One preparation was labeled with a donor fluorophore (Cy3) and a second with the acceptor (Cy5). Upon mixing (final conc. IN between 0.5 to 2 µM) and equilibration, the FRET efficiency obtained is consistent with the expected apparent distance of 60-65 Å in a reaching dimer. The Z' factor of 0.7 obtained with this assay is in the "excellent" range for high throughput screening, and additional adjustments (e.g., use of alternative dye pairs, filter changes) may allow us to improve sensitivity even further. To validate the assay, the effects of monoclonal antibodies specific for the CTD (mAb33) or NTD (mAb17) of HIV IN were tested (FIG. 31). The results show that both mAbs inhibit FRET-monitored self-association, demonstrating that accessibility of both domains is required for reaching dimer formation. The ability of the FRET assay to discriminate between alternative effects on IN self-association is illustrated by the results with selected non-active-site small molecule inhibitors, three of which (#7, #9, and #10) exhibited an $IC_{50}$ in the low µM range in the concerted integration assay. In the FRET assay, these compounds fall into three classes, those that: 1—stabilize the FRET signal (#9 and #10); 2—inhibit the FRET signal (#7) and; 3—show little or no effect (#2). Controls for these four compounds show that their effects are not due to intrinsic fluorescence or quench of the FRET dyes. These preliminary results support the notion that compounds that either stabilize or block reaching dimer formation can result in inhibition of catalysis by IN.

The invention is not limited to the embodiments described and exemplified above, but is capable of variation and modification within the scope of the appended claims.

We claim:

1. A method for inhibiting human immunodeficiency virus (HIV) integrase reaching dimer formation, comprising contacting the HIV integrase monomers with an antibody comprising the VH domain and the VL domain of the single chain Fv amino acid sequence of SEQ ID NO: 194 or with an antibody comprising the VH domain and the VL domain of the single chain Fv amino acid sequence of SEQ ID NO: 195, thereby inhibiting the formation of the reaching dimer.

2. The method of claim 1, wherein the HIV integrase monomers are expressed in a human T lymphocyte or a human macrophage.

3. The method of claim 1, wherein the antibody comprising the VH domain and the VL domain of the single chain Fv amino acid sequence of SEQ ID NO: 194 is a single chain Fv.

4. The method of claim 1, wherein the antibody comprising the VH domain and the VL domain of the single chain Fv amino acid sequence of SEQ ID NO: 195 is a single chain Fv.

5. The method of claim 1, wherein the antibody comprising the VH domain and the VL domain of the single chain Fv amino acid sequence of SEQ ID NO: 194 is a monoclonal antibody.

6. The method of claim 1, wherein the antibody comprising the VH domain and the VL domain of the single chain Fv amino acid sequence of SEQ ID NO: 195 is a monoclonal antibody.

7. A method for dissociating a human immunodeficiency virus (HIV) integrase reaching dimer, comprising contacting the reaching dimer with an antibody comprising the VH domain and the VL domain of the single chain Fv amino acid sequence of SEQ ID NO: 194 or with an antibody comprising the VH domain and the VL domain of the single chain Fv amino acid sequence of SEQ ID NO: 195, thereby dissociating the reaching dimer.

8. The method of claim 7, wherein the reaching dimer is expressed in a human T lymphocyte or a human macrophage.

9. The method of claim 7, wherein the antibody comprising the VH domain and the VL domain of the single chain Fv amino acid sequence of SEQ ID NO: 194 is a single chain Fv.

10. The method of claim 7, wherein the antibody comprising the VH domain and the VL domain of the single chain Fv amino acid sequence of SEQ ID NO: 195 is a single chain Fv.

11. The method of claim 7, wherein the antibody comprising the VH domain and the VL domain of the single chain Fv amino acid sequence of SEQ ID NO: 194 is a monoclonal antibody.

12. The method of claim 7, wherein the antibody comprising the VH domain and the VL domain of the single chain Fv amino acid sequence of SEQ ID NO: 195 is a monoclonal antibody.

* * * * *

UNITED STATES PATENT AND TRADEMARK OFFICE
CERTIFICATE OF CORRECTION

| | |
|---|---|
| PATENT NO. | : 9,533,040 B2 |
| APPLICATION NO. | : 13/923494 |
| DATED | : January 3, 2017 |
| INVENTOR(S) | : Anna Marie Skalka et al. |

It is certified that error appears in the above-identified patent and that said Letters Patent is hereby corrected as shown below:

In the Specification

In Column 1, the paragraph under the Statement of Government Support, Lines 20-23 should read:
-- This invention was made with government support under Grant Nos. AI40385, CA71515, and CA006927 awarded by the National Institutes of Health. The government has certain rights in the invention. --

Signed and Sealed this
Third Day of October, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 195

<210> SEQ ID NO 1
<211> LENGTH: 14
<212> TYPE: PRT
<213> ORGANISM: Avian sarcoma virus

<400> SEQUENCE: 1

Lys Val Lys Pro Asp Ile Thr Gln Asp Glu Val Thr Lys Lys
1               5                   10

```
<210> SEQ ID NO 2
<211> LENGTH: 6
<212> TYPE: PRT
<213> ORGANISM: Avian sarcoma virus

<400> SEQUENCE: 2

Gly His Met Pro Leu Arg
1               5

<210> SEQ ID NO 3
<211> LENGTH: 21
<212> TYPE: PRT
<213> ORGANISM: Avian sarcoma virus

<400> SEQUENCE: 3

Ala Ile Lys Thr Asp Asn Gly Ser Cys Phe Thr Ser Lys Ser Thr Arg
1               5                   10                  15

Glu Trp Leu Ala Arg
            20

<210> SEQ ID NO 4
<211> LENGTH: 286
<212> TYPE: PRT
<213> ORGANISM: Avian sarcoma virus

<400> SEQUENCE: 4

Pro Leu Arg Glu Ala Lys Asp Leu His Thr Ala Leu His Ile Gly Pro
1               5                   10                  15

Arg Ala Leu Ser Lys Ala Cys Asn Ile Ser Met Gln Gln Ala Arg Glu
                20                  25                  30

Val Val Gln Thr Cys Pro His Cys Asn Ser Ala Pro Ala Leu Glu Ala
            35                  40                  45

Gly Val Asn Pro Arg Gly Leu Gly Pro Leu Gln Ile Trp Gln Thr Asp
        50                  55                  60

Phe Thr Leu Glu Pro Arg Met Ala Pro Arg Ser Trp Leu Ala Val Thr
65                  70                  75                  80

Val Asp Thr Ala Ser Ser Ala Ile Val Val Thr Gln His Gly Arg Val
                85                  90                  95

Thr Ser Val Ala Ala Gln His His Trp Ala Thr Ala Ile Ala Val Leu
                100                 105                 110

Gly Arg Pro Lys Ala Ile Lys Thr Asp Asn Gly Ser Cys Phe Thr Ser
            115                 120                 125

Lys Ser Thr Arg Glu Trp Leu Ala Arg Trp Gly Ile Ala His Thr Thr
        130                 135                 140

Gly Ile Pro Gly Asn Ser Gln Gly Gln Ala Met Val Glu Arg Ala Asn
145                 150                 155                 160

Arg Leu Leu Lys Asp Lys Ile Arg Val Leu Ala Glu Gly Asp Gly Phe
                165                 170                 175

Met Lys Arg Ile Pro Thr Ser Lys Gln Gly Glu Leu Leu Ala Lys Ala
                180                 185                 190

Met Tyr Ala Leu Asn His Phe Glu Arg Gly Glu Asn Thr Lys Thr Pro
            195                 200                 205

Ile Gln Lys His Trp Arg Pro Thr Val Leu Thr Glu Gly Pro Pro Val
        210                 215                 220

Lys Ile Arg Ile Glu Thr Gly Glu Trp Glu Lys Gly Trp Asn Val Leu
225                 230                 235                 240
```

Val Trp Gly Arg Gly Tyr Ala Ala Val Lys Asn Arg Asp Thr Asp Glu
            245                 250                 255

Val Ile Trp Val Pro Ser Arg Lys Val Lys Pro Asp Ile Thr Gln Lys
        260                 265                 270

Asp Glu Val Thr Lys Lys Asp Glu Ala Ser Pro Leu Phe Ala
        275                 280                 285

<210> SEQ ID NO 5
<211> LENGTH: 289
<212> TYPE: PRT
<213> ORGANISM: Avian sarcoma virus

<400> SEQUENCE: 5

Gly His Met Pro Leu Arg Glu Ala Lys Asp Leu His Thr Ala Leu His
1               5                   10                  15

Ile Gly Pro Arg Ala Leu Ser Lys Ala Cys Asn Ile Ser Met Gln Gln
            20                  25                  30

Ala Arg Glu Val Val Gln Thr Cys Pro His Cys Asn Ser Ala Pro Ala
        35                  40                  45

Leu Glu Ala Gly Val Asn Pro Arg Gly Leu Gly Pro Leu Gln Ile Trp
    50                  55                  60

Gln Thr Asp Phe Thr Leu Glu Pro Arg Met Ala Pro Arg Ser Trp Leu
65                  70                  75                  80

Ala Val Thr Val Asp Thr Ala Ser Ser Ala Ile Val Val Thr Gln His
                85                  90                  95

Gly Arg Val Thr Ser Val Ala Ala Gln His His Trp Ala Thr Ala Ile
            100                 105                 110

Ala Val Leu Gly Arg Pro Lys Ala Ile Lys Thr Asp Asn Gly Ser Cys
        115                 120                 125

Phe Thr Ser Lys Ser Thr Arg Glu Trp Leu Ala Arg Trp Gly Ile Ala
    130                 135                 140

His Thr Thr Gly Ile Pro Gly Asn Ser Gln Gly Gln Ala Met Val Glu
145                 150                 155                 160

Arg Ala Asn Arg Leu Leu Lys Asp Lys Ile Arg Val Leu Ala Glu Gly
                165                 170                 175

Asp Gly Phe Met Lys Arg Ile Pro Thr Ser Lys Gln Gly Glu Leu Leu
            180                 185                 190

Ala Lys Ala Met Tyr Ala Leu Asn His Phe Glu Arg Gly Glu Asn Thr
        195                 200                 205

Lys Thr Pro Ile Gln Lys His Trp Arg Pro Thr Val Leu Thr Glu Gly
    210                 215                 220

Pro Pro Val Lys Ile Arg Ile Glu Thr Gly Glu Trp Glu Lys Gly Trp
225                 230                 235                 240

Asn Val Leu Val Trp Gly Arg Gly Tyr Ala Ala Val Lys Asn Arg Asp
                245                 250                 255

Thr Asp Glu Val Ile Trp Val Pro Ser Arg Lys Val Lys Pro Asp Ile
            260                 265                 270

Thr Gln Lys Asp Glu Val Thr Lys Lys Asp Glu Ala Ser Pro Leu Phe
        275                 280                 285

Ala

<210> SEQ ID NO 6
<211> LENGTH: 286
<212> TYPE: PRT
<213> ORGANISM: Avian sarcoma virus

```
<400> SEQUENCE: 6

Pro Leu Arg Glu Ala Lys Asp Leu His Thr Ala Leu His Ile Gly Pro
1               5                   10                  15

Arg Ala Leu Ser Lys Ala Cys Asn Ile Ser Met Gln Gln Ala Arg Glu
            20                  25                  30

Val Val Gln Thr Cys Pro His Cys Asn Ser Ala Pro Ala Leu Glu Ala
        35                  40                  45

Gly Val Asn Pro Arg Gly Leu Gly Pro Leu Gln Ile Trp Gln Thr Asp
    50                  55                  60

Phe Thr Leu Glu Pro Arg Met Ala Pro Arg Ser Trp Leu Ala Val Thr
65                  70                  75                  80

Val Asp Thr Ala Ser Ser Ala Ile Val Val Thr Gln His Gly Arg Val
                85                  90                  95

Thr Ser Val Ala Ala Gln His His Trp Ala Thr Ala Ile Ala Val Leu
            100                 105                 110

Gly Arg Pro Lys Ala Ile Lys Thr Asp Asn Gly Ser Cys Phe Thr Ser
        115                 120                 125

Lys Ser Thr Arg Glu Trp Leu Ala Arg Trp Gly Ile Ala His Thr Thr
130                 135                 140

Gly Ile Pro Gly Asn Ser Gln Gly Gln Ala Met Val Glu Arg Ala Asn
145                 150                 155                 160

Arg Leu Leu Lys Asp Lys Ile Arg Val Leu Ala Glu Gly Asp Gly Phe
                165                 170                 175

Met Lys Arg Ile Pro Thr Ser Lys Gln Gly Glu Leu Leu Ala Lys Ala
            180                 185                 190

Met Tyr Ala Leu Asn His Phe Glu Arg Gly Glu Asn Thr Lys Thr Pro
        195                 200                 205

Ile Gln Lys His Trp Arg Pro Thr Val Leu Thr Glu Gly Pro Pro Val
    210                 215                 220

Lys Ile Arg Ile Glu Thr Gly Glu Trp Glu Lys Gly Trp Asn Val Leu
225                 230                 235                 240

Val Trp Gly Arg Gly Tyr Ala Ala Val Lys Asn Arg Asp Thr Asp Glu
                245                 250                 255

Val Ile Ala Val Pro Ser Arg Lys Val Lys Pro Asp Ile Thr Gln Lys
            260                 265                 270

Asp Glu Val Thr Lys Lys Asp Glu Ala Ser Pro Leu Phe Ala
        275                 280                 285

<210> SEQ ID NO 7
<211> LENGTH: 286
<212> TYPE: PRT
<213> ORGANISM: Avian sarcoma virus

<400> SEQUENCE: 7

Pro Leu Arg Glu Ala Lys Asp Leu His Thr Ala Leu His Ile Gly Pro
1               5                   10                  15

Arg Ala Leu Ser Lys Ala Cys Asn Ile Ser Met Gln Gln Ala Arg Glu
            20                  25                  30

Val Val Gln Thr Cys Pro His Cys Asn Ser Ala Pro Ala Leu Glu Ala
        35                  40                  45

Gly Val Asn Pro Arg Gly Leu Gly Pro Leu Gln Ile Trp Gln Thr Asp
    50                  55                  60

Phe Thr Leu Glu Pro Arg Met Ala Pro Arg Ser Trp Leu Ala Val Thr
65                  70                  75                  80
```

```
Val Asp Thr Ala Ser Ser Ala Ile Val Val Thr Gln His Gly Arg Val
                85                  90                  95

Thr Ser Val Ala Ala Gln His His Trp Ala Thr Ala Ile Ala Val Leu
            100                 105                 110

Gly Arg Pro Lys Ala Ile Lys Thr Asp Asn Gly Ser Cys Phe Thr Ser
        115                 120                 125

Lys Ser Thr Arg Glu Trp Leu Ala Arg Trp Gly Ile Ala His Thr Thr
    130                 135                 140

Gly Ile Pro Gly Asn Ser Gln Gly Gln Ala Met Val Glu Arg Ala Asn
145                 150                 155                 160

Arg Leu Leu Lys Asp Lys Ile Arg Val Leu Ala Glu Gly Asp Gly Phe
                165                 170                 175

Met Lys Arg Ile Pro Thr Ser Lys Gln Gly Glu Leu Leu Ala Lys Ala
            180                 185                 190

Met Tyr Ala Leu Asn His Lys Glu Arg Gly Glu Asn Thr Lys Thr Pro
        195                 200                 205

Ile Gln Lys His Trp Arg Pro Thr Val Leu Thr Glu Gly Pro Pro Val
    210                 215                 220

Lys Ile Arg Ile Glu Thr Gly Glu Trp Glu Lys Gly Trp Asn Val Leu
225                 230                 235                 240

Val Trp Gly Arg Gly Tyr Ala Ala Val Lys Asn Arg Asp Thr Asp Glu
                245                 250                 255

Val Ile Trp Val Pro Ser Arg Lys Val Lys Pro Asp Ile Thr Gln Lys
            260                 265                 270

Asp Glu Val Thr Lys Lys Asp Glu Ala Ser Pro Leu Phe Ala
        275                 280                 285

<210> SEQ ID NO 8
<211> LENGTH: 286
<212> TYPE: PRT
<213> ORGANISM: Avian sarcoma virus

<400> SEQUENCE: 8

Pro Leu Arg Glu Ala Lys Asp Leu His Thr Ala Leu His Ile Gly Pro
1               5                   10                  15

Arg Ala Leu Ser Lys Ala Cys Asn Ile Ser Met Gln Gln Ala Arg Glu
            20                  25                  30

Val Val Gln Thr Cys Pro His Cys Asn Ser Ala Pro Ala Leu Glu Ala
        35                  40                  45

Gly Val Asn Pro Arg Gly Leu Gly Pro Leu Gln Ile Trp Gln Thr Asp
    50                  55                  60

Phe Thr Leu Glu Pro Arg Met Ala Pro Arg Ser Trp Leu Ala Val Thr
65                  70                  75                  80

Val Asp Thr Ala Ser Ser Ala Ile Val Val Thr Gln His Gly Arg Val
                85                  90                  95

Thr Ser Val Ala Ala Gln His His Trp Ala Thr Ala Ile Ala Val Leu
            100                 105                 110

Gly Arg Pro Lys Ala Ile Lys Thr Asp Asn Gly Ser Cys Phe Thr Ser
        115                 120                 125

Lys Ser Thr Arg Glu Trp Leu Ala Arg Trp Gly Ile Ala His Thr Thr
    130                 135                 140

Gly Ile Pro Gly Asn Ser Gln Gly Gln Ala Met Val Cys Arg Ala Asn
145                 150                 155                 160

Arg Leu Leu Lys Asp Lys Ile Arg Val Leu Ala Glu Gly Asp Gly Phe
                165                 170                 175
```

```
Met Lys Arg Ile Pro Thr Ser Lys Gln Gly Glu Leu Leu Ala Lys Ala
            180                 185                 190

Met Tyr Ala Leu Asn His Lys Glu Arg Gly Glu Asn Thr Lys Thr Pro
            195                 200                 205

Ile Gln Lys His Trp Arg Pro Thr Val Leu Thr Glu Gly Pro Pro Val
210                 215                 220

Lys Ile Arg Ile Glu Thr Gly Glu Trp Glu Lys Gly Trp Asn Val Leu
225                 230                 235                 240

Val Trp Gly Arg Gly Tyr Ala Ala Val Lys Asn Arg Asp Thr Asp Glu
                245                 250                 255

Val Ile Trp Val Pro Ser Arg Lys Val Lys Pro Asp Ile Thr Gln Lys
            260                 265                 270

Asp Glu Val Thr Lys Lys Asp Glu Ala Ser Pro Leu Phe Ala
            275                 280                 285

<210> SEQ ID NO 9
<211> LENGTH: 286
<212> TYPE: PRT
<213> ORGANISM: Avian sarcoma virus

<400> SEQUENCE: 9

Pro Leu Arg Glu Ala Lys Asp Leu His Thr Ala Leu His Ile Gly Pro
1               5                   10                  15

Arg Ala Leu Ser Lys Ala Cys Asn Ile Ser Met Gln Gln Ala Arg Glu
                20                  25                  30

Val Val Gln Thr Cys Pro His Cys Asn Ser Ala Pro Ala Leu Glu Ala
            35                  40                  45

Gly Val Asn Pro Arg Gly Leu Gly Pro Leu Gln Ile Trp Gln Thr Asp
50                  55                  60

Phe Thr Leu Glu Pro Arg Met Ala Pro Arg Ser Trp Leu Ala Val Thr
65                  70                  75                  80

Val Asp Thr Ala Ser Ser Ala Ile Val Val Thr Gln His Gly Arg Val
                85                  90                  95

Thr Ser Val Ala Ala Gln His His Trp Ala Thr Ala Ile Ala Val Leu
            100                 105                 110

Gly Arg Pro Lys Ala Ile Lys Thr Asp Asn Gly Ser Ser Phe Thr Ser
        115                 120                 125

Lys Ser Thr Arg Glu Trp Leu Ala Arg Trp Gly Ile Ala His Thr Thr
130                 135                 140

Gly Ile Pro Gly Asn Ser Gln Gly Gln Ala Met Val Glu Arg Ala Asn
145                 150                 155                 160

Arg Leu Leu Lys Asp Lys Ile Arg Val Leu Ala Glu Gly Asp Gly Phe
                165                 170                 175

Met Lys Arg Ile Pro Thr Ser Lys Gln Gly Glu Leu Leu Ala Lys Ala
            180                 185                 190

Met Tyr Ala Leu Asn His Lys Glu Arg Gly Glu Asn Thr Lys Thr Pro
            195                 200                 205

Ile Gln Lys His Trp Arg Pro Thr Val Leu Thr Glu Gly Pro Pro Val
210                 215                 220

Lys Ile Arg Ile Glu Thr Gly Glu Trp Glu Lys Gly Trp Asn Val Leu
225                 230                 235                 240

Val Trp Gly Arg Gly Tyr Ala Ala Val Lys Asn Arg Asp Thr Asp Glu
                245                 250                 255

Val Ile Ala Val Pro Ser Arg Lys Val Lys Pro Asp Ile Thr Gln Lys
```

```
            260                 265                 270
Asp Glu Val Thr Lys Lys Asp Glu Ala Ser Pro Leu Phe Ala
        275                 280                 285

<210> SEQ ID NO 10
<211> LENGTH: 230
<212> TYPE: PRT
<213> ORGANISM: Avian sarcoma virus

<400> SEQUENCE: 10

Gly Val Asn Pro Arg Gly Leu Gly Pro Leu Gln Ile Trp Gln Thr Asp
1               5                   10                  15

Phe Thr Leu Glu Pro Arg Met Ala Pro Arg Ser Trp Leu Ala Val Thr
            20                  25                  30

Val Asp Thr Ala Ser Ser Ala Ile Val Val Thr Gln His Gly Arg Val
        35                  40                  45

Thr Ser Val Ala Ala Gln His His Trp Ala Thr Ala Ile Ala Val Leu
    50                  55                  60

Gly Arg Pro Lys Ala Ile Lys Thr Asp Asn Gly Ser Cys Phe Thr Ser
65                  70                  75                  80

Lys Ser Thr Arg Glu Trp Leu Ala Arg Trp Gly Ile Ala His Thr Thr
                85                  90                  95

Gly Ile Pro Gly Asn Ser Gln Gly Gln Ala Met Val Glu Arg Ala Asn
            100                 105                 110

Arg Leu Leu Lys Asp Lys Ile Arg Val Leu Ala Glu Gly Asp Gly Phe
        115                 120                 125

Met Lys Arg Ile Pro Thr Ser Lys Gln Gly Glu Leu Leu Ala Lys Ala
    130                 135                 140

Met Tyr Ala Leu Asn His Lys Glu Arg Gly Glu Asn Thr Lys Thr Pro
145                 150                 155                 160

Ile Gln Lys His Trp Arg Pro Thr Val Leu Thr Glu Gly Pro Pro Val
                165                 170                 175

Lys Ile Arg Ile Glu Thr Gly Glu Trp Glu Lys Gly Trp Asn Val Leu
            180                 185                 190

Val Trp Gly Arg Gly Tyr Ala Ala Val Lys Asn Arg Asp Thr Asp Glu
        195                 200                 205

Val Ile Trp Val Pro Ser Arg Lys Val Lys Pro Asp Ile Thr Gln Lys
    210                 215                 220

Asp Glu Val Thr Lys Lys
225                 230

<210> SEQ ID NO 11
<211> LENGTH: 207
<212> TYPE: PRT
<213> ORGANISM: Avian sarcoma virus

<400> SEQUENCE: 11

Pro Leu Arg Glu Ala Lys Asp Leu His Thr Ala Leu His Ile Gly Pro
1               5                   10                  15

Arg Ala Leu Ser Lys Ala Cys Asn Ile Ser Met Gln Gln Ala Arg Glu
            20                  25                  30

Val Val Gln Thr Cys Pro His Cys Asn Ser Ala Pro Ala Leu Glu Ala
        35                  40                  45

Gly Val Asn Pro Arg Gly Leu Gly Pro Leu Gln Ile Trp Gln Thr Asp
    50                  55                  60

Phe Thr Leu Glu Pro Arg Met Ala Pro Arg Ser Trp Leu Ala Val Thr
```

```
                65                  70                  75                  80
Val Asp Thr Ala Ser Ser Ala Ile Val Val Thr Gln His Gly Arg Val
                    85                  90                  95

Thr Ser Val Ala Ala Gln His His Trp Ala Thr Ala Ile Ala Val Leu
                100                 105                 110

Gly Arg Pro Lys Ala Ile Lys Thr Asp Asn Gly Ser Cys Phe Thr Ser
                115                 120                 125

Lys Ser Thr Arg Glu Trp Leu Ala Arg Trp Gly Ile Ala His Thr Thr
130                 135                 140

Gly Ile Pro Gly Asn Ser Gln Gly Gln Ala Met Val Glu Arg Ala Asn
145                 150                 155                 160

Arg Leu Leu Lys Asp Lys Ile Arg Val Leu Ala Glu Gly Asp Gly Phe
                165                 170                 175

Met Lys Arg Ile Pro Thr Ser Lys Gln Gly Glu Leu Leu Ala Lys Ala
                180                 185                 190

Met Tyr Ala Leu Asn His Phe Glu Arg Gly Glu Asn Thr Lys Thr
                195                 200                 205

<210> SEQ ID NO 12
<211> LENGTH: 288
<212> TYPE: PRT
<213> ORGANISM: Human immunodeficiency virus

<400> SEQUENCE: 12

Phe Leu Asp Gly Ile Asp Lys Ala Gln Glu Glu His Glu Lys Tyr His
1                   5                   10                  15

Ser Asn Trp Arg Ala Met Ala Ser Asp Phe Asn Leu Pro Pro Val Val
                20                  25                  30

Ala Lys Glu Ile Val Ala Ser Cys Asp Lys Cys Gln Leu Lys Gly Glu
                35                  40                  45

Ala Met His Gly Gln Val Asp Cys Ser Pro Gly Ile Trp Gln Leu Asp
            50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
                100                 105                 110

Val His Thr Asp Asn Gly Ser Asn Phe Thr Ser Thr Thr Val Lys Ala
                115                 120                 125

Ala Cys Trp Trp Ala Gly Ile Lys Gln Glu Phe Gly Ile Pro Tyr Asn
            130                 135                 140

Pro Gln Ser Gln Gly Val Ile Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
                180                 185                 190

Gly Tyr Ser Ala Gly Glu Arg Ile Val Asp Ile Ile Ala Thr Asp Ile
                195                 200                 205

Gln Thr Lys Glu Leu Gln Lys Gln Ile Thr Lys Ile Gln Asn Phe Arg
            210                 215                 220

Val Tyr Tyr Arg Asp Ser Arg Asp Pro Val Trp Lys Gly Pro Ala Lys
225                 230                 235                 240
```

```
Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285

<210> SEQ ID NO 13
<211> LENGTH: 288
<212> TYPE: PRT
<213> ORGANISM: Human immunodeficiency virus

<400> SEQUENCE: 13

Phe Leu Asp Gly Ile Asp Lys Ala Gln Glu Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Val His Thr Asp Asn Gly Ser Asn Phe Thr Ser Thr Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Ile Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Thr Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asp Pro Val Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285

<210> SEQ ID NO 14
<211> LENGTH: 288
<212> TYPE: PRT
<213> ORGANISM: Human immunodeficiency virus

<400> SEQUENCE: 14
```

```
Phe Leu Asp Gly Ile Asp Lys Ala Gln Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Val His Thr Asp Asn Gly Ser Asn Phe Thr Ser Thr Thr Val Lys Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Ile Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asp Pro Val Trp Lys Gly Pro Ala Lys
225                 230                 235                 240

Leu Leu Thr Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285

<210> SEQ ID NO 15
<211> LENGTH: 11
<212> TYPE: PRT
<213> ORGANISM: Avian sarcoma virus

<400> SEQUENCE: 15

Asp Leu His Thr Ala Leu His Ile Gly Pro Arg
1               5                   10

<210> SEQ ID NO 16
<211> LENGTH: 21
<212> TYPE: PRT
<213> ORGANISM: Avian sarcoma virus

<400> SEQUENCE: 16

Ser Trp Leu Ala Val Thr Val Asp Thr Ala Ser Ser Ala Ile Val Val
1               5                   10                  15

Thr Gln His Gly Arg
            20
```

-continued

<210> SEQ ID NO 17
<211> LENGTH: 4
<212> TYPE: PRT
<213> ORGANISM: Avian sarcoma virus

<400> SEQUENCE: 17

Asp Ala Asn Gln
1

<210> SEQ ID NO 18
<211> LENGTH: 9
<212> TYPE: PRT
<213> ORGANISM: Avian sarcoma virus

<400> SEQUENCE: 18

Gly Trp Asn Val Leu Val Trp Gly Arg
1               5

<210> SEQ ID NO 19
<211> LENGTH: 10
<212> TYPE: PRT
<213> ORGANISM: Avian sarcoma virus

<400> SEQUENCE: 19

Ala Met Tyr Ala Leu Asn His Phe Glu Arg
1               5                   10

<210> SEQ ID NO 20
<211> LENGTH: 14
<212> TYPE: PRT
<213> ORGANISM: Avian sarcoma virus

<400> SEQUENCE: 20

His Trp Arg Pro Thr Val Leu Thr Glu Gly Pro Pro Val Lys
1               5                   10

<210> SEQ ID NO 21
<211> LENGTH: 21
<212> TYPE: PRT
<213> ORGANISM: Avian sarcoma virus

<400> SEQUENCE: 21

Val Thr Ser Val Ala Ala Gln His His Trp Ala Thr Ala Ile Ala Val
1               5                   10                  15

Leu Gly Arg Pro Lys
            20

<210> SEQ ID NO 22
<211> LENGTH: 11
<212> TYPE: PRT
<213> ORGANISM: Avian sarcoma virus

<400> SEQUENCE: 22

Val Leu Ala Glu Gly Asp Gly Phe Met Lys Arg
1               5                   10

<210> SEQ ID NO 23
<211> LENGTH: 17
<212> TYPE: PRT
<213> ORGANISM: Avian sarcoma virus

<400> SEQUENCE: 23

Gly Leu Gly Pro Leu Gln Ile Trp Gln Thr Asp Phe Thr Leu Glu Pro
1               5                   10                  15

Arg

<210> SEQ ID NO 24
<211> LENGTH: 17
<212> TYPE: PRT
<213> ORGANISM: Avian sarcoma virus

<400> SEQUENCE: 24

Ile Glu Thr Gly Glu Trp Glu Lys Gly Trp Asn Val Leu Val Trp Gly
1               5                   10                  15

Arg

<210> SEQ ID NO 25
<211> LENGTH: 10
<212> TYPE: PRT
<213> ORGANISM: Avian sarcoma virus

<400> SEQUENCE: 25

Ile Arg Ile Glu Thr Gly Glu Trp Glu Lys
1               5                   10

<210> SEQ ID NO 26
<211> LENGTH: 22
<212> TYPE: PRT
<213> ORGANISM: Avian sarcoma virus

<400> SEQUENCE: 26

Glu Val Val Gln Thr Cys Pro His Cys Asn Ser Ala Pro Ala Leu Glu
1               5                   10                  15

Ala Gly Val Asn Pro Arg
            20

<210> SEQ ID NO 27
<211> LENGTH: 19
<212> TYPE: PRT
<213> ORGANISM: Avian sarcoma virus

<400> SEQUENCE: 27

Ile Arg Ile Glu Thr Gly Glu Trp Glu Lys Gly Trp Asn Val Leu Val
1               5                   10                  15

Trp Gly Arg

<210> SEQ ID NO 28
<211> LENGTH: 19
<212> TYPE: PRT
<213> ORGANISM: Avian sarcoma virus

<400> SEQUENCE: 28

Val Thr Ser Val Ala Ala Gln His His Trp Ala Thr Ala Ile Ala Val
1               5                   10                  15

Leu Gly Arg

<210> SEQ ID NO 29
<211> LENGTH: 15
<212> TYPE: PRT
<213> ORGANISM: Avian sarcoma virus

<400> SEQUENCE: 29

Ala Met Tyr Ala Leu Asn His Phe Glu Arg Gly Glu Asn Thr Lys
1               5                   10                  15

```
<210> SEQ ID NO 30
<211> LENGTH: 10
<212> TYPE: PRT
<213> ORGANISM: Avian sarcoma virus

<400> SEQUENCE: 30

Ala Cys Asn Ile Ser Met Gln Gln Ala Arg
1               5                   10

<210> SEQ ID NO 31
<211> LENGTH: 10
<212> TYPE: PRT
<213> ORGANISM: Avian sarcoma virus

<400> SEQUENCE: 31

Val Leu Ala Glu Gly Asp Gly Phe Met Lys
1               5                   10

<210> SEQ ID NO 32
<211> LENGTH: 14
<212> TYPE: PRT
<213> ORGANISM: Avian sarcoma virus

<400> SEQUENCE: 32

Glu Ala Lys Asp Leu His Thr Ala Leu His Ile Gly Pro Arg
1               5                   10

<210> SEQ ID NO 33
<211> LENGTH: 13
<212> TYPE: PRT
<213> ORGANISM: Avian sarcoma virus

<400> SEQUENCE: 33

Asn Arg Asp Thr Asp Glu Val Ile Trp Val Pro Ser Arg
1               5                   10

<210> SEQ ID NO 34
<211> LENGTH: 11
<212> TYPE: PRT
<213> ORGANISM: Avian sarcoma virus

<400> SEQUENCE: 34

Pro Thr Val Leu Thr Glu Gly Pro Pro Val Lys
1               5                   10

<210> SEQ ID NO 35
<211> LENGTH: 14
<212> TYPE: PRT
<213> ORGANISM: Avian sarcoma virus

<400> SEQUENCE: 35

Asn Arg Asp Thr Asp Glu Val Ile Trp Val Pro Ser Arg Lys
1               5                   10

<210> SEQ ID NO 36
<211> LENGTH: 12
<212> TYPE: PRT
<213> ORGANISM: Avian sarcoma virus

<400> SEQUENCE: 36

Asp Thr Asp Glu Val Ile Trp Val Pro Ser Arg Lys
1               5                   10

<210> SEQ ID NO 37
<211> LENGTH: 8
```

```
<212> TYPE: PRT
<213> ORGANISM: Avian sarcoma virus

<400> SEQUENCE: 37

Ile Glu Thr Gly Glu Trp Glu Lys
1               5

<210> SEQ ID NO 38
<211> LENGTH: 12
<212> TYPE: PRT
<213> ORGANISM: Avian sarcoma virus

<400> SEQUENCE: 38

Ile Arg Val Leu Ala Glu Gly Asp Gly Phe Met Lys
1               5                   10

<210> SEQ ID NO 39
<211> LENGTH: 9
<212> TYPE: PRT
<213> ORGANISM: Avian sarcoma virus

<400> SEQUENCE: 39

Lys Asp Glu Ala Ser Pro Leu Phe Ala
1               5

<210> SEQ ID NO 40
<211> LENGTH: 25
<212> TYPE: PRT
<213> ORGANISM: Avian sarcoma virus

<400> SEQUENCE: 40

Met Ala Pro Arg Ser Trp Leu Ala Val Thr Val Asp Thr Ala Ser Ser
1               5                   10                  15

Ala Ile Val Val Thr Gln His Gly Arg
            20                  25

<210> SEQ ID NO 41
<211> LENGTH: 8
<212> TYPE: PRT
<213> ORGANISM: Avian sarcoma virus

<400> SEQUENCE: 41

Ser Thr Arg Glu Trp Leu Ala Arg
1               5

<210> SEQ ID NO 42
<211> LENGTH: 14
<212> TYPE: PRT
<213> ORGANISM: Avian sarcoma virus

<400> SEQUENCE: 42

Asp Glu Val Thr Lys Lys Asp Glu Ala Ser Pro Leu Phe Ala
1               5                   10

<210> SEQ ID NO 43
<211> LENGTH: 14
<212> TYPE: PRT
<213> ORGANISM: Avian sarcoma virus

<400> SEQUENCE: 43

Ala Leu Ser Lys Ala Cys Asn Ile Ser Met Gln Gln Ala Arg
1               5                   10

<210> SEQ ID NO 44
```

```
<211> LENGTH: 13
<212> TYPE: PRT
<213> ORGANISM: Avian sarcoma virus

<400> SEQUENCE: 44

Val Lys Pro Asp Ile Thr Gln Lys Asp Glu Val Thr Lys
1               5                   10

<210> SEQ ID NO 45
<211> LENGTH: 17
<212> TYPE: PRT
<213> ORGANISM: Avian sarcoma virus

<400> SEQUENCE: 45

Gln Gly Glu Leu Leu Ala Lys Ala Met Tyr Ala Leu Asn His Phe Glu
1               5                   10                  15

Arg

<210> SEQ ID NO 46
<211> LENGTH: 9
<212> TYPE: PRT
<213> ORGANISM: Avian sarcoma virus

<400> SEQUENCE: 46

Lys Val Lys Pro Asp Ile Thr Gln Lys
1               5

<210> SEQ ID NO 47
<211> LENGTH: 8
<212> TYPE: PRT
<213> ORGANISM: Avian sarcoma virus

<400> SEQUENCE: 47

Val Lys Pro Asp Ile Thr Gln Lys
1               5

<210> SEQ ID NO 48
<211> LENGTH: 8
<212> TYPE: PRT
<213> ORGANISM: Avian sarcoma virus

<400> SEQUENCE: 48

Asp Glu Ala Ser Pro Leu Phe Ala
1               5

<210> SEQ ID NO 49
<211> LENGTH: 20
<212> TYPE: PRT
<213> ORGANISM: Avian sarcoma virus

<400> SEQUENCE: 49

Asp Lys Ile Arg Val Leu Ala Glu Gly Asp Gly Phe Met Lys Arg Ile
1               5                   10                  15

Pro Thr Ser Lys
            20

<210> SEQ ID NO 50
<211> LENGTH: 11
<212> TYPE: PRT
<213> ORGANISM: Avian sarcoma virus

<400> SEQUENCE: 50

Pro Asp Ile Thr Gln Lys Asp Glu Val Thr Lys
1               5                   10
```

```
<210> SEQ ID NO 51
<211> LENGTH: 20
<212> TYPE: PRT
<213> ORGANISM: Avian sarcoma virus

<400> SEQUENCE: 51

Ala Asn Arg Leu Leu Lys Asp Lys Ile Arg Val Leu Ala Glu Gly Asp
1               5                   10                  15

Gly Phe Met Lys
            20

<210> SEQ ID NO 52
<211> LENGTH: 15
<212> TYPE: PRT
<213> ORGANISM: Avian sarcoma virus

<400> SEQUENCE: 52

Asp Lys Ile Arg Val Leu Ala Glu Gly Asp Gly Phe Met Lys Arg
1               5                   10                  15

<210> SEQ ID NO 53
<211> LENGTH: 20
<212> TYPE: PRT
<213> ORGANISM: Avian sarcoma virus

<400> SEQUENCE: 53

Gly Tyr Ala Ala Val Lys Asn Arg Asp Thr Asp Glu Val Ile Trp Val
1               5                   10                  15

Pro Ser Arg Lys
            20

<210> SEQ ID NO 54
<211> LENGTH: 9
<212> TYPE: PRT
<213> ORGANISM: Avian sarcoma virus

<400> SEQUENCE: 54

Gly His Met Pro Leu Arg Glu Ala Lys
1               5

<210> SEQ ID NO 55
<211> LENGTH: 28
<212> TYPE: PRT
<213> ORGANISM: Avian sarcoma virus

<400> SEQUENCE: 55

Gly Trp Asn Val Leu Val Trp Gly Arg Gly Tyr Ala Ala Val Lys Asn
1               5                   10                  15

Arg Asp Thr Asp Glu Val Ile Trp Val Pro Ser Arg
            20                  25

<210> SEQ ID NO 56
<211> LENGTH: 20
<212> TYPE: PRT
<213> ORGANISM: Avian sarcoma virus

<400> SEQUENCE: 56

Pro Asp Ile Thr Gln Lys Asp Glu Val Thr Lys Lys Asp Glu Ala Ser
1               5                   10                  15

Pro Leu Phe Ala
            20
```

```
<210> SEQ ID NO 57
<211> LENGTH: 21
<212> TYPE: PRT
<213> ORGANISM: Avian sarcoma virus

<400> SEQUENCE: 57

Gly Leu Gly Pro Leu Gln Ile Trp Gln Thr Asp Phe Thr Leu Glu Pro
1               5                   10                  15

Arg Met Ala Pro Arg
            20

<210> SEQ ID NO 58
<211> LENGTH: 8
<212> TYPE: PRT
<213> ORGANISM: Avian sarcoma virus

<400> SEQUENCE: 58

Gly Tyr Ala Ala Val Lys Asn Arg
1               5

<210> SEQ ID NO 59
<211> LENGTH: 33
<212> TYPE: PRT
<213> ORGANISM: Avian sarcoma virus

<400> SEQUENCE: 59

His Trp Arg Pro Thr Val Leu Thr Glu Gly Pro Val Lys Ile Arg
1               5                   10                  15

Ile Glu Thr Gly Glu Trp Glu Lys Gly Trp Asn Val Leu Val Trp Gly
            20                  25                  30

Arg

<210> SEQ ID NO 60
<211> LENGTH: 23
<212> TYPE: PRT
<213> ORGANISM: Avian sarcoma virus

<400> SEQUENCE: 60

Arg Ile Pro Thr Ser Lys Gln Gly Glu Leu Leu Ala Lys Ala Met Tyr
1               5                   10                  15

Ala Leu Asn His Phe Glu Arg
            20

<210> SEQ ID NO 61
<211> LENGTH: 20
<212> TYPE: PRT
<213> ORGANISM: Avian sarcoma virus

<400> SEQUENCE: 61

Gly His Met Pro Leu Arg Glu Ala Lys Asp Leu His Thr Ala Leu His
1               5                   10                  15

Ile Gly Pro Arg
            20

<210> SEQ ID NO 62
<211> LENGTH: 18
<212> TYPE: PRT
<213> ORGANISM: Avian sarcoma virus

<400> SEQUENCE: 62

Ile Arg Val Leu Ala Glu Gly Asp Gly Phe Met Lys Arg Ile Pro Thr
1               5                   10                  15
```

Ser Lys

<210> SEQ ID NO 63
<211> LENGTH: 19
<212> TYPE: PRT
<213> ORGANISM: Avian sarcoma virus

<400> SEQUENCE: 63

Thr Pro Val Gln Lys His Trp Arg Pro Thr Val Leu Thr Glu Gly Pro
1               5                   10                  15

Pro Val Lys

<210> SEQ ID NO 64
<211> LENGTH: 23
<212> TYPE: PRT
<213> ORGANISM: Avian sarcoma virus

<400> SEQUENCE: 64

Ile Glu Thr Gly Glu Trp Glu Lys Gly Trp Asn Val Leu Val Trp Gly
1               5                   10                  15

Arg Gly Tyr Ala Ala Val Lys
            20

<210> SEQ ID NO 65
<211> LENGTH: 16
<212> TYPE: PRT
<213> ORGANISM: Avian sarcoma virus

<400> SEQUENCE: 65

Asn Arg Asp Thr Asp Glu Val Ile Trp Val Pro Ser Arg Lys Val Lys
1               5                   10                  15

<210> SEQ ID NO 66
<211> LENGTH: 13
<212> TYPE: PRT
<213> ORGANISM: Avian sarcoma virus

<400> SEQUENCE: 66

Ala Ile Lys Thr Asp Asn Gly Ser Cys Phe Thr Ser Lys
1               5                   10

<210> SEQ ID NO 67
<211> LENGTH: 10
<212> TYPE: PRT
<213> ORGANISM: Avian sarcoma virus

<400> SEQUENCE: 67

Thr Asp Asn Gly Ser Cys Phe Thr Ser Lys
1               5                   10

<210> SEQ ID NO 68
<211> LENGTH: 17
<212> TYPE: PRT
<213> ORGANISM: Avian sarcoma virus

<400> SEQUENCE: 68

Gly Trp Asn Val Leu Val Trp Gly Arg Gly Tyr Ala Ala Val Lys Asn
1               5                   10                  15

Arg

<210> SEQ ID NO 69
<211> LENGTH: 15

```
<212> TYPE: PRT
<213> ORGANISM: Avian sarcoma virus

<400> SEQUENCE: 69

Asp Leu His Thr Ala Leu His Ile Gly Pro Arg Ala Leu Ser Lys
1               5                   10                  15

<210> SEQ ID NO 70
<211> LENGTH: 25
<212> TYPE: PRT
<213> ORGANISM: Avian sarcoma virus

<400> SEQUENCE: 70

Ile Arg Ile Glu Thr Gly Glu Trp Glu Lys Gly Trp Asn Val Leu Val
1               5                   10                  15

Trp Gly Arg Gly Tyr Ala Ala Val Lys
            20                  25

<210> SEQ ID NO 71
<211> LENGTH: 21
<212> TYPE: PRT
<213> ORGANISM: Avian sarcoma virus

<400> SEQUENCE: 71

Trp Gly Ile Ala His Thr Thr Gly Ile Pro Gly Asn Ser Gln Gly Gln
1               5                   10                  15

Ala Met Val Glu Arg
            20

<210> SEQ ID NO 72
<211> LENGTH: 23
<212> TYPE: PRT
<213> ORGANISM: Avian sarcoma virus

<400> SEQUENCE: 72

Arg Ile Pro Thr Ser Lys Gln Gly Glu Leu Leu Ala Lys Ala Met Tyr
1               5                   10                  15

Ala Leu Asn His Phe Glu Arg
            20

<210> SEQ ID NO 73
<211> LENGTH: 19
<212> TYPE: PRT
<213> ORGANISM: Avian sarcoma virus

<400> SEQUENCE: 73

Thr Pro Ile Gln Lys His Trp Arg Pro Thr Val Leu Thr Glu Gly Pro
1               5                   10                  15

Pro Val Lys

<210> SEQ ID NO 74
<211> LENGTH: 9
<212> TYPE: PRT
<213> ORGANISM: Avian sarcoma virus

<400> SEQUENCE: 74

Gly His Met Pro Leu Arg Glu Ala Lys
1               5

<210> SEQ ID NO 75
<211> LENGTH: 9
<212> TYPE: PRT
<213> ORGANISM: Avian sarcoma virus
```

<400> SEQUENCE: 75

Lys Val Lys Pro Asp Ile Thr Gln Lys
1               5

<210> SEQ ID NO 76
<211> LENGTH: 9
<212> TYPE: PRT
<213> ORGANISM: Avian sarcoma virus

<400> SEQUENCE: 76

Lys Asp Glu Ala Ser Pro Leu Phe Ala
1               5

<210> SEQ ID NO 77
<211> LENGTH: 6
<212> TYPE: PRT
<213> ORGANISM: Avian sarcoma virus

<400> SEQUENCE: 77

Gly His Met Pro Leu Arg
1               5

<210> SEQ ID NO 78
<211> LENGTH: 5
<212> TYPE: PRT
<213> ORGANISM: Avian sarcoma virus

<400> SEQUENCE: 78

Pro Lys Ala Ile Lys
1               5

<210> SEQ ID NO 79
<211> LENGTH: 17
<212> TYPE: PRT
<213> ORGANISM: Avian sarcoma virus

<400> SEQUENCE: 79

Gln Gly Glu Leu Leu Ala Lys Ala Met Tyr Ala Leu Asn His Phe Glu
1               5                   10                  15

Arg

<210> SEQ ID NO 80
<211> LENGTH: 13
<212> TYPE: PRT
<213> ORGANISM: Avian sarcoma virus

<400> SEQUENCE: 80

Gly Glu Asn Thr Lys Thr Pro Ile Gln Lys His Trp Arg
1               5                   10

<210> SEQ ID NO 81
<211> LENGTH: 12
<212> TYPE: PRT
<213> ORGANISM: Avian sarcoma virus

<400> SEQUENCE: 81

Pro Asp Ile Thr Gln Lys Asp Glu Val Thr Lys Lys
1               5                   10

<210> SEQ ID NO 82
<211> LENGTH: 14
<212> TYPE: PRT
<213> ORGANISM: Avian sarcoma virus

<400> SEQUENCE: 82

Ala Leu Ser Lys Ala Cys Asn Ile Ser Met Gln Gln Ala Arg
1               5                   10

<210> SEQ ID NO 83
<211> LENGTH: 13
<212> TYPE: PRT
<213> ORGANISM: Avian sarcoma virus

<400> SEQUENCE: 83

Pro Thr Val Leu Thr Glu Gly Pro Val Lys Ile Arg
1               5                   10

<210> SEQ ID NO 84
<211> LENGTH: 13
<212> TYPE: PRT
<213> ORGANISM: Avian sarcoma virus

<400> SEQUENCE: 84

Val Lys Pro Asp Ile Thr Gln Lys Asp Glu Val Thr Lys
1               5                   10

<210> SEQ ID NO 85
<211> LENGTH: 14
<212> TYPE: PRT
<213> ORGANISM: Avian sarcoma virus

<400> SEQUENCE: 85

Lys Val Lys Pro Asp Ile Thr Gln Lys Asp Glu Val Thr Lys
1               5                   10

<210> SEQ ID NO 86
<211> LENGTH: 6
<212> TYPE: PRT
<213> ORGANISM: Avian sarcoma virus

<400> SEQUENCE: 86

Gly His Met Pro Leu Arg
1               5

<210> SEQ ID NO 87
<211> LENGTH: 15
<212> TYPE: PRT
<213> ORGANISM: Avian sarcoma virus

<400> SEQUENCE: 87

Lys Val Lys Pro Asp Ile Thr Gln Lys Asp Glu Val Thr Lys Lys
1               5                   10                  15

<210> SEQ ID NO 88
<211> LENGTH: 5
<212> TYPE: PRT
<213> ORGANISM: Avian sarcoma virus

<400> SEQUENCE: 88

Pro Lys Ala Ile Lys
1               5

<210> SEQ ID NO 89
<211> LENGTH: 14
<212> TYPE: PRT
<213> ORGANISM: Avian sarcoma virus

<400> SEQUENCE: 89

```
Val Lys Pro Asp Ile Thr Gln Lys Asp Glu Val Thr Lys Lys
1               5                   10
```

<210> SEQ ID NO 90
<211> LENGTH: 12
<212> TYPE: PRT
<213> ORGANISM: Avian sarcoma virus

<400> SEQUENCE: 90

```
Pro Asp Ile Thr Gln Lys Asp Glu Val Thr Lys Lys
1               5                   10
```

<210> SEQ ID NO 91
<211> LENGTH: 5
<212> TYPE: PRT
<213> ORGANISM: Avian sarcoma virus

<400> SEQUENCE: 91

```
Pro Lys Ala Ile Lys
1               5
```

<210> SEQ ID NO 92
<211> LENGTH: 10
<212> TYPE: PRT
<213> ORGANISM: Avian sarcoma virus

<400> SEQUENCE: 92

```
Leu Leu Asp Lys Ile Arg Val Leu Ala Glu
1               5                   10
```

<210> SEQ ID NO 93
<211> LENGTH: 7
<212> TYPE: PRT
<213> ORGANISM: Avian sarcoma virus

<400> SEQUENCE: 93

```
Gly Asp Gly Phe Met Lys Arg
1               5
```

<210> SEQ ID NO 94
<211> LENGTH: 5
<212> TYPE: PRT
<213> ORGANISM: Avian sarcoma virus

<400> SEQUENCE: 94

```
Leu Leu Lys Asp Lys
1               5
```

<210> SEQ ID NO 95
<211> LENGTH: 10
<212> TYPE: PRT
<213> ORGANISM: Avian sarcoma virus

<400> SEQUENCE: 95

```
Ala Asn Arg Leu Leu Lys Asp Lys Ile Arg
1               5                   10
```

<210> SEQ ID NO 96
<211> LENGTH: 11
<212> TYPE: PRT
<213> ORGANISM: Avian sarcoma virus

<400> SEQUENCE: 96

Leu Leu Lys Asp Lys Ile Arg Val Leu Ala Glu

```
<210> SEQ ID NO 97
<211> LENGTH: 6
<212> TYPE: PRT
<213> ORGANISM: Avian sarcoma virus

<400> SEQUENCE: 97

Gly Asp Gly Phe Met Lys
1               5

<210> SEQ ID NO 98
<211> LENGTH: 9
<212> TYPE: PRT
<213> ORGANISM: Avian sarcoma virus

<400> SEQUENCE: 98

Val Ile Trp Val Pro Ser Arg Lys Val
1               5

<210> SEQ ID NO 99
<211> LENGTH: 7
<212> TYPE: PRT
<213> ORGANISM: Avian sarcoma virus

<400> SEQUENCE: 99

Lys Pro Asp Ile Thr Gln Lys
1               5

<210> SEQ ID NO 100
<211> LENGTH: 8
<212> TYPE: PRT
<213> ORGANISM: Avian sarcoma virus

<400> SEQUENCE: 100

Lys Val Lys Pro Asp Ile Thr Gln
1               5

<210> SEQ ID NO 101
<211> LENGTH: 11
<212> TYPE: PRT
<213> ORGANISM: Avian sarcoma virus

<400> SEQUENCE: 101

Pro Asp Ile Thr Gln Lys Asp Glu Val Thr Lys
1               5                   10

<210> SEQ ID NO 102
<211> LENGTH: 10
<212> TYPE: PRT
<213> ORGANISM: Avian sarcoma virus

<400> SEQUENCE: 102

Lys Val Lys Pro Asp Ile Thr Gln Lys Asp
1               5                   10

<210> SEQ ID NO 103
<211> LENGTH: 4
<212> TYPE: PRT
<213> ORGANISM: Avian sarcoma virus

<400> SEQUENCE: 103

Glu Val Thr Lys
1
```

<210> SEQ ID NO 104
<211> LENGTH: 7
<212> TYPE: PRT
<213> ORGANISM: Avian sarcoma virus

<400> SEQUENCE: 104

Val Lys Pro Asp Ile Thr Gln
1               5

<210> SEQ ID NO 105
<211> LENGTH: 9
<212> TYPE: PRT
<213> ORGANISM: Avian sarcoma virus

<400> SEQUENCE: 105

Lys Val Lys Pro Asp Ile Thr Gln Lys
1               5

<210> SEQ ID NO 106
<211> LENGTH: 20
<212> TYPE: PRT
<213> ORGANISM: Avian sarcoma virus

<400> SEQUENCE: 106

Gly His Met Pro Leu Arg Glu Ala Lys Asp Leu His Thr Ala Leu His
1               5                   10                  15

Ile Gly Pro Arg
            20

<210> SEQ ID NO 107
<211> LENGTH: 9
<212> TYPE: PRT
<213> ORGANISM: Avian sarcoma virus

<400> SEQUENCE: 107

Gly His Met Pro Leu Arg Glu Ala Lys
1               5

<210> SEQ ID NO 108
<211> LENGTH: 21
<212> TYPE: PRT
<213> ORGANISM: Avian sarcoma virus

<400> SEQUENCE: 108

Gly His Met Pro Leu Arg Glu Ala Lys Asp Leu His Thr Ala Leu His
1               5                   10                  15

Ile Gly Pro Arg Ala
            20

<210> SEQ ID NO 109
<211> LENGTH: 5
<212> TYPE: PRT
<213> ORGANISM: Avian sarcoma virus

<400> SEQUENCE: 109

Pro Lys Ala Ile Lys
1               5

<210> SEQ ID NO 110
<211> LENGTH: 14
<212> TYPE: PRT
<213> ORGANISM: Avian sarcoma virus

<400> SEQUENCE: 110

Lys Val Lys Pro Asp Ile Thr Gln Lys Asp Glu Val Thr Lys
1               5                   10

<210> SEQ ID NO 111
<211> LENGTH: 9
<212> TYPE: PRT
<213> ORGANISM: Avian sarcoma virus

<400> SEQUENCE: 111

Lys Val Lys Pro Asp Ile Thr Gln Lys
1               5

<210> SEQ ID NO 112
<211> LENGTH: 6
<212> TYPE: PRT
<213> ORGANISM: Avian sarcoma virus

<400> SEQUENCE: 112

Asp Glu Val Thr Lys Lys
1               5

<210> SEQ ID NO 113
<211> LENGTH: 15
<212> TYPE: PRT
<213> ORGANISM: Avian sarcoma virus

<400> SEQUENCE: 113

Lys Val Lys Pro Asp Ile Thr Gln Lys Asp Glu Val Thr Lys Lys
1               5                   10                  15

<210> SEQ ID NO 114
<211> LENGTH: 8
<212> TYPE: PRT
<213> ORGANISM: Avian sarcoma virus

<400> SEQUENCE: 114

Lys Asp Glu Ala Ser Pro Leu Ala
1               5

<210> SEQ ID NO 115
<211> LENGTH: 5
<212> TYPE: PRT
<213> ORGANISM: Avian sarcoma virus

<400> SEQUENCE: 115

Glu Val Thr Lys Lys
1               5

<210> SEQ ID NO 116
<211> LENGTH: 18
<212> TYPE: PRT
<213> ORGANISM: Avian sarcoma virus

<400> SEQUENCE: 116

Glu Ala Lys Asp Leu His Thr Ala Leu His Ile Gly Pro Arg Ala Leu
1               5                   10                  15

Ser Lys

<210> SEQ ID NO 117
<211> LENGTH: 10
<212> TYPE: PRT
<213> ORGANISM: Avian sarcoma virus

<400> SEQUENCE: 117

```
Val Ile Trp Val Pro Ser Arg Lys Val Lys
1               5                   10

<210> SEQ ID NO 118
<211> LENGTH: 6
<212> TYPE: PRT
<213> ORGANISM: Avian sarcoma virus

<400> SEQUENCE: 118

Pro Asp Ile Thr Gln Lys
1               5

<210> SEQ ID NO 119
<211> LENGTH: 13
<212> TYPE: PRT
<213> ORGANISM: Avian sarcoma virus

<400> SEQUENCE: 119

Val Ile Trp Val Pro Ser Arg Lys Val Lys Pro Asp Ile
1               5                   10

<210> SEQ ID NO 120
<211> LENGTH: 8
<212> TYPE: PRT
<213> ORGANISM: Avian sarcoma virus

<400> SEQUENCE: 120

Thr Gln Lys Asp Glu Val Thr Lys
1               5

<210> SEQ ID NO 121
<211> LENGTH: 9
<212> TYPE: PRT
<213> ORGANISM: Avian sarcoma virus

<400> SEQUENCE: 121

Gly Glu Asn Thr Lys Thr Pro Val Gln
1               5

<210> SEQ ID NO 122
<211> LENGTH: 9
<212> TYPE: PRT
<213> ORGANISM: Avian sarcoma virus

<400> SEQUENCE: 122

Ile Glu Thr Gly Glu Trp Glu Lys Gly
1               5

<210> SEQ ID NO 123
<211> LENGTH: 11
<212> TYPE: PRT
<213> ORGANISM: Avian sarcoma virus

<400> SEQUENCE: 123

Trp Asn Val Leu Val Trp Gly Arg Gly Tyr Ala
1               5                   10

<210> SEQ ID NO 124
<211> LENGTH: 10
<212> TYPE: PRT
<213> ORGANISM: Avian sarcoma virus

<400> SEQUENCE: 124

Val Lys Pro Asp Ile Thr Gln Lys Asp Glu
```

```
1               5                   10
```

<210> SEQ ID NO 125
<211> LENGTH: 4
<212> TYPE: PRT
<213> ORGANISM: Avian sarcoma virus

<400> SEQUENCE: 125

```
Val Thr Lys Lys
1
```

<210> SEQ ID NO 126
<211> LENGTH: 5
<212> TYPE: PRT
<213> ORGANISM: Avian sarcoma virus

<400> SEQUENCE: 126

```
Asp Glu Val Thr Lys
1               5
```

<210> SEQ ID NO 127
<211> LENGTH: 13
<212> TYPE: PRT
<213> ORGANISM: Avian sarcoma virus

<400> SEQUENCE: 127

```
Val Ile Trp Val Pro Ser Arg Lys Val Lys Pro Asp Ile
1               5                   10
```

<210> SEQ ID NO 128
<211> LENGTH: 10
<212> TYPE: PRT
<213> ORGANISM: Avian sarcoma virus

<400> SEQUENCE: 128

```
Pro Asp Ile Thr Gln Lys Asp Glu Val Thr
1               5                   10
```

<210> SEQ ID NO 129
<211> LENGTH: 8
<212> TYPE: PRT
<213> ORGANISM: Avian sarcoma virus

<400> SEQUENCE: 129

```
Val Lys Pro Asp Ile Thr Gln Lys
1               5
```

<210> SEQ ID NO 130
<211> LENGTH: 6
<212> TYPE: PRT
<213> ORGANISM: Avian sarcoma virus

<400> SEQUENCE: 130

```
Gly His Met Pro Leu Arg
1               5
```

<210> SEQ ID NO 131
<211> LENGTH: 4
<212> TYPE: PRT
<213> ORGANISM: Avian sarcoma virus

<400> SEQUENCE: 131

```
Asp Lys Ile Arg
1
```

<210> SEQ ID NO 132
<211> LENGTH: 10
<212> TYPE: PRT
<213> ORGANISM: Avian sarcoma virus

<400> SEQUENCE: 132

Ala Leu Ser Lys Ala Cys Asn Ile Ser Met
1               5                   10

<210> SEQ ID NO 133
<211> LENGTH: 4
<212> TYPE: PRT
<213> ORGANISM: Avian sarcoma virus

<400> SEQUENCE: 133

Gln Gln Ala Arg
1

<210> SEQ ID NO 134
<211> LENGTH: 6
<212> TYPE: PRT
<213> ORGANISM: Avian sarcoma virus

<400> SEQUENCE: 134

Gly His Met Pro Leu Arg
1               5

<210> SEQ ID NO 135
<211> LENGTH: 13
<212> TYPE: PRT
<213> ORGANISM: Avian sarcoma virus

<400> SEQUENCE: 135

Asp Lys Ile Arg Val Leu Ala Glu Gly Asp Gly Phe Met
1               5                   10

<210> SEQ ID NO 136
<211> LENGTH: 21
<212> TYPE: PRT
<213> ORGANISM: Avian sarcoma virus

<400> SEQUENCE: 136

Ala Ile Lys Thr Asp Asn Gly Ser Cys Phe Thr Ser Lys Ser Thr Arg
1               5                   10                  15

Glu Trp Leu Ala Arg
            20

<210> SEQ ID NO 137
<211> LENGTH: 17
<212> TYPE: PRT
<213> ORGANISM: Avian sarcoma virus

<400> SEQUENCE: 137

Gly Trp Asn Val Leu Val Trp Gly Arg Gly Tyr Ala Ala Val Lys Asn
1               5                   10                  15

Arg

<210> SEQ ID NO 138
<211> LENGTH: 13
<212> TYPE: PRT
<213> ORGANISM: Avian sarcoma virus

<400> SEQUENCE: 138

```
Val Lys Pro Asp Ile Thr Gln Lys Asp Glu Val Thr Lys
1               5                   10
```

<210> SEQ ID NO 139
<211> LENGTH: 12
<212> TYPE: PRT
<213> ORGANISM: Avian sarcoma virus

<400> SEQUENCE: 139

```
Ile Arg Val Leu Ala Glu Gly Asp Gly Phe Met Arg
1               5                   10
```

<210> SEQ ID NO 140
<211> LENGTH: 15
<212> TYPE: PRT
<213> ORGANISM: Avian sarcoma virus

<400> SEQUENCE: 140

```
Leu Leu Lys Asp Lys Ile Arg Val Leu Ala Glu Gly Asp Gly Phe
1               5                   10                  15
```

<210> SEQ ID NO 141
<211> LENGTH: 14
<212> TYPE: PRT
<213> ORGANISM: Avian sarcoma virus

<400> SEQUENCE: 141

```
Pro Lys Ala Ile Lys Thr Asp Asn Gly Ser Cys Phe Thr Ser
1               5                   10
```

<210> SEQ ID NO 142
<211> LENGTH: 16
<212> TYPE: PRT
<213> ORGANISM: Avian sarcoma virus

<400> SEQUENCE: 142

```
Ile Pro Thr Ser Lys Gln Gly Glu Leu Leu Ala Lys Ala Met Tyr Ala
1               5                   10                  15
```

<210> SEQ ID NO 143
<211> LENGTH: 6
<212> TYPE: PRT
<213> ORGANISM: Avian sarcoma virus

<400> SEQUENCE: 143

```
Leu Asn His Phe Glu Arg
1               5
```

<210> SEQ ID NO 144
<211> LENGTH: 14
<212> TYPE: PRT
<213> ORGANISM: Avian sarcoma virus

<400> SEQUENCE: 144

```
Asp Lys Ile Arg Val Leu Ala Glu Gly Asp Gly Phe Met Lys
1               5                   10
```

<210> SEQ ID NO 145
<211> LENGTH: 5
<212> TYPE: PRT
<213> ORGANISM: Avian sarcoma virus

<400> SEQUENCE: 145

```
Leu Leu Lys Asp Lys
1               5
```

```
<210> SEQ ID NO 146
<211> LENGTH: 5
<212> TYPE: PRT
<213> ORGANISM: Avian sarcoma virus

<400> SEQUENCE: 146

Pro Lys Ala Ile Lys
1               5

<210> SEQ ID NO 147
<211> LENGTH: 8
<212> TYPE: PRT
<213> ORGANISM: Avian sarcoma virus

<400> SEQUENCE: 147

Ala Asn Arg Leu Leu Lys Asp Lys
1               5

<210> SEQ ID NO 148
<211> LENGTH: 15
<212> TYPE: PRT
<213> ORGANISM: Avian sarcoma virus

<400> SEQUENCE: 148

Val Leu Ala Glu Gly Asp Gly Phe Met Lys Arg Ile Pro Thr Ser
1               5                   10                  15

<210> SEQ ID NO 149
<211> LENGTH: 15
<212> TYPE: PRT
<213> ORGANISM: Avian sarcoma virus

<400> SEQUENCE: 149

Ala Asn Arg Leu Leu Lys Asp Lys Ile Arg Val Leu Ala Glu Gly
1               5                   10                  15

<210> SEQ ID NO 150
<211> LENGTH: 5
<212> TYPE: PRT
<213> ORGANISM: Avian sarcoma virus

<400> SEQUENCE: 150

Asp Gly Phe Met Lys
1               5

<210> SEQ ID NO 151
<211> LENGTH: 13
<212> TYPE: PRT
<213> ORGANISM: Avian sarcoma virus

<400> SEQUENCE: 151

Ala Ile Lys Thr Asp Asn Gly Ser Cys Phe Thr Ser Lys
1               5                   10

<210> SEQ ID NO 152
<211> LENGTH: 11
<212> TYPE: PRT
<213> ORGANISM: Avian sarcoma virus

<400> SEQUENCE: 152

Leu Asn His Phe Glu Arg Gly Glu Asn Thr Lys
1               5                   10
```

```
<210> SEQ ID NO 153
<211> LENGTH: 18
<212> TYPE: PRT
<213> ORGANISM: Avian sarcoma virus

<400> SEQUENCE: 153

Leu Leu Lys Asp Lys Ile Arg Val Leu Ala Glu Gly Asp Gly Phe Met
1               5                   10                  15

Lys Arg

<210> SEQ ID NO 154
<211> LENGTH: 13
<212> TYPE: PRT
<213> ORGANISM: Avian sarcoma virus

<400> SEQUENCE: 154

Ile Arg Val Leu Ala Glu Gly Asp Asp Phe Met Lys Arg
1               5                   10

<210> SEQ ID NO 155
<211> LENGTH: 14
<212> TYPE: PRT
<213> ORGANISM: Avian sarcoma virus

<400> SEQUENCE: 155

Asp Lys Ile Arg Val Leu Ala Glu Gly Asp Gly Phe Met Lys
1               5                   10

<210> SEQ ID NO 156
<211> LENGTH: 16
<212> TYPE: PRT
<213> ORGANISM: Avian sarcoma virus

<400> SEQUENCE: 156

Val Leu Ala Glu Gly Asp Gly Phe Met Lys Arg Ile Pro Thr Ser Lys
1               5                   10                  15

<210> SEQ ID NO 157
<211> LENGTH: 7
<212> TYPE: PRT
<213> ORGANISM: Avian sarcoma virus

<400> SEQUENCE: 157

Leu Leu Lys Asp Lys Ile Arg
1               5

<210> SEQ ID NO 158
<211> LENGTH: 16
<212> TYPE: PRT
<213> ORGANISM: Avian sarcoma virus

<400> SEQUENCE: 158

Ala Ile Lys Thr Asp Asn Gly Ser Cys Phe Thr Ser Lys Ser Thr Arg
1               5                   10                  15

<210> SEQ ID NO 159
<211> LENGTH: 8
<212> TYPE: PRT
<213> ORGANISM: Avian sarcoma virus

<400> SEQUENCE: 159

Val Lys Pro Asp Ile Thr Gln Lys
1               5
```

-continued

```
<210> SEQ ID NO 160
<211> LENGTH: 9
<212> TYPE: PRT
<213> ORGANISM: Avian sarcoma virus

<400> SEQUENCE: 160

Lys Asp Glu Ala Ser Pro Leu Phe Ala
1               5

<210> SEQ ID NO 161
<211> LENGTH: 14
<212> TYPE: PRT
<213> ORGANISM: Avian sarcoma virus

<400> SEQUENCE: 161

Lys Val Lys Pro Asp Ile Thr Gln Lys Asp Glu Val Thr Lys
1               5                   10

<210> SEQ ID NO 162
<211> LENGTH: 18
<212> TYPE: PRT
<213> ORGANISM: Avian sarcoma virus

<400> SEQUENCE: 162

Leu Leu Lys Asp Lys Ile Arg Val Leu Ala Glu Gly Asp Gly Phe Met
1               5                   10                  15

Lys Arg

<210> SEQ ID NO 163
<211> LENGTH: 13
<212> TYPE: PRT
<213> ORGANISM: Avian sarcoma virus

<400> SEQUENCE: 163

Arg Ile Pro Thr Ser Lys Gln Gly Glu Leu Leu Ala Lys
1               5                   10

<210> SEQ ID NO 164
<211> LENGTH: 15
<212> TYPE: PRT
<213> ORGANISM: Avian sarcoma virus

<400> SEQUENCE: 164

Gln Gly Glu Leu Leu Ala Lys Ala Met Tyr Ala Leu Asn His Phe
1               5                   10                  15

<210> SEQ ID NO 165
<211> LENGTH: 15
<212> TYPE: PRT
<213> ORGANISM: Avian sarcoma virus

<400> SEQUENCE: 165

Asp Lys Ile Arg Val Leu Ala Glu Gly Asp Gly Phe Met Lys Arg
1               5                   10                  15

<210> SEQ ID NO 166
<211> LENGTH: 9
<212> TYPE: PRT
<213> ORGANISM: Avian sarcoma virus

<400> SEQUENCE: 166

Val Leu Ala Glu Gly Asp Gly Phe Met
1               5
```

```
<210> SEQ ID NO 167
<211> LENGTH: 11
<212> TYPE: PRT
<213> ORGANISM: Avian sarcoma virus

<400> SEQUENCE: 167

Val Leu Ala Glu Gly Asp Gly Phe Met Lys Arg
1               5                   10

<210> SEQ ID NO 168
<211> LENGTH: 15
<212> TYPE: PRT
<213> ORGANISM: Avian sarcoma virus

<400> SEQUENCE: 168

Asp Lys Ile Arg Val Leu Ala Glu Gly Asp Gly Phe Met Lys Arg
1               5                   10                  15

<210> SEQ ID NO 169
<211> LENGTH: 32
<212> TYPE: PRT
<213> ORGANISM: Avian sarcoma virus

<400> SEQUENCE: 169

Asp Lys Ile Arg Val Leu Ala Glu Gly Asp Gly Phe Met Lys Arg Gly
1               5                   10                  15

Trp Asn Val Leu Val Trp Gly Arg Gly Tyr Ala Ala Val Lys Asn Arg
            20                  25                  30

<210> SEQ ID NO 170
<211> LENGTH: 17
<212> TYPE: PRT
<213> ORGANISM: Avian sarcoma virus

<400> SEQUENCE: 170

Gly Trp Asn Val Leu Val Trp Gly Arg Gly Tyr Ala Ala Val Lys Asn
1               5                   10                  15

Arg

<210> SEQ ID NO 171
<211> LENGTH: 14
<212> TYPE: PRT
<213> ORGANISM: Avian sarcoma virus

<400> SEQUENCE: 171

Val Lys Pro Asp Ile Thr Gln Lys Asp Glu Val Thr Lys Lys
1               5                   10

<210> SEQ ID NO 172
<211> LENGTH: 15
<212> TYPE: PRT
<213> ORGANISM: Avian sarcoma virus

<400> SEQUENCE: 172

Lys Val Lys Pro Asp Ile Thr Gln Lys Asp Glu Val Thr Lys Lys
1               5                   10                  15

<210> SEQ ID NO 173
<211> LENGTH: 13
<212> TYPE: PRT
<213> ORGANISM: Avian sarcoma virus

<400> SEQUENCE: 173

Gly Glu Asn Thr Lys Thr Pro Val Gln Lys His Trp Arg
```

```
1               5               10
```

<210> SEQ ID NO 174
<211> LENGTH: 6
<212> TYPE: PRT
<213> ORGANISM: Avian sarcoma virus

<400> SEQUENCE: 174

Asp Glu Val Thr Lys Lys
1               5

<210> SEQ ID NO 175
<211> LENGTH: 11
<212> TYPE: PRT
<213> ORGANISM: Avian sarcoma virus

<400> SEQUENCE: 175

Pro Asp Ile Thr Gln Lys Asp Glu Val Thr Lys
1               5                   10

<210> SEQ ID NO 176
<211> LENGTH: 14
<212> TYPE: PRT
<213> ORGANISM: Avian sarcoma virus

<400> SEQUENCE: 176

Ala Leu Ser Lys Ala Cys Asn Ile Ser Met Gln Gln Ala Arg
1               5                   10

<210> SEQ ID NO 177
<211> LENGTH: 7
<212> TYPE: PRT
<213> ORGANISM: Avian sarcoma virus

<400> SEQUENCE: 177

Thr Arg Glu Trp Leu Ala Arg
1               5

<210> SEQ ID NO 178
<211> LENGTH: 7
<212> TYPE: PRT
<213> ORGANISM: Avian sarcoma virus

<400> SEQUENCE: 178

Val Lys Pro Asp Ile Gln Lys
1               5

<210> SEQ ID NO 179
<211> LENGTH: 4
<212> TYPE: PRT
<213> ORGANISM: Avian sarcoma virus

<400> SEQUENCE: 179

Asp Lys Ile Arg
1

<210> SEQ ID NO 180
<211> LENGTH: 9
<212> TYPE: PRT
<213> ORGANISM: Avian sarcoma virus

<400> SEQUENCE: 180

Lys Val Lys Pro Asp Ile Thr Gln Lys
1               5

<210> SEQ ID NO 181
<211> LENGTH: 17
<212> TYPE: PRT
<213> ORGANISM: Avian sarcoma virus

<400> SEQUENCE: 181

Gly Tyr Ala Ala Val Lys Asn Arg Asp Thr Asp Glu Val Ile Trp Val
1               5                   10                  15

Pro

<210> SEQ ID NO 182
<211> LENGTH: 5
<212> TYPE: PRT
<213> ORGANISM: Avian sarcoma virus

<400> SEQUENCE: 182

Ser Arg Lys Val Lys
1               5

<210> SEQ ID NO 183
<211> LENGTH: 9
<212> TYPE: PRT
<213> ORGANISM: Avian sarcoma virus

<400> SEQUENCE: 183

Gly Glu Asn Thr Lys Thr Pro Val Gln
1               5

<210> SEQ ID NO 184
<211> LENGTH: 18
<212> TYPE: PRT
<213> ORGANISM: Avian sarcoma virus

<400> SEQUENCE: 184

Glu Ala Lys Asp Leu His Thr Ala Leu His Ile Gly Pro Arg Ala Leu
1               5                   10                  15

Ser Lys

<210> SEQ ID NO 185
<211> LENGTH: 11
<212> TYPE: PRT
<213> ORGANISM: Avian sarcoma virus

<400> SEQUENCE: 185

Val Leu Ala Glu Gly Asp Gly Phe Met Lys Arg
1               5                   10

<210> SEQ ID NO 186
<211> LENGTH: 30
<212> TYPE: PRT
<213> ORGANISM: Avian sarcoma virus

<400> SEQUENCE: 186

Gln Gly Glu Leu Leu Ala Lys Ala Met Tyr Ala Leu Asn His Phe Glu
1               5                   10                  15

Arg Gly Glu Asn Thr Lys Thr Pro Ile Gln Lys His Trp Arg
            20                  25                  30

<210> SEQ ID NO 187
<211> LENGTH: 27
<212> TYPE: PRT
<213> ORGANISM: Avian sarcoma virus

```
<400> SEQUENCE: 187

Ala Leu Ser Lys Ala Cys Asn Ile Ser Met Gln Gln Ala Arg Pro Thr
1               5                   10                  15

Val Leu Thr Glu Gly Pro Pro Val Lys Ile Arg
            20                  25

<210> SEQ ID NO 188
<211> LENGTH: 14
<212> TYPE: PRT
<213> ORGANISM: Avian sarcoma virus

<400> SEQUENCE: 188

Lys Val Lys Pro Asp Ile Thr Gln Lys Asp Glu Val Thr Lys
1               5                   10

<210> SEQ ID NO 189
<211> LENGTH: 24
<212> TYPE: PRT
<213> ORGANISM: Avian sarcoma virus

<400> SEQUENCE: 189

Gly His Met Pro Leu Arg Glu Ala Lys Asp Leu His Thr Ala Leu His
1               5                   10                  15

Ile Gly Pro Arg Ala Leu Ser Lys
            20

<210> SEQ ID NO 190
<211> LENGTH: 16
<212> TYPE: PRT
<213> ORGANISM: Avian sarcoma virus

<400> SEQUENCE: 190

Val Ile Trp Val Pro Ser Arg Lys Val Lys Pro Asp Ile Thr Gln Lys
1               5                   10                  15

<210> SEQ ID NO 191
<211> LENGTH: 21
<212> TYPE: PRT
<213> ORGANISM: Avian sarcoma virus

<400> SEQUENCE: 191

Thr Gly Lys Asp Glu Val Thr Lys Val Ile Trp Val Pro Ser Arg Lys
1               5                   10                  15

Val Lys Pro Asp Ile
            20

<210> SEQ ID NO 192
<211> LENGTH: 23
<212> TYPE: PRT
<213> ORGANISM: Avian sarcoma virus

<400> SEQUENCE: 192

Ile Glu Thr Gly Glu Trp Glu Lys Gly Trp Asn Val Leu Val Trp Gly
1               5                   10                  15

Arg Gly Tyr Ala Ala Val Lys
            20

<210> SEQ ID NO 193
<211> LENGTH: 17
<212> TYPE: PRT
<213> ORGANISM: Avian sarcoma virus

<400> SEQUENCE: 193
```

```
Gly Trp Asn Val Leu Val Trp Gly Arg Gly Tyr Ala Ala Lys Val Lys
1               5                   10                  15

Arg

<210> SEQ ID NO 194
<211> LENGTH: 312
<212> TYPE: PRT
<213> ORGANISM: Mus musculus

<400> SEQUENCE: 194

Met Lys Tyr Leu Leu Pro Thr Ala Ala Ala Gly Leu Leu Leu Leu Ala
1               5                   10                  15

Ala Gln Pro Ala Met Ala Met Gly His His His His His His His His
                20                  25                  30

His His Ser Ser Gly His Ile Asp Asp Asp Asp Lys His Met Asp Ile
            35                  40                  45

Gln Met Thr Gln Ser Pro Ser Ser Leu Ser Ala Ser Leu Gly Gly Lys
    50                  55                  60

Val Thr Ile Thr Cys Lys Ala Ser Gln Asp Ile Tyr Lys Tyr Ile Ala
65                  70                  75                  80

Trp Tyr Gln His Lys Pro Gly Lys Gly Pro Arg Leu Leu Ile His Tyr
                85                  90                  95

Thr Ser Thr Leu Gln Pro Gly Ile Pro Ser Arg Phe Ser Gly Ser Gly
            100                 105                 110

Ser Gly Arg Asp Tyr Ser Phe Ser Ile Ser Asn Leu Glu Pro Glu Asp
        115                 120                 125

Ile Ala Thr Tyr Tyr Cys Leu Gln Tyr Asp Asn Leu Trp Thr Phe Gly
130                 135                 140

Gly Gly Thr Lys Leu Glu Ile Lys Arg Ala Asp Ala Ala Pro Thr Val
145                 150                 155                 160

Ser Ile Phe Pro Pro Ser Ser Lys Leu Gly Pro Gly Gly Gly Gly Ser
                165                 170                 175

Gly Gly Gly Gly Ser Gly Gly Gly Ser Glu Leu Gly Arg Ser Glu
            180                 185                 190

Val Lys Leu Val Glu Ser Gly Gly Gly Leu Val Lys Pro Gly Gly Ser
        195                 200                 205

Leu Lys Leu Ser Cys Ala Ala Ser Gly Phe Ser Phe Ser Ser Tyr Ala
    210                 215                 220

Met Ser Trp Val Arg Gln Thr Pro Glu Lys Arg Leu Glu Trp Val Ala
225                 230                 235                 240

Ser Ile Ser Ser Gly Gly Asn Thr Tyr Tyr Pro Asp Ser Val Lys Gly
                245                 250                 255

Arg Phe Thr Ile Ser Arg Asp Asn Ala Arg Asn Ile Leu Tyr Leu Gln
            260                 265                 270

Met Ser Ser Leu Arg Ser Glu Asp Thr Ala Met Tyr Tyr Cys Ala Arg
        275                 280                 285

Leu Asp Thr Thr Val Glu Gly Asp Trp Tyr Phe Asp Val Trp Gly Ala
    290                 295                 300

Gly Thr Thr Leu Thr Val Ser Ser
305                 310

<210> SEQ ID NO 195
<211> LENGTH: 311
<212> TYPE: PRT
<213> ORGANISM: Mus musculus
```

```
<400> SEQUENCE: 195

Met Lys Tyr Leu Leu Pro Thr Ala Ala Ala Gly Leu Leu Leu Leu Ala
1               5                   10                  15

Ala Gln Pro Ala Met Ala Met Gly His His His His His His His His
            20                  25                  30

His His Ser Ser Gly His Ile Asp Asp Asp Asp Lys His Met Asp Val
        35                  40                  45

Trp Leu Thr Gln Thr Pro Leu Ser Leu Pro Val Ser Leu Gly Asp Gln
    50                  55                  60

Ala Ser Ile Ser Cys Arg Ser Ser Gln Thr Phe Val His Ser Asp Gly
65                  70                  75                  80

Asn Thr Tyr Leu Glu Trp Tyr Leu Gln Lys Pro Gly Gln Ser Pro Lys
                85                  90                  95

Leu Leu Ile Tyr Lys Ile Ser Asn Arg Phe Ser Gly Val Pro Asp Arg
            100                 105                 110

Phe Ser Gly Ser Gly Ser Gly Thr Asp Phe Thr Leu Lys Ile Ser Gly
        115                 120                 125

Val Glu Ala Glu Asp Leu Gly Leu Tyr Tyr Cys Phe Gln Gly Ser His
    130                 135                 140

Val Pro Phe Thr Phe Gly Ser Gly Thr Lys Leu Glu Ile Arg Arg Ala
145                 150                 155                 160

Asp Ala Ala Pro Thr Val Ser Ile Phe Pro Pro Ser Ser Lys Leu Gly
                165                 170                 175

Pro Gly Gly Gly Gly Ser Gly Gly Gly Gly Ser Gly Gly Gly Gly Ser
            180                 185                 190

Glu Leu Gly Arg Ser Gln Val Gln Leu Gln Gln Ser Gly Ala Glu Leu
        195                 200                 205

Val Arg Pro Gly Ala Ser Val Thr Leu Ser Cys Lys Ala Ser Gly Tyr
    210                 215                 220

Thr Phe Ile Glu Tyr Glu Met His Trp Val Lys Gln Ala Pro Val His
225                 230                 235                 240

Gly Leu Glu Trp Ile Gly Ala Val Asp Pro Glu Thr Gly Gly Thr Ala
                245                 250                 255

Tyr Asn Gln Lys Phe Lys Gly Lys Ala Ile Leu Thr Ala Asp Lys Ser
            260                 265                 270

Ser Ser Thr Gly Tyr Met Glu Leu Arg Ser Leu Thr Ser Glu Ser Ser
        275                 280                 285

Ala Val Tyr Tyr Cys Ala Arg Gln Gly Leu Gly Tyr Trp Gly Gln Gly
    290                 295                 300

Thr Leu Val Thr Val Ser Ala
305                 310
```